(12) United States Patent
Fujii et al.

(10) Patent No.: US 9,040,476 B2
(45) Date of Patent: *May 26, 2015

(54) SKIN CLEANSER COMPOSITION

(75) Inventors: Ryosuke Fujii, Wakayama (JP);
Yasuhiro Doi, Wakayama (JP);
Masanori Takai, Wakayama (JP);
Hiromoto Mizushima, Tokyo (JP); Rie Tanaka, Miyagi (JP)

(73) Assignee: KAO CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/976,716

(22) PCT Filed: Dec. 27, 2011

(86) PCT No.: PCT/JP2011/080345
§ 371 (c)(1),
(2), (4) Date: Jul. 25, 2013

(87) PCT Pub. No.: WO2012/091072
PCT Pub. Date: Jul. 5, 2012

(65) Prior Publication Data
US 2013/0296212 A1 Nov. 7, 2013

(30) Foreign Application Priority Data

Dec. 28, 2010 (JP) ................................. 2010-294121
May 2, 2011 (JP) ................................. 2011-103312

(51) Int. Cl.
*C11D 1/00* (2006.01)
*C11D 1/62* (2006.01)
*A61Q 19/10* (2006.01)
*A61K 8/73* (2006.01)
*C08B 11/193* (2006.01)

(52) U.S. Cl.
CPC ................ *A61K 8/731* (2013.01); *A61Q 19/10* (2013.01); *C08B 11/193* (2013.01)

(58) Field of Classification Search
CPC ............ C11D 1/00; C11D 1/62; C11D 3/227; C11D 3/3769; A61K 8/731; A61Q 19/10
USPC ......... 510/123, 130, 151, 421, 471, 473, 504; 424/70.13, 70.19
See application file for complete search history.

(56) References Cited

U.S. PATENT DOCUMENTS

| 3,472,840 | A | 10/1969 | Stone et al. |
| 3,816,616 | A | 6/1974 | Anguillo et al. |
| 8,632,761 | B2 * | 1/2014 | Doi et al. ................. 424/70.13 |
| 2005/0227902 | A1 | 10/2005 | Erazo-Majewicz et al. |
| 2006/0073110 | A1 | 4/2006 | Modi |
| 2010/0274001 | A1 | 10/2010 | Okutsu et al. |
| 2012/0015894 | A1 | 1/2012 | Terada |
| 2012/0214985 | A1 | 8/2012 | Takai et al. |
| 2012/0230934 | A1 | 9/2012 | Doi et al. |

FOREIGN PATENT DOCUMENTS

| EP | 0149249 A2 | 7/1985 |
| EP | 2500012 A1 | 9/2012 |
| JP | 45-20318 | 7/1970 |
| JP | 54-87787 A | 7/1979 |
| JP | 59-42681 B2 | 10/1984 |
| JP | 4-230614 A | 8/1992 |
| JP | 2000-143462 A | 5/2000 |
| JP | 2000-327541 A | 11/2000 |
| JP | 2001-513538 A | 9/2001 |
| JP | 2001-513539 A | 9/2001 |
| JP | 2005-306843 A | 11/2005 |
| JP | 2006-151992 A | 6/2006 |
| JP | 2008-514604 A | 5/2008 |
| JP | 2009-143997 A | 7/2009 |
| JP | 2009-263291 A | 11/2009 |
| WO | WO 99/09947 A1 | 3/1999 |
| WO | WO 99/09948 A1 | 3/1999 |
| WO | WO 2010/035893 A2 | 4/2010 |
| WO | WO 2010/113446 A1 | 10/2010 |
| WO | WO 2011/019876 A2 | 2/2011 |
| WO | WO 2011/052733 A1 | 5/2011 |
| WO | WO 2011/059063 A1 | 5/2011 |

OTHER PUBLICATIONS

English machine translation for JP-59-42681-B2, published Oct. 17, 1984.
International Search Report for PCT/JP2011/080345 dated Apr. 17, 2012.
Extended European Search Report dated Nov. 6, 2014, issued in European Application No. 11854139.0.
International Search Report and Written Opinion of the International Searching Authority, together with English translation of the International Search Report, dated Apr. 17, 2012, issued in International Application No. PCT/JP2011/080346.
International Search Report issued Jan. 11, 2011, in International Application No. PCT/JP2010/70211.
Matsuzaki, F., "Progress of the recent emulsion technology application as the emulsifier of the polyelectrolyte complex," Fragrance Journal, vol. 26, No. 8, Aug. 15, 1998, (14 pages), including a full English machine translation of pp. 42-46 and p. 135.
Sato et al., "Shampoo," Perfumery-and-cosmetics science, Mar. 20, 1997, (23 pages), including a full English machine translation of pp. 126-131.
Written Opinion of the International Searching Authority, dated Apr. 17, 2012, issued in International Application No. PCT/JP2011/080345.
Extended European Search Report, issued Nov. 5, 2014, for European Application No. 11852470.1.

* cited by examiner

*Primary Examiner* — Brian P Mruk
(74) *Attorney, Agent, or Firm* — Birch, Stewart, Kolasch & Birch, LLP

(57) ABSTRACT

The present invention relates to a skin cleanser composition capable of providing an excellent frictional resistance feeling during rinsing and capable of giving an excellent silky feeling with moisturization to the skin after drying, and to a method for producing the composition. The skin cleanser composition contains a cat ionized hydroxypropyl cellulose (A) and a surfactant (B), and the cationized hydroxypropyl cellulose (A) has an anhydroglucose-derived main chain, and has a degree of substitution with cationized ethyleneoxy group of from 0.01 to 3.0 and a degree of substitution with propyleneoxy group of from 0.01 to 2.9.

10 Claims, No Drawings

SKIN CLEANSER COMPOSITION

FIELD OF THE INVENTION

The present invention relates to a skin cleanser composition containing a cationized hydroxypropyl cellulose, and to a method for producing it.

BACKGROUND OF THE INVENTION

Heretofore, various types of ionic surfactants have been incorporated in cleanser compositions for skin and hair. Though having a high detergency, these could not be sufficiently satisfactory in point of irritation to skin and others, foamability in washing, feeling during and after washing, feeling after drying and others.

Consequently, for the purpose of improving the foamability and the foam quality in washing and improving the feeling during and after washing, general-purpose cationic polymers, nonionic polymers, silicones and others are additionally used, which, however, could not be still satisfactory in point of all the feeling in application, the conditioning effect, the feeling after drying and others.

Further, in many cases, when used along with a sebum or a makeup component, the conditioning component is often defective in that it may have some negative influence on the foamability in washing.

For example, Patent Reference 1 describes adding a water-insoluble oil such as polyisobutene, modified silicone oil or the like to a liquid skin cleanser composition containing a crystalline anionic surfactant and an amorphous surfactant gives an improved rinsing feeling in rinsing.

Patent Reference 2 describes a rinse-off liquid personal cleaning composition containing a water-soluble surfactant and a water-insoluble oil such as polybutene or the like, which gives an excellent rinsing feel and a mild feeling to skin.

Patent Reference 3 discloses a skincare composition containing a surfactant, a specific cationic polygalactomannan and a skincare active component, which is capable of imparting a protective function to skin.

However, when the skin cleanser compositions of Patent References 1 to 3 are used, there are problems in that they are not satisfactory in point of frictional resistance feeling in rinsing (feeling in use thereof, or that is, feeling of frictional resistance in use thereof), they leave a strong remaining feeling or an oily feeling after rinsing and therefore give a sticky feeling, and they could not attain a refreshing feeling after rinsing. In addition, the compositions could not give a comfortable silky feeling with moisturization to the skin after drying.

CITATION LIST

Patent References

Patent Reference 1: JP-T 2001-513538
Patent Reference 2: JP-T 2001-513539
Patent Reference 3: JP-T 2008-514604

SUMMARY OF THE INVENTION

The present invention relates to the following (1) and (2):
(1) A skin cleanser composition containing a cationized hydroxypropyl cellulose (A) and a surfactant (B), wherein the cationized hydroxypropyl cellulose (A) has an anhydroglucose-derived main chain represented by a specific general formula, and has a degree of substitution with cationized ethyleneoxy group of from 0.01 to 3.0 and a degree of substitution with propyleneoxy group of from 0.01 to 2.9.

(2) A method for producing a skin cleanser composition containing a cationized hydroxypropyl cellulose (A) and a surfactant (B), in which the cationized hydroxypropyl cellulose (A) has an anhydroglucose-derived main chain represented by a specific general formula, and has a degree of substitution with cationized ethyleneoxy group of from 0.01 to 3.0 and a degree of substitution with propyleneoxy group of from 0.01 to 2.9, and which includes specific steps.

DETAILED DESCRIPTION OF THE INVENTION

The present invention relates to a skin cleanser composition capable of providing an excellent stop feeling (frictional resistance feeling) during rinsing and capable of giving an excellent silky feeling with moisturization to the skin after drying, and relates to a method for producing it.

The present inventors have found that when a specific cationized hydroxypropyl cellulose is incorporated in a skin cleanser composition, then the above-mentioned problems can be solved.

Specifically, the present invention relates to the following (1) and (2):
(1) A skin cleanser composition containing a cationized hydroxypropyl cellulose (A) and a surfactant (B), wherein the cationized hydroxypropyl cellulose (A) has an anhydroglucose-derived main chain represented by the following general formula (1), and has a degree of substitution with cationized ethyleneoxy group of from 0.01 to 3.0 and a degree of substitution with propyleneoxy group of from 0.01 to 2.9:

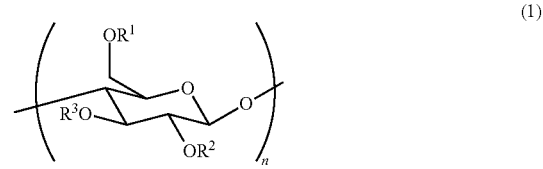

(In the formula, $R^1$, $R^2$ and $R^3$ each independently represent a substituent having a cationized ethyleneoxy group and a propyleneoxy group represented by the following general formula (2); n indicates a mean degree of polymerization of anhydroglucose and is a number of from 20 to 5000.)

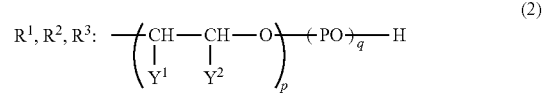

(In the formula, one of $Y^1$ and $Y^2$ is a hydrogen atom and the other is a cationic group represented by the following general formula (3); PO represents a propyleneoxy group; p indicates the number of cationized ethyleneoxy groups ((—CH($Y^1$)—CH($Y^2$)—O—) in the general formula (2) and q indicates the number of propyleneoxy groups (—PO—) therein, each representing 0 or a positive integer; in case where both of p and q are not 0, the addition sequence of the cationized ethyleneoxy group and the propyleneoxy group is not defined, and in case where p and/or q are/is 2 or more, a binding form may be any of like a block co-polymer or like a random co-polymer.)

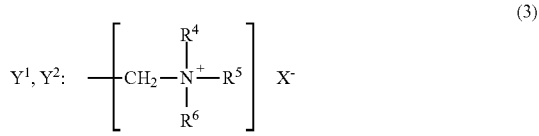

(In the formula, $R^4$, $R^5$ and $R^6$ each independently represent a linear or branched alkyl group having from 1 to 3 carbon atoms, and $X^-$ represents an anionic group.)

(2) A method for producing a skin cleanser composition containing a cationized hydroxypropyl cellulose (A) and a surfactant (B), wherein the cationized hydroxypropyl cellulose (A) has an anhydroglucose-derived main chain represented by the above-mentioned general formula (1), and has a degree of substitution with cationized ethyleneoxy group of from 0.01 to 3.0 and a degree of substitution with propyleneoxy group of from 0.01 to 2.9; the method including the following steps (a-1) to (a-3), the following steps (b-1) to (b-4) or the following steps (c-1) to (c-4):

Step (a-1): a step of adding a cationizing agent to a cellulose-containing raw material and processing it with a grinder, Step (a-2): a step of adding a base to the grinder-processed product obtained in the step (a-1), and while processing it with a grinder, reacting the cellulose-containing raw material and the cationizing agent to give a cationized cellulose, Step (a-3): a step of reacting the cationized cellulose obtained in the step (a-2) with propylene oxide to give the cationized hydroxypropyl cellulose (A), Step (b-1): a step of processing a cellulose-containing raw material with a grinder to give a cellulose-containing raw material that contains a cellulose having a degree of crystallinity of from 10 to 50%, Step (b-2): a step of adding to the cellulose-containing raw material obtained in the step (b-1), a base in an amount of from 0.6 to 1.5 molar times per mol of the anhydroglucose unit that constitutes the cellulose in the cellulose-containing raw material, and water in an amount of from 20 to 100% by mass relative to the cellulose in the cellulose-containing raw material, thereby giving an alkali cellulose, Step (b-3): a step of reacting the alkali cellulose obtained in the step (b-2) and propylene oxide to give a hydroxypropyl cellulose, Step (b-4): a step of reacting the hydroxypropyl cellulose obtained in the step (b-3) with a cationizing agent to give the cationized hydroxypropyl cellulose (A), Step (c-1): a step of processing a mixture of a cellulose-containing raw material and a base in an amount of from 0.6 to 1.5 molar times per mol of the anhydroglucose unit that constitutes the cellulose in the cellulose-containing raw material, with a grinder under the condition where the water content in the cellulose-containing raw material is at most 10% by weight relative to the cellulose therein, thereby giving a ground cellulose/base mixture in which the mean particle size of the cellulose is from 10 to 150 μm, Step (c-2): a step of adding water to the ground cellulose/base mixture obtained in the step (c-1) to thereby control the water content in the ground cellulose/base mixture to be from 30 to 100% by mass relative to the cellulose in the cellulose-containing raw material used in the step (c-1), thereby giving an alkali cellulose, Step (c-3): a step of reacting the alkali cellulose obtained in the step (c-2) with propylene oxide to give a hydroxypropyl cellulose, Step (c-4): a step of reacting the hydroxypropyl cellulose obtained in the step (c-3) with a cationizing agent to give the cationized hydroxypropyl cellulose (A).

According to the present invention, there can be provided a skin cleanser composition capable of providing an excellent frictional resistance feeling during rinsing and capable of giving an excellent silky feeling with moisturization to the skin after drying, and a method for producing it.

[Skin Cleanser Composition]

The skin cleanser composition of the present invention contains a cationized hydroxypropyl cellulose (A) and a surfactant (B).

[Cationized Hydroxypropyl Cellulose (A)]

The cationized hydroxypropyl cellulose (A) is a cationized hydroxypropyl cellulose (hereinafter this may be referred to as "C-HPC") having an anhydroglucose-derived main chain represented by the following general formula (1), and having a degree of substitution with cationized ethyleneoxy group of from 0.01 to 3.0 and a degree of substitution with propyleneoxy group of from 0.01 to 2.9:

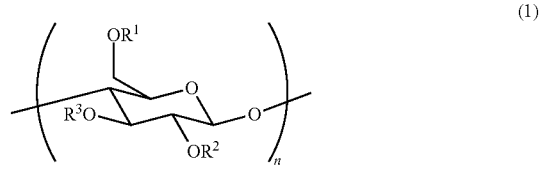

(In the formula, $R^1$, $R^2$ and $R^3$ each independently represent a substituent having a cationized ethyleneoxy group and a propyleneoxy group represented by the following general formula (2); n indicates a mean degree of polymerization of anhydroglucose and is a number of from 20 to 5000.)

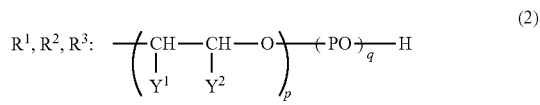

(In the formula, one of $Y^1$ and $Y^2$ is a hydrogen atom and the other is a cationic group represented by the following general formula (3); PO represents a propyleneoxy group; p indicates the number of cationized ethyleneoxy groups ($(-CH(Y^1)-CH(Y^2)-O-)$) in the general formula (2) and q indicates the number of propyleneoxy groups (—PO—) therein, each representing 0 or a positive integer; in case where both of p and q are not 0, the addition sequence of the cationized ethyleneoxy group and the propyleneoxy group is not defined, and in case where p and/or q are/is 2 or more, a binding form may be any of like a block co-polymer or like a random co-polymer.)

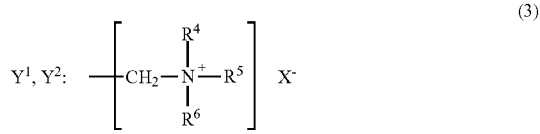

(In the formula, $R^4$, $R^5$ and $R^6$ each independently represent a linear or branched alkyl group having from 1 to 3 carbon atoms, and $X^-$ represents an anionic group.)

<Anhydroglucose-Derived Main Chain Represented by General Formula (1)>

The anhydroglucose-derived main chain represented by the general formula (1) has, as shown in the following general formula (1), a main chain derived from an anhydroglucose.

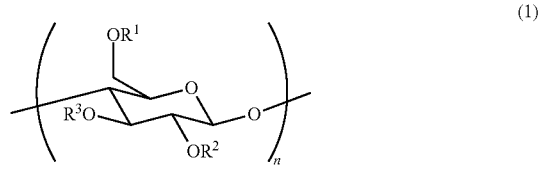

In the general formula (1), $R^1$, $R^2$ and $R^3$ each independently represent a substituent represented by the general formula (2), and $R^1$, $R^2$ and $R^3$ may be the same or different. n $R^1$'s, n $R^2$'s and n $R^3$'s each may be the same or different.

From the viewpoint of the capability of the skin cleanser composition of the present invention capable of providing an excellent frictional resistance feeling during rinsing after washing with it and capable of giving an excellent silky feeling with moisturization to the skin after drying, the mean degree of polymerization n in the general formula (1) is preferably at least 20, more preferably at least 50, even more preferably at least 100. From the same viewpoint as above and from the viewpoint of easiness in production, the mean degree of polymerization n is preferably at most 5000, more preferably at most 1000, even more preferably at most 500. Summing up these viewpoints, the mean degree of polymerization n is preferably from 20 to 5000, more preferably from 50 to 1000, even more preferably from 100 to 500.

In the present invention, the mean degree of polymerization is a viscosity-average degree of polymerization to be determined according to a copper-ammonia process, and is concretely calculated according to the method described in the section of Examples.

(Substituent Represented by General Formula (2))

The substituent represented by the general formula (2) for $R^1$, $R^2$ and $R^3$ in the general formula (1) has, as shown in the following formula (2), a cationized ethyleneoxy group and a propyleneoxy group.

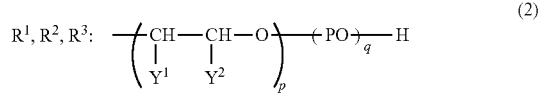

In the general formula (2), one of $Y^1$ and $Y^2$ is a hydrogen atom and the other is a cationic group represented by the following general formula (3), and PO represents a propyleneoxy group.

p indicates the number of cationized ethyleneoxy groups ($(-CH(Y^1)-CH(Y^2)-O-)$) in the general formula (2), and is 0 or a positive integer. From the viewpoint of easiness in production, p is preferably an integer of from 0 to 3, more preferably an integer of from 0 to 2, even more preferably 0 or 1.

q indicates the number of propyleneoxy groups ($-PO-$) in the general formula (2), and is 0 or a positive integer. From the viewpoint of easiness in production, q is preferably an integer of from 0 to 4, more preferably an integer of from 0 to 2, even more preferably 0 or 1.

In case where C-HPC has multiple substituents each represented by the general formula (2) in the molecule thereof, the values of p and q may differ between the substituents.

The total of p and q is preferably an integer of from 1 to 5 from the viewpoint of easiness in production, more preferably from 1 to 4, further preferably from 1 to 3, most preferably 1 or 2.

In case where both of p and q are not 0, the addition sequence of the cationized ethyleneoxy group and the propyleneoxy group is not defined, but from the viewpoint of easiness in production, the addition sequence is preferably as in the general formula (2).

In case where both p and q are not 0 and where p and/or q are/is 2 or more, a binding form may be any of like a block co-polymer or like a random co-polymer, but from the viewpoint of easiness in production, preferred is the binding form like a block co-polymer.

In at least one of n $R^1$'s, n $R^2$'s and n $R^3$'s, p in the general formula (2) is not 0, and in at least one of these, q in the general formula (2) is not 0.

(Cationic Group Represented by General Formula (3))

The cationic group represented by the general formula (3) for $Y^1$ and $Y^2$ in the general formula (2) has the structure shown below.

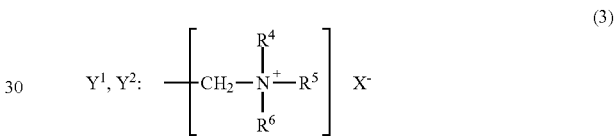

In the general formula (3), $R^4$, $R^5$ and $R^6$ each independently represent a linear or branched alkyl group having from 1 to 3 carbon atoms, and examples thereof include a methyl group, an ethyl group, an n-propyl group and an isopropyl group. Of those, preferred is a methyl group or an ethyl group from the viewpoint of the solubility of C-HPC in water, and more preferred is a methyl group.

In the general formula (3), $X^-$ represents an anionic group which is a counter ion to the ammonium group. Not specifically defined, $X^-$ may be any anionic group. Specific examples of the group include an alkylsulfate ion, a sulfate ion, a phosphate ion, an alkylcarbonate ion, a halide ion, etc. Of those, preferred is a halide ion from the viewpoint of easiness in production. The halide ion includes a fluoride ion, a chloride ion, a bromide ion and an iodide ion. From the viewpoint of the solubility in water and the chemical stability of C-HPC, preferred is a chloride ion or a bromide ion, and more preferred is a chloride ion.

In C-HPC represented by the general formula (1), the degree of substitution with cationized ethyleneoxy group is preferably at most 3.0, more preferably at most 2.7, even more preferably at most 2.5 from the viewpoint that the skin cleanser composition of the present invention can provide an excellent frictional resistance feeling during rinsing after washing and can give an excellent silky feeling with moisturization to the skin after drying and from the viewpoint of the easiness in production. Also preferably, the degree is at least 0.01, more preferably at least 0.1, even more preferably at least 0.6 from the viewpoint that the skin cleanser composition of the present invention can provide an excellent frictional resistance feeling during rinsing after washing and can give an excellent silky feeling with moisturization to the skin after drying. Summing up these viewpoints, the degree of substitution with cationized ethyleneoxy group is from 0.01 to 3.0, preferably from 0.1 to 2.7, more preferably from 0.6 to 2.5, even more preferably from 0.7 to 2.4.

In the present invention, the degree of substitution with cationized ethyleneoxy group means the mean molar number of the cationized ethyleneoxy groups existing in the molecule of C-HPC per mol of the anhydroglucose unit (hereinafter this may be referred to as "AGU") that constitutes the cellulose main chain. The degree of substitution with cationized ethyleneoxy group may be determined according to the method described in the section of Examples given below.

From the viewpoint that the skin cleanser composition of the present invention can provide an excellent frictional resistance feeling during rinsing after washing and can give an excellent silky feeling with moisturization to the skin after drying and from the viewpoint of the easiness in production, the degree of substitution with propyleneoxy group is preferably at most 2.9, more preferably at most 2.5, even more preferably at most 1.6. Also from the viewpoint that the skin cleanser composition of the present invention can provide an excellent frictional resistance feeling during rinsing after washing and can give an excellent silky feeling with moisturization to the skin after drying, the degree is preferably at least 0.01, more preferably at least 0.05, even more preferably at least 0.1. Summing up these viewpoints, the degree of substitution with propyleneoxy group is from 0.01 to 2.9, preferably from 0.05 to 2.5, more preferably from 0.1 to 1.6, even more preferably from 0.15 to 1.5, further more preferably from 0.2 to 1.4.

In the present invention, the degree of substitution with propyleneoxy group means the mean molar number of the propyleneoxy groups existing in the molecule of C-HPC per mol of AGU that constitutes the cellulose main chain. The degree of substitution with propyleneoxy group may be determined according to the method described in the section of Examples given below.

From the viewpoint of the easiness in production, the sum of the degree of substitution with cationized ethyleneoxy group and the degree of substitution with propyleneoxy group is preferably at most 3.2, more preferably at most 3.0, even more preferably at most 2.7; and from the viewpoint that the skin cleanser composition can provide an excellent frictional resistance feeling during rinsing after washing and can give an excellent silky feeling with moisturization to the skin after drying, the sum is preferably at least 0.1, more preferably at least 0.4, even more preferably at least 0.5. Summing up these viewpoints, the sum of the degree of substitution with cationized ethyleneoxy group and the degree of substitution with propyleneoxy group is preferably from 0.1 to 3.2, more preferably from 0.4 to 3.0, even more preferably from 0.5 to 2.7, further more preferably from 0.7 to 2.7, still more preferably from 0.9 to 2.6.

From the viewpoint that the skin cleanser composition can provide an excellent frictional resistance feeling during rinsing after washing and can give an excellent silky feeling with moisturization to the skin after drying, the content of C-HPC in the composition is preferably from 0.005 to 10% by mass, more preferably from 0.02 to 5% by mass, even more preferably from 0.05 to 2% by mass, further more preferably from 0.08 to 1% by mass, still more preferably from 0.1 to 0.5% by mass.

The viscosity of an aqueous 2 mass % solution of C-HPC at 30° C. (hereinafter this may be simply referred to as "2% viscosity") is preferably from 2 to 30000 mPa·s, more preferably from 3 to 25000 mPa·s, even more preferably from 4 to 20000 mPa·s, further more preferably from 5 to 15000 mPa·s, from the viewpoint of the easiness in incorporating the component in the skin cleanser composition and from the viewpoint of the storage stability of the composition. The 2% viscosity is a value to be determined according to the method described in the section of Examples.

[Production of Cationized Hydroxypropyl Cellulose (C-HPC)]

C-HPC in the present invention can be obtained, for example, according to the following production methods (1) to (3):

(1) A method where cellulose is mixed with a large amount of water and a large excess of an alkali metal hydroxide in slurry and reacted with a cationizing agent and propylene oxide.

(2) A method where dimethylacetamide containing lithium chloride is used as a solvent and cellulose is dissolved therein along with an amine or an alcoholate catalyst added thereto, and reacted with a cationizing agent and propylene oxide.

(3) A method where any excessive water or solvent as in the above (1) or (2) is not used but powdery, pellet-like or chip-like cellulose is reacted with a cationizing agent and propylene oxide in the presence of a base.

In the above-mentioned production methods (1) to (3), any of the reaction with a cationizing agent and the reaction with propylene oxide may be carried out first or the two may be carried out simultaneously.

Of these production methods, preferred is the production method (3) from the viewpoint of the easiness in production. Specific examples of the production method for C-HPC according to the method (3) include (3-1) a method of cationizing and hydroxypropylating a cellulose-containing raw material, (3-2) a method of processing a cellulose-containing raw material to give an alkali cellulose and then cationizing and hydroxypropylating the resulting alkali cellulose.

The production method (3) is described concretely hereinunder.

[(3-1) Method of Cationizing and Hydroxypropylating Cellulose-Containing Raw Material]

<Cellulose-Containing Raw Material>

As the cellulose-containing raw material for producing C-HPC, preferably used here is (i) a cellulose-containing raw material having a lowered degree of crystallinity, for example, a low-crystalline powdery cellulose, or (ii) a cellulose-containing raw material having a high degree of crystallinity, for example, pulp.

<(3-1-i) Production of C-HPC Using Cellulose-Containing Raw Material Having Lowered Crystallinity>

(Production of Cellulose-Containing Raw Material Having Lowered Crystallinity)

A cellulose-containing raw material having a lowered crystallinity, for example, a low-crystalline powdery cellulose can be prepared from a sheet-like or a roll-like pulp having a high cellulose purity that is obtained as a general-purpose raw material. The preparing method for low-crystalline powdery cellulose is not specifically defined. For example, there are mentioned the methods described in JP-A 62-236801, 2003-64184, 2004-331918, etc. Of those, more preferred is using a low-crystalline or amorphous powdery cellulose obtained through mechanochemical treatment (hereinafter this may be generically referred to as "low-crystalline powdery cellulose") from the viewpoint of improving the productivity of the cellulose-containing raw material having a lowered crystallinity, for example, the low-crystalline powdery cellulose.

Here the "low crystallinity" of the low-crystalline powdery cellulose means that the cellulose has a large amorphous proportion in the crystal structure thereof. Concretely, from the viewpoint of increasing the reactivity of the material with a cationizing agent and propylene oxide, the degree of crystallinity thereof to be calculated by the math formula (1)

mentioned below is preferably at most 30%, more preferably at most 20%, even more preferably at most 10%, and still more preferred is use of a completely amorphous cellulose of which the degree of crystallinity is nearly 0%.

$$\text{Degree of Crystallinity (\%)} = [(I_{22.6} - I_{18.5})/I_{22.6}] \times 100 \quad (1)$$

(In the formula, $I_{22.6}$ means the diffraction intensity at the lattice plane (002 plane) of a cellulose I-type crystal in X-ray diffractiometry (diffraction angle 2θ=22.6°), and $I_{18.5}$ means the diffraction intensity at the amorphous moiety (diffraction angle 2θ=18.5°.)

As the production method for low-crystalline powdery cellulose through mechanochemical treatment, for example, there is mentioned a method of processing a chip-like pulp obtained by roughly grinding a sheet-like pulp, using a grinder. Before the treatment with a grinder, the chip-like pulp may be processed through an extruder.

The extruder to be used in the method may be a single-screw or double-screw extruder, but preferred is a double-screw extruder. From the viewpoint of imparting strong compression shear force, preferred is an extruder equipped with a so-called kneading disc part in any part of the screw.

The processing method with an extruder is not specifically defined. Preferred is a method where a chip-like pulp is put into an extruder and continuously processed therein.

The grinder includes a roll mill such as a high-pressure compression roll mill, a roll-rotating mill, etc.; a vertical roller mill such as a ring roller mill, a roller-less mill, a boll-less mill, etc.; a chamber vibration-mediated mill such as a rotary ball mill, a vibratory ball mill, a vibratory rod mill, a vibratory tube mill, a planetary ball mill, a centrifugal fluidization mill, etc.; a medium stirring mill such as a column grinder, a stirring column mill, a ventilation column mill, an annular mill, etc.; a consolidation shear mill such as a high-speed centrifugal roller mill, an angmill, etc.; a mortar, a stone mill, etc. Of those, preferred is a chamber vibration-mediated mill or a medium stirring mill from the viewpoint of efficiently lowering the degree of crystallinity of cellulose and from the viewpoint of productivity, and more preferred is a chamber vibration-mediated. Even more preferred is a vibration mill such as a vibratory ball mill, a vibratory rod mill, a vibratory tube mill or the like, and still more preferred is a vibratory ball mill or a vibratory rod mill.

The treatment method may be any of a batch process or a continuous process.

The preferred range of the filling rate with media such as balls, rods or the like may vary depending on the type of the grinder, but is preferably within a range of from 10 to 97%, more preferably from 15 to 95%. When the filling rate falls within the range, then the contact frequency between the pulp and the media may increase and the grinding efficiency can be thereby increased without interfering with the movement of media. Here the filling rate means the apparent volume of the media relative to the volume of the stirring area of the grinder.

In the case of a ball mill, the material of the balls to be used as the media is not specifically defined. For example, there may be mentioned iron, stainless, alumina, zirconia, etc. The outer diameter of the ball is preferably from 0.1 to 100 mm, more preferably from 1 to 50 mm from the viewpoint of efficiently lowering the degree of crystallinity of cellulose.

Also from the viewpoint of efficiently lowering the degree of crystallinity of cellulose, the treatment time in a grinder is preferably from 5 minutes to 72 hours, more preferably from 10 minutes to 30 hours. In treatment in a grinder, the temperature is preferably not higher than 250° C., more preferably from 5 to 200° C. from the viewpoint of minimizing the denaturation and degradation owing to heat generation.

Rods for use as the medium in the grinder are rod-shaped media, of which the cross section may be any of polygon such as tetragon, hexagon or the like, as well as circle, oval, etc.

The outer diameter of the rod is preferably from 0.5 to 200 mm, more preferably from 1 to 100 mm, even more preferably from 5 to 50 mm. The length of the rod is not specifically defined so far as it is shorter than the length of the chamber of the grinder. When the rod size falls within the above range, then a desired grinding force can be applied to cellulose by which the degree of crystallinity of the ground cellulose can be efficiently lowered.

Not specifically defined, the treatment time and the treatment temperature in the rods-filled vibration mill may be the same as the treatment time and the treatment temperature in the above-mentioned ball mill.

According to the above-mentioned methods, it is possible to control the molecular weight of cellulose, and a low-crystalline powdery cellulose having a high degree of polymerization and hardly available in general can be readily prepared. The mean degree of polymerization of the low-crystalline powdery cellulose for use herein is preferably from 20 to 5000, more preferably from 50 to 1000, even more preferably from 100 to 500.

The mean particle size of the low-crystalline powdery cellulose is not specifically defined so far as the cellulose can maintain a good flowable state as powder. Preferably, the mean particle size is at most 300 μm, more preferably at most 150 μm, even more preferably at most 50 μm. From the viewpoint of improving the handleability of the powdery cellulose, the mean particle size thereof is preferably at least 20 μm, more preferably at least 25 μm. If desired, for evading mixing with a minor amount of coarse particles owing to aggregation, preferably used in the reaction are undersize particles having passed through a sieve having a sieve opening of from 300 to 1000 μl or so.

(Cationization of Cellulose-Containing Raw Material Having Lowered Crystallinity)

Produced in the manner as above, the cellulose-containing raw material having a lowered degree of crystallinity, for example, the low-crystalline powdery cellulose is reacted with a glycidyltrialkylammonium salt in the presence of a base for cationization to give a cationized cellulose.

The glycidyltrialkylammonium salt to be used as the cationizing agent includes glycidyltrimethylammonium chloride, glycidyltriethylammonium chloride, glycidyltrimethylammonium bromide, glycidyltriethylammonium bromide, etc. From the viewpoint of availability, preferred is glycidyltrimethylammonium chloride.

The amount of the glycidyltrialkylammonium salt to be added is preferably from 0.01 to 10.0 molar times per mol of AGU in cellulose, more preferably from 0.05 to 8.0 molar times, even more preferably from 0.8 to 7.0 molar times, still more preferably from 1.0 to 6.0 molar times, from the viewpoint that the skin cleanser composition can provide an excellent frictional resistance feeling during rinsing after washing and can give an excellent silky feeling with moisturization to the skin after drying.

The base to be present in the system during cationization includes lithium hydroxide, sodium hydroxide, potassium hydroxide, calcium hydroxide, barium hydroxide, etc. From the viewpoint of availability, general versatility and economic potential, more preferred are sodium hydroxide and barium hydroxide. The amount of the base to be added may vary depending on the type of cellulose, but from the viewpoint of efficiently reacting cellulose and the cationizing agent, the amount is, in general, preferably from 0.05 to 1.0 molar times relative to 1 mol of AGU in cellulose, more preferably from 0.06 to 1.0 molar times, even more preferably from 0.07 to 0.7 molar times, still more preferably from 0.1 to 0.3 molar times.

The water content in the reaction system is preferably at most 100% by mass relative to the cellulose used as the raw material. When the water content relative to the cellulose falls within the range, then the cellulose would not aggregate excessively and therefore can be reacted as a flowable powdery state. From this viewpoint, the water content is preferably at most 80% by mass, more preferably from 5 to 50% by mass.

The reaction temperature is generally from 10 to 85° C., but preferably from 15 to 80° C.

(Hydroxypropylation of Cationized Cellulose)

Produced in the manner as above, the cationized cellulose is reacted with propylene oxide for hydroxypropylation to give C-HPC.

Here the amount of propylene oxide to be used is preferably from 0.01 to 8.0 molar times per mol of AGU in the cellulose molecule, more preferably from 0.1 to 5.0 molar times, even more preferably from 0.2 to 3.0 molar times, from the viewpoint that the skin cleanser composition can provide an excellent frictional resistance feeling during rinsing after washing and can give an excellent silky feeling with moisturization to the skin after drying.

As the catalyst for the hydroxypropylation, usable is a base or an acid. The base catalyst includes alkali metal hydroxides such as sodium hydroxide, potassium hydroxide, lithium hydroxide, etc.; alkaline earth metal hydroxides such as magnesium hydroxide, calcium hydroxide, etc.; tertiary amines such as trimethylamine, triethylamine, triethylenediamine, etc. The acid catalyst includes Lewis acid catalysts such as lanthanide triflates, etc.

Of those, preferred is a base catalyst from the viewpoint of preventing the degree of polymerization of cellulose in the cellulose-containing staring material from lowering, and more preferred is an alkali metal hydroxide. Even more preferred is sodium hydroxide or potassium hydroxide. One or more different types of these catalysts may be used here either singly or as combined.

Not specifically defined, the amount of the catalyst to be used is, in general, preferably from 0.05 to 1.0 molar times per mol of AGU in the cellulose molecule, more preferably from 0.07 to 0.7 molar times, even more preferably from 0.1 to 0.3 molar times.

In case where the cationization step is carried out first, the base used in the cationization step may be used as such as the catalyst in the hydroxypropylation, and addition of any additional catalyst may be omitted in the hydroxypropylation step.

The method of adding propylene oxide is not specifically defined. For example, there are mentioned (a) a method of adding a catalyst to the cationized cellulose and then dropwise adding propylene oxide thereto, and (b) a method adding propylene oxide to the cationized cellulose all at a time and thereafter gradually adding thereto a catalyst to lead the reaction. More preferred is the method (a).

The water content in the reaction system is preferably at most 100% by mass relative to the cellulose used as the raw material. When the water content relative to the cellulose falls within the range, then the cationized cellulose would not aggregate excessively and therefore can be reacted as a flowable powdery state. From this viewpoint, the water content is preferably at most 80% by mass, more preferably from 5 to 50% by mass.

In the present invention, preferably, the cationized cellulose, the catalyst and the propylene oxide are reacted in a flowable powdery state. If desired, the cationized cellulose powder and the catalyst may be previously uniformly mixed and dispersed in a mixing apparatus such as a mixer or the like or by the use of a shaking machine, a mixing mill or the like, and thereafter propylene oxide may be added thereto and reacted.

Preferably, the reaction temperature in hydroxypropylation is from 0 to 150° C.; however, from the viewpoint of preventing polymerization of propylene oxide and preventing any rapid reaction, the temperature is more preferably from 10 to 100° C., even more preferably from 20 to 80° C. The reaction may be carried out under normal pressure.

From the viewpoint of evading the reduction in the molecular weight owing to cleavage of the cellulose chains during the reaction, it is desirable to carryout the reaction in an inert gas atmosphere such as nitrogen, etc.

After the reaction, the unreacted propylene oxide is removed, and thereafter if desired, the system is neutralized, then purified and dried to give C-HPC for use in the present invention.

The neutralization may be carried out according to an ordinary method. For example, in case where a base catalyst is used, a liquid acid such as acetic acid or the like, or a mixed solution of an acid and an inert organic solvent, or an aqueous acid solution may be added to the system for neutralization. The type of the acid is not specifically defined, and the acid may be suitably selected in consideration of corrosion of apparatus, etc. The purification may be carried out by the use of a solvent such as water-containing isopropanol, water-containing acetone solvent or the like and/or by washing with water, or through a dialytic membrane.

Regarding the sequence of the cationization and the hydroxypropylation in the above-mentioned <(3-1-i) Production of C-HPC using cellulose-containing raw material having lowered crystallinity>, the cellulose in the cellulose-containing raw material may be first hydroxypropylated and then cationized, or may be hydroxypropylated and cationized at one time.

From the viewpoint of controlling the degree of substitution with cationized ethyleneoxy group and propyleneoxy group, preferably, the cellulose in the cellulose-containing raw material is first cationized and then hydroxypropylated.

For the purpose of increasing the degree of substitution with cationized ethyleneoxy group, the cationized and hydroxypropylated system may be further again cationized.

In the cationization step and the hydroxypropylation step in the above-mentioned <(3-1-i) Production of C-HPC using cellulose-containing raw material having lowered crystallinity>, the cellulose skeleton to be the main chain is not substantially cleaved, and therefore the mean degree of polymerization of the C-HPC to be obtained could be approximated by the mean degree of polymerization of the powdery cellulose treated for lowering the crystallinity thereof.

<(3-1-ii) Production of C-HPC Using Cellulose-Containing Raw Material Having High Crystallinity>

(Cationization of Cellulose-Containing Raw Material Having High Crystallinity)

In case where a cellulose-containing raw material having a high crystallinity, for example, pulp (hereinafter the cellulose-containing raw material is typically pulp) is used as the cellulose-containing raw material, not using the above-mentioned cellulose-containing raw material having lowered crystallinity, for example, the low-crystalline powdery cellulose, preferably, the cellulose-containing raw material is processed for crystallinity reduction in cationization for the purpose of improving the reactivity of the material.

Concretely, a cationizing agent is added to the cellulose-containing raw material and treated in a grinder for crystallinity reduction, and thereafter a base is added thereto and treated in a grinder for crystallinity reduction while the cellulose-containing raw material is reacted with a cationizing agent thereby giving a cationized cellulose; or a base is added to the cellulose-containing raw material and treated in a grinder for crystallinity reduction, and thereafter a cationizing agent is added thereto and treated in a grinder for crystallinity reduction along with reaction of the cellulose-containing raw material and the cationizing agent thereby giving a cationized cellulose. From the viewpoint of obtaining C-HPC having a high degree of substitution with cationized ethyleneoxy group, preferably, a cationizing agent is added to the cellulose-containing raw material and treated in a grinder, and thereafter a base is added thereto and treated in a grinder, and further a cationizing agent is added thereto and treated in a grinder. Addition of the cationizing agent after addition of the base may be carried out in multiple stages.

From the viewpoint of the solubility in water of the C-HPC obtained through the cationization, in cationization of cellulose, preferably, a cationizing agent is first added to the cellulose-containing raw material and treated in a grinder for crystallinity reduction, and thereafter a base is added thereto and treated in a grinder for crystallinity reduction along with reaction of the cellulose-containing raw material and the cationizing agent.

The cellulose-containing raw material having a high crystallinity includes various types of wood chips; pulps such as wood pulp produced from wood, cotton linter pulp obtained from fibers around cotton seeds, etc.; papers such as newspaper, cardboard, magazine, high-quality paper, etc.; plant stems and leaves such as rice straws, corn stems, etc.; plant shells such as rice husks, palm shells, coconut husks, etc. From the viewpoint of high cellulose purity and productivity of C-HPC, preferred is wood pulp.

The shape of the pulp to be used as the cellulose-containing raw material is not specifically defined so far as not interfering with the introduction thereof into a production apparatus, but from the viewpoint of handleability thereof, preferred is use of sheet-like pulp, or pellet-like or chip-like pulp produced by cutting or roughly grinding sheet-like pulp, or powdery cellulose obtained by finely pulverizing pulp.

The degree of crystallinity of the pulp for use as the cellulose-containing raw material is not defined. However, in general, the treatment of cellulose for crystallinity reduction is accompanied by molecular weight reduction owing to cleavage of cellulose chains, and therefore the cellulose in the cellulose-containing raw material having a low crystallinity has a low molecular weight. Consequently, from the viewpoint of obtaining C-HPC having a high molecular weight, preferred is used of cellulose having a high crystallinity. On the contrary, cellulose having an extremely high crystallinity of more than 95%, as calculated according to the above-mentioned math formula (1), is hardly available. Accordingly, from the viewpoint of the degree of polymerization and the availability, the degree of crystallinity calculated according to the above-mentioned math formula (1) of the cellulose in the cellulose-containing raw material is preferably from 10 to 95%, more preferably from 30 to 90%, even more preferably from 60 to 80%.

The mean degree of polymerization of the cellulose in the cellulose-containing raw material is not defined; however, from the viewpoint of obtaining C-HPC having a high molecular weight, preferred is used of a cellulose having a larger degree of polymerization. From this viewpoint, the mean degree of polymerization of the cellulose in the cellulose-containing raw material is preferably from 20 to 5000, more preferably from 50 to 2000, even more preferably from 100 to 500.

Preferred embodiments of the type and the amount of the cationizing agent, the type of the base, the type of the grinder, and the method and the condition for crystallinity reduction are the same as those described in the section of the above-mentioned <(3-1-i) Production of C-HPC using cellulose-containing raw material having lowered crystallinity>, except the treatment time with grinder for crystallinity reduction and the amount of the base.

The treatment time with grinder for crystallinity reduction is preferably from 1 minute to 5 hours, more preferably from 2 minutes to 3 hours, even more preferably from 5 minutes to 2 hours, from the viewpoint of efficiently lowering the degree of crystallinity of the treated cellulose while preventing the degree of polymerization thereof from lowering.

The amount of the base is preferably from 0.05 to 1.5 molar times per mol of AGU in the cellulose in the cellulose-containing raw material, more preferably from 0.07 to 1.0 molar times, even more preferably from 0.1 to 0.6 molar times, from the viewpoint of efficiently reacting the cellulose with the cationizing agent.

The cationization may go on after addition of the cationizing agent and the base for crystallinity reduction, however, when the reaction is insufficient, it is desirable that the system is ripened at from 10 to 100° C., more preferably from 30 to 80° C. for promoting the reaction.

Even though the cationization is sufficient, a glycidyltrialkylammonium salt may be added to the system to ripen it, whereby a cationized cellulose having a high degree of substitution with cationized ethyleneoxy group can be obtained.

The amount of water in ripening and other preferred embodiments are the same as those for the above-mentioned cationization of low-crystalline powdery cellulose, except the point that a cellulose-containing raw material having a high degree of crystallinity is used in place of the low-crystalline powdery cellulose as the raw material.

From the viewpoint of evading the reduction in the molecular weight owing to cleavage of cellulose chains during reaction, the reaction is preferably carried out in an inert gas atmosphere such as nitrogen, etc.

(Hydroxypropylation of Cationized Cellulose)

The amount of propylene oxide to be used for hydroxypropylation of cationized cellulose in <(3-1-ii) Production of C-HPC using cellulose-containing raw material having high crystallinity: Method (a)>, as well as the catalyst, the reaction condition, the treatment after the reaction and other preferred embodiments are the same as those described for the hydroxypropylation in the above-mentioned <(3-1-i) Production of C-HPC using cellulose-containing raw material having lowered crystallinity>.

Regarding the sequence of cationization and hydroxypropylation in the above-mentioned <(3-1-ii) Production of C-HPC using cellulose-containing raw material having high crystallinity: Method (a)>, the hydroxypropylation of the cellulose-containing raw material may be carried out first and then the cationization may be carried out, or the two may be carried out simultaneously. From the viewpoint of controlling the degree of substitution with cationized ethyleneoxy group and propyleneoxy group, preferably, the cellulose-containing raw material is first cationized and then hydroxypropylated.

From the viewpoint of increasing the degree of substitution with cationized ethyleneoxy group, the cationized and hydroxypropylated system may be further again cationized.

[(3-2) Method of Processing Cellulose-Containing Raw Material to Give Alkali Cellulose and then Cationizing and Hydropropylating the Resulting Alkali Cellulose]
<Cellulose-Containing Raw Material>

As the cellulose-containing raw material for producing C-HPC, preferably used here is (i) a cellulose-containing raw material having a lowered degree of crystallinity or (ii) a cellulose-containing raw material having a high degree of crystallinity, like in [(3-1) Method of cationizing and hydroxypropylating cellulose-containing raw material].

<(3-2-i) Production of C-HPC Using Cellulose-Containing Raw Material Having Lowered Crystallinity: Method (b)>
(Production of Cellulose-Containing Raw Material Having Lowered Crystallinity)

The cellulose-containing raw material having a lowered crystallinity is the same as that described in <(3-1-i) Production of C-HPC using cellulose-containing raw material having lowered crystallinity>.

From the viewpoint of improving the productivity of the cellulose-containing raw material having a lowered crystallinity, preferred is one to be produced by grinding a high-crystalline cellulose-containing raw material, for example, wood pulp.

The degree of crystallinity of the cellulose-containing raw material having a lowered crystallinity is preferably from 10 to 50%, more preferably from 10 to 40%, even more preferably from 10 to 30%, from the viewpoint of increasing the reactivity between the alkali cellulose to be mentioned below and the cationizing agent and propylene oxide and from the viewpoint of increasing the degree of polymerization of the cellulose-containing raw material.

(Treatment of Cellulose-Containing Raw Material Having a Lowered Crystallinity to Give Alkali Cellulose)

The cellulose-containing raw material having a lowered crystallinity is mixed with a base and water to give an alkali cellulose.

The base includes alkali metal hydroxides such as sodium hydroxide, potassium hydroxide, lithium hydroxide, etc.; alkaline earth metal hydroxides such as magnesium hydroxide, calcium hydroxide, etc.; tertiary amines such as trimethylamine, triethylamine, triethylenediamine, etc. Of those, preferred is an alkali metal hydroxide or an alkaline earth metal hydroxide. Even more preferred is an alkali metal hydroxide; and still more preferred is sodium hydroxide or potassium hydroxide. One or more different types of these bases may be used here either singly or as combined.

The amount of the base is preferably from 0.6 to 1.5 mols per mol of AGU that constitutes the cellulose in the cellulose-containing raw material, more preferably from 0.7 to 1.3 mols, even more preferably from 0.8 to 1.2 mols, from the viewpoint of increasing the yield of the alkali cellulose and from the viewpoint of improving the reactivity of the alkali cellulose and the cationizing agent and propylene oxide to be mentioned below.

The amount of water to be added is preferably from 20 to 100% by mass of the cellulose in the cellulose-containing raw material, more preferably from 25 to 70% by mass, even more preferably from 30 to 60% by mass, from the viewpoint of increasing the yield of the alkali cellulose and from the viewpoint of improving the reactivity of the alkali cellulose and the cationizing agent and propylene oxide to be mentioned below.

The method of mixing the cellulose-containing raw material having lowered crystallinity with a base and water is not specifically defined, but from the viewpoint of increasing the productivity, it is desirable to add a base and water to the cellulose-containing raw material having lowered crystallinity. Regarding the addition mode, all the components may be added at a time to the reactor, or divided portions thereof may be added thereto intermittently. As the case may be, a base and water may be previously mixed, and the resulting mixture may be sprayed onto the cellulose-containing raw material.

Not specifically defined, the mixing apparatus may be any one where a base can be dispersed in the cellulose-containing raw material. For example, there are mentioned various mixing machines such as a ribbon-type mixer, a paddle-type mixer, a conical planetary screw-type mixer, a kneader, etc. Of those, more preferred is a horizontal screw-type paddle mixer, concretely a Ledige mixer that is a horizontal screw-type paddle mixer having chopper paddles.

After the cellulose-containing raw material having lowered crystallinity has been mixed with a base and water, the resulting mixture is preferably ripened from the viewpoint of increasing the speed of producing the alkali cellulose. The ripening temperature is preferably from 35 to 90° C., more preferably from 38 to 80° C., even more preferably from 40 to 70° C. The ripening time is preferably from 0.1 to 24 hours, more preferably from 0.5 to 12 hours, even more preferably from 1 to 6 hours.

The change from the cellulose-containing raw material to alkali cellulose can be confirmed through X-ray crystal diffractometry.
(Hydroxypropylation of Alkali Cellulose)

Preferred embodiments of the amount of propylene oxide, the type of catalyst, the amount of catalyst and the reaction condition in hydroxypropylation of alkali cellulose are the same as those described in (hydroxypropylation) in the above-mentioned <(3-1-i) Production of C-HPC using cellulose-containing raw material having lowered crystallinity>.
(Cationization of Hydroxypropyl Cellulose)

Preferred embodiments of the type of the cationizing agent, the amount of the cationizing agent, the type of the catalyst, the amount of the catalyst and the reaction condition in cationization of hydroxypropyl cellulose are the same as those described in (cationization) in the above-mentioned <(3-1-i) Production of C-HPC using cellulose-containing raw material having lowered crystallinity>.

<(3-2-ii) Production of C-HPC Using Cellulose-Containing Raw Material Having High Crystallinity: Method (c)>
(Treatment of Cellulose-Containing Raw Material to Give Alkali Cellulose)

The cellulose-containing raw material is treated in a grinder along with a base and substantially with no water therein to give a ground cellulose/base mixture, which is then mixed with water to give an alkali cellulose.

Preferred embodiments of the type, the shape, the degree of crystallinity and the mean degree of polymerization of the cellulose-containing raw material are the same as those in the section of (cationization of high-crystalline cellulose-containing raw material) in the above-mentioned Method (a).

Preferred embodiments of the type of the base compound, and the amount of the base are the same as those in the section of (treatment into alkali cellulose) in the above-mentioned Method (b).

From the viewpoint of reducing the water content during grinding, preferably, the base is mixed with the cellulose material in the absence of water therein.

Preferably, the treatment in the grinder is carried out substantially in the absence of water therein. Specifically, from the viewpoint of improving the grinding efficiency and the productivity such as the easiness in water removal, the water content in the system is preferably at most 10% by mass relative to the cellulose-containing raw material, more preferably from 0.01 to 8% by mass, even more preferably from 0.1 to 6% by mass, further more preferably from 1 to 5% by mass.

Preferred embodiments of the type of the grinder and the grinding condition are the same as those described in the section of (production of cellulose-containing raw material having lowered crystallinity) in the above-mentioned <(3-1-i) Production of C-HPC using cellulose-containing raw material having lowered crystallinity>.

From the viewpoint of increasing the speed in producing alkali cellulose, from the viewpoint of increasing the yield of alkali cellulose, and from the viewpoint of preventing the mean degree of polymerization of cellulose from lowering, preferably, the cellulose/base mixture is ground so that the mean particle size of the cellulose in the ground cellulose/base mixture could be from 10 to 150 μm, more preferably from 20 to 130 μm, even more preferably from 40 to 100 μm, still more preferably from 50 to 80 μm. The mean particle size of the ground cellulose/base mixture may be determined according to the method described in the section of Examples.

From the viewpoint of increasing the yield of alkali cellulose, and from the viewpoint of enhancing the reactivity between alkali cellulose and the cationizing agent and propylene oxide to be mentioned below, preferably, water is mixed with the ground cellulose/base mixture in such a manner that the water content in the ground cellulose/base mixture could be from 30 to 100% by mass relative to the cellulose in the cellulose-containing raw material, more preferably from 35 to 70% by mass, even more preferably from 40 to 60% by mass.

(Hydroxypropylation of Alkali Cellulose)

Preferred embodiments of the amount of propylene oxide, the type of the catalyst, the amount of the catalyst and the reaction condition in hydroxypropylation of alkali cellulose are the same as those described in the section of (hydroxypropylation) in the above-mentioned <(3-1-i) Production of C-HPC using cellulose-containing raw material having lowered crystallinity>.

(Cationization of Hydroxypropyl Cellulose)

Preferred embodiments of the type of the cationizing agent, the amount of the cationizing agent, the type of the catalyst, the amount of the catalyst and the reaction condition in cationization of hydroxypropyl cellulose are the same as those described in the section of (cationization) in the above-mentioned <(3-1-i) Production of C-HPC using cellulose-containing raw material having lowered crystallinity>.

The reaction sequence of the hydroxypropylation and the cationization in the above-mentioned methods (b) and (c) may be transposed, but from the viewpoint of increasing the degree of substitution with cationized ethyleneoxy group, the reaction order is the hydroxypropylation first followed by the cationization.

The production method for C-HPC for use in the present invention is preferably the method (method (a) mentioned below) of <(3-1-ii) Production of C-HPC using cellulose-containing raw material having high crystallinity> in the above-mentioned method (3-1), or the method (method (b) or (c) mentioned below) described in (3-2), from the viewpoint that the skin cleanser composition of the present invention can provide an excellent frictional resistance feeling during rinsing after washing and can give an excellent silky feeling with moisturization to the skin after drying.

Concretely, C-HPC is preferably one obtained according to the method including the following steps (a-1) to (a-3), or the method including the following step (a-4) and (a-5), or the method including the following steps (b-1) to (b-4), or the method including the following steps (c-1) to (c-4), from the viewpoint of providing an excellent frictional resistance feeling during rinsing after washing and giving an excellent silky feeling with moisturization to the skin after drying, and is more preferably one obtained according to the method (a) mentioned below and including the steps (a-1) to (a-3), or one obtained according to the method (b) mentioned below and including the steps (b-1) to (b-4), or one obtained according to the method (c) mentioned below and including the steps (c-1) to (c-4).

Method (a):

Step (a-1): a step of adding a cationizing agent to a cellulose-containing raw material and processing it with a grinder.

Step (a-2): a step of adding a base to the grinder-processed product obtained in the step (a-1), and while processing it with a grinder, reacting the cellulose-containing raw material and the cationizing agent to give a cationized cellulose.

Step (a-3): a step of reacting the cationized cellulose obtained in the step (a-2) with propylene oxide to give a cationized hydroxypropyl cellulose (A).

Step (a-4): a step of adding a base to a cellulose-containing raw material and processing it with a grinder for crystallinity reduction, and thereafter while a cationizing agent is added thereto and processing it with a grinder for crystallinity reduction, reacting the cellulose-containing raw material and the cationizing agent to give a cationized cellulose.

Step (a-5): a step of reacting the cationized cellulose obtained in the step (a-4) with propylene oxide to give a cationized hydroxypropyl cellulose.

Method (b):

Step (b-1): a step of processing a cellulose-containing raw material with a grinder to give a cellulose-containing raw material that contains a cellulose having a degree of crystallinity of from 10 to 50%.

Step (b-2): a step of adding to the cellulose-containing raw material obtained in the step (b-1), a base in an amount of from 0.6 to 1.5 molar times per mol of AGU that constitutes the cellulose in the cellulose-containing raw material, and water in an amount of from 20 to 100% by mass relative to the cellulose in the cellulose-containing raw material, thereby giving an alkali cellulose.

Step (b-3): a step of reacting the alkali cellulose obtained in the step (b-2) and propylene oxide to give a hydroxypropyl cellulose.

Step (b-4): a step of reacting the hydroxypropyl cellulose obtained in the step (b-3) with a cationizing agent to give the cationized hydroxypropyl cellulose (A).

Method (c):

Step (c-1): a step of processing a mixture of a cellulose-containing raw material and a base in an amount of from 0.6 to 1.5 molar times per mol of AGU that constitutes the cellulose in the cellulose-containing raw material, with a grinder under the condition where the water content in the cellulose-containing raw material is at most 10% by weight relative to the cellulose therein, thereby giving a ground cellulose/base mixture in which the mean particle size of the cellulose is from 10 to 150 μm.

Step (c-2): a step of adding water to the ground cellulose/base mixture obtained in the step (c-1) to thereby control the water content in the ground cellulose/base mixture to be from 30 to 100% by mass relative to the cellulose in the cellulose-containing raw material used in the step (c-1), thereby giving an alkali cellulose.

Step (c-3): a step of reacting the alkali cellulose obtained in the step (c-2) with propylene oxide to give a hydroxypropyl cellulose.

Step (c-4): a step of reacting the hydroxypropyl cellulose obtained in the step (c-3) with a cationizing agent to give a cationized hydroxypropyl cellulose (A).

[Surfactant (B)]

The skin cleanser composition of the present invention contains a surfactant (B). The surfactant (B) includes an anionic surfactant (B'), a nonionic surfactant and an ampholytic surfactant, and from the viewpoint of the cleansing performance and the frictional resistance feeling during rinsing thereof, preferred are an anionic surfactant (B'), a nonionic surfactant and an ampholytic surfactant, and more preferred is an anionic surfactant (B').

(Anionic Surfactant (B'))

As specific examples of the anionic surfactant (B'), preferred are sulfate ester salts, sulfonate salts, carboxylate salts, phosphate ester salts and amino acid salts.

Concretely, there are mentioned sulfate ester salts such as alkyl sulfate salts, alkenyl sulfate salts, polyoxyalkylene alkyl ether sulfate salts, polyoxyalkylene alkenyl ether sulfate salts, polyoxyalkylene alkylphenyl ether sulfate salts, etc.; sulfonate salts such as alkyl sulfosuccinates salts, polyoxyalkylene alkyl sulfosuccinate salts, alkane sulfonic acids, acylisethionic acid salts, sulfonic acid salts such as acylmethyl taurate, etc.; carboxylic acid salts such as higher fatty acid salts, polyoxyalkylene alkylether acetate salts, etc.; phosphate ester salts such as alkyl phosphate salts, polyoxyalkylene alkylether phosphate salts, etc.; amino acid salts such as acylglutamic acid salts, glycine derivatives, alanine derivatives, arginine derivatives, etc.

Of those, preferred are alkyl sulfate salts such as sodium lauryl sulfate, etc.; polyoxyethylene alkylether sulfate salts such as sodium polyoxyethylene lauryl ether sulfate, etc.; higher fatty acid salts such as potassium laurate, etc.; polyoxyethylene alkyl ether acetate salts such as sodium polyoxyethylene lauryl ether acetate, etc.; alkyl sulfosuccinate salts such as sodium polyoxyethylene lauryl ether sulfosuccinate, etc.; acylglutamic acid salts such as sodium N-acryl-L-glutamate, etc.; acylsarcosine salts, acylglycine salts, acylisethionic acid salts, acylmethyl taurate and alkylphosphate salts, from the viewpoint of the cleansing capability of the skin cleanser composition of the present invention, the foam amount and the foam quality during washing and the frictional resistance feeling during rinsing. More preferred are sodium lauryl sulfate, ammonium polyoxyethylene (1) lauryl ether sulfate (ammonium laureth-1 sulfate), sodium polyoxyethylene (2) lauryl ether sulfate (sodium laureth-2 sulfate), potassium laurate, sodium polyoxyethylene (4.5) lauryl ether acetate (sodium laureth-4.5 acetate), sodium polyoxyethylene lauryl ether (2) sulfosuccinates (sodium laureth-2 sulfosuccinate), and sodium cocoyl glutamate.

(Nonionic Surfactant)

The nonionic surfactant includes polyalkylene glycol-type surfactants such as polyoxyalkylene sorbitan fatty acid esters, polyoxyalkylene sorbitol fatty acid esters, polyoxyalkylene glycerin fatty acid esters, polyoxyalkylene fatty acid esters, polyoxyalkylene alkyl ethers, polyoxyalkylene alkyl phenyl ethers, polyoxyalkylene (hardened) castor oil, etc.; polyalcohol-type surfactants such as sucrose fatty acid esters, polyglycerin alkyl ethers, polyglycerin fatty acid esters, alkyl glycosides, etc.; and fatty acid alkanolamides.

Of those, preferred are polyoxyalkylene alkyl ethers, polyoxyethylene fatty acid esters, polyoxyethylene sorbitan fatty acid esters, polyoxyethylene hardened castor oil, alkyl glycosides and fatty acid alkanolamides, from the viewpoint of the cleansing capability, the foam amount and the foam quality during washing and the frictional resistance feeling during rinsing.

As the polyoxyalkylene alkyl ethers, preferred are polyoxyethylene alkyl ethers such as polyoxyethylene lauryl ether, etc., as well as polyoxypropylene alkyl ethers, polyoxyethylene/polyoxypropylene alkyl ethers.

As the alkyl glycosides, preferred are polysaccharides having a hydrophobic group via a glycoside bond and having a degree of polymerization of from 1 to 20. The degree of polymerization of the polysaccharides is more preferably from 1 to 10, even more preferably from 1 to 5.

The sugar to constitute the polysaccharides is preferably glucose or galactose, and is more preferably glucose. Concretely, preferred are alkyl glucosides such as decyl glucoside, lauryl glucoside, etc.

The fatty acid alkanolamides may be any of fatty acid monoalkanolamides or fatty acid dialkanolamides, but preferred are those having a hydroxyalkyl group with 2 or 3 carbon atoms. More preferred are cocoyl fatty acid monoethanolamide, and cocoyl fatty acid N-methylmonoethanolamide.

(Ampholytic Surfactant)

As the ampholytic surfactant, preferred are betaine-type surfactants and amine oxide-type surfactants such as alkyldimethylamine oxides, etc., from the viewpoint of the foam amount and the foam quality during washing with the skin cleanser composition of the present invention and of the frictional resistance feeling during rinsing.

Of those, as the betaine-type surfactants, more preferred are imidazoline-type betaines such as alkylcarboxymethylhydroxyethylimidazolium betaines, etc.; betaine-type surfactants such as alkyldimethylaminoacetate betaines, cocoyl fatty acid amide propylbetaines, sulfobetaines, etc.; and amine oxide-type surfactants such as alkyldimethylamine oxides, etc. Even more preferred are alkylcarboxymethylhydroxyethylimidazolium betaines, cocoyl fatty acid amide propylbetaines, alkylhydroxysulfobetaines, alkylsulfobetaines, fatty acid amide propylhydroxysulfobetaines and fatty acid amide propylslfobetaines; and even more preferred are cocoyl fatty acid amide propylbetaines.

From the viewpoint of the cleansing capability of the skin cleanser composition of the present invention, the foam amount and the foam quality during washing and the frictional resistance feeling during rinsing, the anionic, nonionic and ampholytic surfactants preferably have an alkyl group or an alkenyl group with from 8 to 20 carbon atoms as the hydrophobic moiety therein, more preferably an alkyl group or an alkenyl group with from 10 to 16 carbon atoms.

The content of the surfactant in the skin cleanser composition of the present invention is preferably from 1 to 80% by mass, more preferably from 3 to 50% by mass, even more preferably from 5 to 30% by mass, still more preferably from 7 to 20% by mass, from the viewpoint of the cleansing capability and the frictional resistance feeling during rinsing.

(Oil (C))

Preferably, the skin cleanser composition of the present invention contains an oil (C). The oil (C) for use herein may be any oily component generally usable in medicines, quasi-drugs, cosmetics, toiletries, sundries, etc. The oil (C) is preferably a hardly water-soluble or water-insoluble oil of which the amount of dissolution in 100 g of water at 20° C. is from 0 to 1 g. The oil (C) in the skin cleanser composition of the present invention can give a moisturization feeling to the skin after washing and drying.

Specific examples of the oil (C) include (i) ester oils, (ii) ether oils, (iii) hydrocarbon oils, (iv) higher alcohols, (v) silicone oils, etc. Of those, preferred are (i) ester oils, from the viewpoint of the foamability during washing and the moisturization feeling given to the skin after drying; and more preferred are vegetable ester oils from the viewpoint of reducing skin irritation.

As the ester oils (i), preferred are ester oils represented by the following general formula (4) or (5), and hydrophobic carboxylate esters of dipentaerythritol, from the viewpoint of the foamability during washing and the moisturization feeling given to the skin after drying.

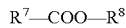

$$R^7\text{—COO—}R^8 \tag{4}$$

(In the formula, $R^7$ represents a linear or branched alkyl group having from 8 to 22 carbon atoms. $R^8$ represents a linear or branched alkyl or alkenyl group having from 1 to 22 carbon atoms.)

In the general formula (4), the carbon number of $R^7$ is preferably from 10 to 20, more preferably from 12 to 18, from the viewpoint of the foamability during washing and the moisturization feeling given to the skin after drying. From the same viewpoint, the carbon number of $R^8$ is preferably from 1 to 20, more preferably from 1 to 18. $R^8$ is more preferably a linear or branched alkyl or alkenyl group having from 1 to 18 carbon atoms and optionally interrupted by a propyleneoxy group or a phenyl group.

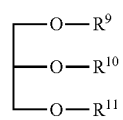

(5)

(In the formula, $R^9$, $R^{10}$ and $R^{11}$ each independently represent a hydrogen atom or a group represented by the following general formula (6), but all of these are not hydrogen atoms at the same time.)

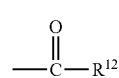

(6)

(In the formula, $R^{12}$ represents a linear or branched alkyl or alkenyl group having from 8 to 22 carbon atoms, which may be interrupted by a carboxylate ester group and which may be substituted with a hydroxyl group.)

In the general formula (6), the carbon number of $R^{12}$ is preferably from 8 to 20, more preferably from 8 to 18 from the viewpoint of the foamability during washing and the moisturization feeling given to the skin after drying.

Specific examples of the ester oils represented by the general formula (4) or (5) include vegetable ester oils such as castor oil, cacao oil, mink oil, avocado oil, olive oil, sunflower oil, camellia oil, apricot oil, almond oil, wheat germ oil, theobroma grandiflorum seed oil, grape seed oil, babassu oil, jojoba oil, macadamia nut oil, tea seed oil, shea butter oil, camellia reticulata oil, meadowfoam oil, bees wax, etc.; as well as lanolin, reduced lanolin, lanolin fatty acid octyldodecyl, caprylyl eicosenoate, dimer acid diisopropyl, myristyl 2-ethylhexanoate, cetyl 2-ethylhexanoate, stearyl 2-ethylhexanoate, octyloctanoate, lauryl octanoate, myristyl octanoate, isocetyl octanoate, octyl propylheptanoate, cetostearyl isononanoate, isononyl isononanoate, isotridecyl isononanoate, methyl laurate, hexyl laurate, octyl laurate, isopropyl myristate, octyl myristate, myristyl myristate, octyldodecyl myristate, isopropyl palmitate, 2-ethylhexyl palmitate, octyl palmitate, cetyl palmitate, methyl oleate, oleyl oleate, decyl oleate, isobutyl oleate, methyl stearate, 2-ethylhexyl stearate, octyl stearate, isocetyl stearate, stearyl stearate, butyl stearate, isotridecyl stearate, isopropyl isostearate, isocetyl isostearate, isostearyl isostearate, propylene glycol isostearate, 2-ethylhexyl hydroxystearate, oleyl erucate, propane diol dicaprylate, diisopropyl adipate, dimethoxyethyl succinate, 2-ethylhexyl succinate, poly-soybean fatty acid sucrose, polysucrose behenate, sucrose tetraisostearate, glyceryl tribehanate, hydroxyalkyl (C16-18) hydroxydimer dilinoleyl ether, triisostearin, pentaerythrityl tetrastearate, etc.

Of those, preferred are sunflower oil, avocado oil, camellia oil, macadamia nut oil, shea butter oil, octyl laurate, octyl myristate, octyldodecylmyristate, isopropyl myristate, myristyl myristate, isopropyl palmitate, 2-ethylhexyl palmitate, octyl palmitate, cetyl palmitate, methyl stearate, 2-ethylhexyl stearate, octyl stearate, isocetyl stearate, stearyl stearate, butyl stearate and tridecyl stearate, from the viewpoint of the foamability during washing with the skin cleanser composition of the present invention and the moisturization feeling given to the skin after drying. More preferred is at least one selected from sunflower oil, avocado oil, camellia oil, macadamia nut oil, shea butter oil, octyl laurate, octyl myristate, myristyl myristate, isopropyl palmitate, octyl palmitate, cetyl palmitate, octyl stearate, isocetyl stearate, stearyl stearate, isostearyl stearate and isostearyl isostearate; and even more preferred is at least one selected from sunflower oil, avocado oil, camellia oil, macadamia nut oil and shea butter oil.

Specific examples of the ether oils (ii) include polyoxypropylene hexyl ether, polyoxypropylene octyl ether, polyoxypropylene 2-ethylhexyl ether, polyoxypropylene decyl ether, polyoxypropylene isodecyl ether, polyoxypropylene lauryl ether, polyoxypropylene myristyl ether, polyoxypropylene palmityl ether, polyoxypropylene cetyl ether, polyoxypropylene stearyl ether, polyoxypropylene isostearyl ether polyoxypropylene octyldecyl ether, polyoxypropylene eicosyl ether, polyoxypropylene behenyl ether and the like, in which the mean addition molar number of the propyleneoxy groups is from 3 to 15.

Specific Examples of the hydrocarbon oils (iii) include squalene, squalane, liquid paraffin, liquid isoparaffin, heavy liquid isoparaffin, α-olefin oligomer, cycloparaffin, polybutene, vaseline, paraffin wax, microcrystalline wax, polyethylene wax, ceresin. From the viewpoint of giving moisturization feeling to the skin after drying, preferred are squalane, squalene, liquid paraffin and paraffin wax; and more preferred is at least one selected from squalane and liquid paraffin.

Specific examples of the higher alcohols (iv) include hexyl alcohol, 2-ethylhexyl alcohol, octyl alcohol, decyl alcohol, isodecyl alcohol, lauryl alcohol, myristyl alcohol, palmityl alcohol, cetyl alcohol, stearyl alcohol, isostearyl alcohol, 2-octyldodecanol, eicosyl alcohol, behenyl alcohol.

As specific examples of the silicone oils (v), preferred is at least one selected from dimethylpolysiloxane, dimethiconol, and amino-modified silicone, polyether-modified silicone, glyceryl-modified silicone, amino derivative silicone, silicone wax and silicone elastomer, from the viewpoint of the feeling in application to skin.

One alone or two or more different types of these oils (C) may be used here either singly or as combined.

The content of the oil (C) in the skin cleanser composition of the present invention is from 1 to 40% by mass, preferably from 3 to 38% by mass, even more preferably from 5 to 35% by mass, further more preferably from 10 to 30% by mass, from the viewpoint of the moisturization feeling given to the skin after drying.

In the skin cleanser composition of the present invention, the proportion of the oil (C) to C-HPC (A) is, as a ratio by mass of [oil (C)/C-HPC (A)], preferably from 1 to 400, more preferably from 5 to 200, even more preferably from 10 to 100, further more preferably from 15 to 50, from the viewpoint of the foamability during washing and the moisturization feeling given to the skin after drying.

[Skin Cleanser Composition]

In the skin cleanser composition of the present invention, the proportion of the surfactant (B) to C-HPC is, as a ratio by mass of [C-HPC/surfactant], preferably from 0.0001 to 1, more preferably from 0.001 to 0.5, even more preferably from 0.005 to 0.1, further more preferably from 0.01 to 0.05, from the viewpoint of improving the frictional resistance feeling during rinsing and the silky feeling with moisturization after drying.

The skin cleanser composition of the present invention may suitably contain any other components generally used in ordinary skin cleansers, in accordance with the intended use and within a range not detracting from the advantageous effects of the present invention. The optional components include feeling improver, thickener, surfactant, oil, vitamins, microbicide, antiinflammatory agent, fragrance, UV absorbent, visible light absorbent, chelate agent, antioxidant, colorant, preservative, pH regulator, viscosity regulator, pearly gloss agent, moisturizer, etc.

The skin cleanser composition of the present invention can be produced according to an ordinary method. The forms of the composition are not specifically defined. The composition can be in any form of liquid, foam, paste, cream, solid, powder, etc. From the viewpoint of the convenience in use, the composition is preferably in the form of liquid, a paste or cream, but is more preferably a liquid.

When the composition is formed as a liquid, water, polyethylene glycol, ethanol or the like is preferably used as the liquid medium. When water is added to the composition, its amount is preferably from 10 to 99% by mass of the entire composition, more preferably from 30 to 95% by mass, even more preferably from 50 to 90% by mass, further more preferably from 70 to 85% by mass.

Preferably, the skin cleanser composition of the present invention has a pH of from 3 to 11, more preferably a pH of from 4 to 10, even more preferably a pH of from 4.5 to 7, since the composition irritates little the skin, keeps excellent cleansing power and is excellent in frictional resistance feeling during rinsing. In the present invention, the pH of the skin cleanser composition may be measured by diluting the composition 20 times with ion-exchanged water added thereto to give an aqueous 5 mass % solution, and its pH is measured at 25° C. with a pH meter (Horiba Seisaku-sho's Model F-22).

[Method for Producing Skin Cleanser Composition]

The method for producing the skin cleanser composition of the present invention is a method for producing a skin cleanser composition containing a cationized hydroxypropyl cellulose (A) and a surfactant (B), wherein the cationized hydroxypropyl cellulose (A) has an anhydroglucose-derived main chain represented by the above-mentioned general formula (1), and has a degree of substitution with cationized ethyleneoxy group of from 0.01 to 3.0 and a degree of substitution with propyleneoxy group of from 0.01 to 2.9; and the method includes the above-mentioned steps (a-1) to (a-3), the above-mentioned steps (a-4) and (a-5), the above-mentioned steps (b-1) to (b-4) or the above-mentioned steps (c-1) to (c-4).

From the viewpoint of providing an excellent frictional resistance feeling during rinsing after washing and giving an excellent silky feeling with moisturization to the skin after drying, the production method of the present invention preferably includes the above-mentioned steps (a-1) to (a-3), the above-mentioned steps (b-1) to (b-4) or the above-mentioned steps (c-1) to (c-4); and from the viewpoint of preventing the molecular weight of C-HPC from lowering, the production method includes more preferably the above-mentioned steps (b-1) to (b-4) or the above-mentioned steps (c-1) to (c-4).

[Method for Producing Skin Cleanser Composition Containing Oil (C)]

From the viewpoint of improving the foamability during washing and the moisturization feeling after drying, the skin cleanser composition containing an oil (C) is preferably produced according to the production method containing the following steps (I) to (III). Consequently, the present invention also provides the method for producing the above-mentioned skin cleanser composition that contains the following steps (I) to (III).

Step (I): a step of mixing a cationized hydroxypropyl cellulose (A) and an anionic surfactant (B') to prepare a mixture, Step (II): a step of mixing the mixture obtained in the step (I) and an oil (C) to prepare an emulsion, Step (III): a step of mixing the emulsion obtained in the step (II) with a surfactant (B) and water to give a skin cleanser composition.

(Step (I))

The step (I) is a step of mixing a cationized hydroxypropyl cellulose (A) and an anionic surfactant (B'). According to the step (I), it is considered that a complex of the cationized hydroxypropyl cellulose (A) and the anionic surfactant (B') can be formed efficiently.

In the step (I), the method of mixing C-HPC (A) and the anionic surfactant (B') is not specifically defined. Preferably, after an aqueous solution of C-HPC (A) has been prepared, it is mixed with an anionic surfactant (B'). From the viewpoint of efficiently forming the complex of C-HPC (A) and the anionic surfactant (B'), the concentration of the aqueous C-HPC solution is preferably from 0.01 to 20.0% by mass, more preferably from 0.1 to 15.0% by mass, even more preferably from 1.0 to 10.0% by mass.

The content of C-HPC (A) in the mixture in the step (I) is preferably from 0.01 to 10.0% by mass, more preferably from 0.05 to 4.0% by mass, from the viewpoint of the foamability during washing and the ability to efficiently leave the oil on the skin after drying to give a moisturization feeling thereto. From the same viewpoint as above, the content of the anionic surfactant (B') in the mixture is preferably from 0.01 to 20.0% by mass, more preferably from 0.05 to 10.0% by mass.

Also from the same viewpoint as above, the ratio by mass of the anionic surfactant (B') to C-HPC (A) [anionic surfactant (B')/C-HPC (A)] in the step (I) is preferably from 0.01 to 1.0, more preferably from 0.03 to 1.0, even more preferably from 0.05 to 0.5.

The temperature in mixing C-HPC (A) and the anionic surfactant (B') is, from the viewpoint of providing a uniform complex, preferably from 10 to 50° C., more preferably from 15 to 40° C., even more preferably from 20 to 30° C. Also from the same viewpoint as above, the stirring speed in mixing C-HPC (A) and the anionic surfactant (B') is preferably from 50 to 1000 rpm, more preferably from 100 to 800 rpm, even more preferably from 150 to 600 rpm, further more preferably from 200 to 400 rpm.

The mixing time in the step (I) is preferably from 1 to 60 minutes, more preferably from 5 to 30 minutes.

(Step (II))

The step (II) is a step of mixing the mixture obtained in the step (I) and an oil (C) to obtain an emulsion. It is considered that an emulsion can be formed efficiently in the step (II).

The content of the oil (C) in the emulsion is preferably from 5 to 99% by mass, more preferably from 20 to 97% by mass, even more preferably from 30 to 95% by mass, from the viewpoint of the foamability during washing and the ability to efficiently leave the oil on the skin after drying to give a moisturization feeling thereto.

From the viewpoint of providing an uniform emulsion, preferably, the above-mentioned mixture is mixed with the oil (C) in such a manner that the oil (C) is added to the mixture little by little. The temperature in mixing is, from the same viewpoint as above, preferably from 10 to 50° C., more preferably from 15 to 40° C., even more preferably from 20 to 30° C. Also from the same viewpoint as above, the stirring speed in mixing is preferably from 50 to 3000 rpm, more preferably from 100 to 1000 rpm, even more preferably from 150 to 600 rpm, further more preferably from 200 to 400 rpm.

Also from the same viewpoint as above, the peripheral speed in mixing is preferably from 0.1 to 8 m/sec, more preferably from 0.3 to 3 m/sec, even more preferably from 0.4 to 2 m/sec.

The mixing time in the step (II) is preferably from 1 to 60 minutes, more preferably from 5 to 30 minutes.

(Step (III))

The step (III) is a step of mixing the emulsion obtained in the step (II) with a surfactant (B) and water to give a skin cleanser composition. It is considered that, according to the step (III), there can be produced a skin cleanser composition having the ability to efficiently leave the oil (C) on the skin and capable of giving moisturization feeling to the skin after drying.

The surfactant (B) for use in the step (III) may be any conventional known surfactant, but from the viewpoint of the foamability during washing and the ability to efficiently leave the oil on the skin after drying to give a moisturization feeling thereto, the surfactant (B) is the above-mentioned anionic surfactant (B').

In the step (III), the above-mentioned emulsion is mixed with a surfactant (B) and water. Further, the above-mentioned conventional known additives may be added thereto. The sequence of mixing the emulsion with the surfactant (B), water and the additives is not specifically defined.

From the viewpoint of efficient mixing, the temperature in mixing is preferably from 10 to 90° C., more preferably from 15 to 60° C., even more preferably from 20 to 50° C. However, after the emulsion has been added, it is desirable that the mixture is not heated from the viewpoint of preventing the emulsion from being disintegrated. Specifically, mixing is effected at preferably 10 to 40° C., more preferably 20 to 30° C. Also from the same viewpoint as above, the stirring speed in mixing is preferably from 50 to 2000 rpm, more preferably from 60 to 1000 rpm, even more preferably from 80 to 500 rpm, further more preferably from 100 to 200 rpm.

Also from the same viewpoint as above, the peripheral speed in mixing is preferably from 0.1 to 5 m/sec, more preferably from 0.2 to 3 m/sec, even more preferably from 0.2 to 2 m/sec.

The mixing time in the step (III) is preferably from 1 to 60 minutes, more preferably from 5 to 40 minutes.

The production method containing the above-mentioned steps (I) to (III) efficiently produces the skin cleanser composition of the present invention.

Relative to the above-mentioned embodiments, the present invention discloses the following skin cleanser composition and the following production method for the composition.

[1] A skin cleanser composition containing a cationized hydroxypropyl cellulose (A) and a surfactant (B), wherein the cationized hydroxypropyl cellulose (A) has an anhydroglucose-derived main chain represented by the following general formula (1), and has a degree of substitution with cationized ethyleneoxy group of from 0.01 to 3.0, preferably from 0.1 to 2.7, more preferably from 0.6 to 2.5, and a degree of substitution with propyleneoxy group of from 0.01 to 2.9, preferably from 0.05 to 2.5, more preferably from 0.1 to 1.6:

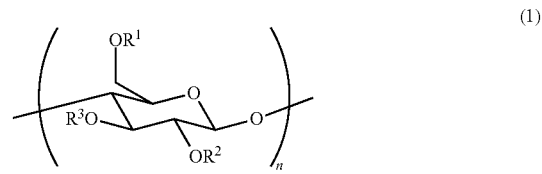

(In the formula, $R^1$, $R^2$ and $R^3$ each independently represent a substituent having a cationized ethyleneoxy group and a propyleneoxy group represented by the following general formula (2); n indicates a mean degree of polymerization of anhydroglucose and is a number of from 20 to 5000, preferably from 50 to 1000, more preferably from 100 to 500.)

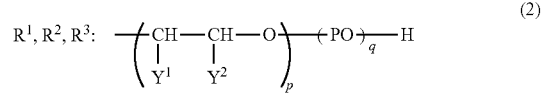

(In the formula, one of $Y^1$ and $Y^2$ is a hydrogen atom and the other is a cationic group represented by the following general formula (3); PO represents a propyleneoxy group; p indicates the number of cationized ethyleneoxy groups ($(-CH(Y^1)-CH(Y^2)-O-)$) in the general formula (2) and q indicates the number of propyleneoxy groups ($-PO-$) therein, each being 0 or a positive integer; in case where both of p and q are not 0, the addition sequence of the cationized ethyleneoxy group and the propyleneoxy group is not defined, and in case where p and/or q are/is 2 or more, a binding form may be any of like a block co-polymer or like a random co-polymer. p is preferably an integer of from 0 to 3, more preferably an integer of from 0 to 2, even more preferably 0 or 1. q is preferably an integer of from 0 to 4, more preferably an integer of from 0 to 2, even more preferably 0 or 1.)

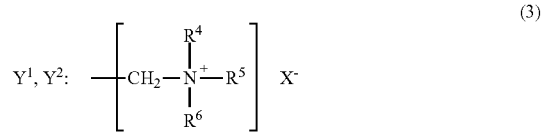

(In the formula, $R^4$, $R^5$ and $R^6$ each independently represent a linear or branched alkyl group having from 1 to 3 carbon atoms, preferably a methyl group or an ethyl group, more preferably a methyl group. $X^-$ represents an anionic group.)

[2] The skin cleanser composition according to the above [1], wherein the content of the cationized hydroxypropyl cellulose (A) is from 0.005 to 10% by mass, preferably from 0.02 to 5% by mass, more preferably from 0.05 to 2% by mass, even more preferably from 0.08 to 1% by mass, further more preferably from 0.1 to 0.5% by mass.

[3] The skin cleanser composition according to the above [1] or [2], wherein the mean degree of polymerization, n, of the anhydroglucose in the general formula (1) is a number of from 100 to 500.

[4] The skin cleanser composition according to any of the above [1] to [3], wherein the surfactant (B) is an anionic surfactant (B').

[5] The skin cleanser composition according to any of the above [1] to [4], wherein the ratio of C-HPC to the surfactant (B) is, as a ratio by mass of [C-HPC/surfactant], from 0.0001 to 1, preferably from 0.001 to 0.5, more preferably from 0.005 to 0.1, even more preferably from 0.01 to 0.05.

[6] The skin cleanser composition according to any of the above [1] to [5], wherein the content of the surfactant in the skin cleanser composition is from 1 to 80% by mass, preferably from 3 to 50% by mass, more preferably from 5 to 30% by mass, even more preferably from 7 to 20% by mass.

[7] The skin cleanser composition according to any of the above [1] to [6], wherein the skin cleanser composition is in any form of liquid, paste or cream.

[8] The skin cleanser composition according to any of the above [1] to [7], which has a pH of from 3 to 11, preferably from 4 to 10, more preferably from 4.5 to 7.

[9] The skin cleanser composition according to any of the above [1] to [8], wherein the cationized hydroxypropyl cellulose (A) is obtained by the following steps (a-1) to (a-3):

Step (a-1): a step of adding a cationizing agent to a cellulose-containing raw material and processing it with a grinder, Step (a-2): a step of adding a base to the grinder-processed product obtained in the step (a-1), and while processing it with a grinder, reacting the cellulose-containing raw material and the cationizing agent to give a cationized cellulose, Step (a-3): a step of reacting the cationized cellulose obtained in the step (a-2) with propylene oxide to give the cationized hydroxypropyl cellulose (A).

[10] The skin cleanser composition according to any of the above [1] to [8], wherein the cationized hydroxypropyl cellulose (A) is obtained by the following steps (b-1) to (b-4):

Step (b-1): a step of processing a cellulose-containing raw material with a grinder to give a cellulose-containing raw material that contains a cellulose having a degree of crystallinity of from 10 to 50%, Step (b-2): a step of adding to the cellulose-containing raw material obtained in the step (b-1), a base in an amount of from 0.6 to 1.5 molar times per mol of the anhydroglucose unit that constitutes the cellulose in the cellulose-containing raw material, and water in an amount of from 20 to 100% by mass relative to the cellulose in the cellulose-containing raw material, thereby giving an alkali cellulose, Step (b-3): a step of reacting the alkali cellulose obtained in the step (b-2) and propylene oxide to give a hydroxypropyl cellulose, Step (b-4): a step of reacting the hydroxypropyl cellulose obtained in the step (b-3) with a cationizing agent to give the cationized hydroxypropyl cellulose (A).

[11] The skin cleanser composition according to any of the above [1] to [8], wherein the cationized hydroxypropyl cellulose (A) is obtained by the following steps (c-1) to (c-4):

Step (c-1): a step of processing a mixture of a cellulose-containing raw material and a base in an amount of from 0.6 to 1.5 molar times per mol of the anhydroglucose unit that constitutes the cellulose in the cellulose-containing raw material, with a grinder under the condition where the water content in the cellulose-containing raw material is at most 10% by weight relative to the cellulose therein, thereby giving a ground cellulose/base mixture in which the mean particle size of the cellulose is from 10 to 150 μm, Step (c-2): a step of adding water to the ground cellulose/base mixture obtained in the step (c-1) to thereby control the water content in the ground cellulose/base mixture to be from 30 to 100% by mass relative to the cellulose in the cellulose-containing raw material used in the step (c-1), thereby giving an alkali cellulose, Step (c-3): a step of reacting the alkali cellulose obtained in the step (c-2) with propylene oxide to give a hydroxypropyl cellulose, Step (c-4): a step of reacting the hydroxypropyl cellulose obtained in the step (c-3) with a cationizing agent to give the cationized hydroxypropyl cellulose (A).

[12] The skin cleanser composition according to any of the above [1] to [11], which further contains an oil (C).

[13] The skin cleanser composition according to the above [12], wherein the content of the oil (C) is from 1 to 40% by mass.

[14] The skin cleanser composition according to the above [12] or [13], wherein the ratio by mass of the oil (C) to the cationized hydroxypropyl cellulose (A) [oil (C)/cationized hydroxypropyl cellulose (A)] is from 1 to 400.

[15] A method for producing the skin cleanser composition of any one of the above [12] to [14], which contains the following steps (I) to (III):

Step (I): a step of mixing a cationized hydroxypropyl cellulose (A) and an anionic surfactant (B') to prepare a mixture, Step (II): a step of mixing the mixture obtained in the step (I) and an oil (C) to prepare an emulsion, Step (III): a step of mixing the emulsion obtained in the step (II) with a surfactant (B) and water to give a skin cleanser composition.

[16] The method for producing the skin cleanser composition according to the above [15], wherein the ratio by mass of the anionic surfactant (B') to the cationized hydroxypropyl cellulose (A) [anionic surfactant (B')/cationized hydroxypropyl cellulose (A)] in the step (I) is from 0.01 to 1.0.

[17] A method for producing a skin cleanser composition containing a cationized hydroxypropyl cellulose (A) and a surfactant (B), wherein the cationized hydroxypropyl cellulose (A) has an anhydroglucose-derived main chain represented by the above-mentioned general formula (1), and has a degree of substitution with cationized ethyleneoxy group of from 0.01 to 3.0 and a degree of substitution with propyleneoxy group of from 0.01 to 2.9; the method including the steps (a-1) to (a-3) in the above [9], the steps (b-1) to (b-4) in the above [10], or the steps (c-1) to (c-4) in the above [11].

[18] Use of the composition of any of the above [1] to [14] as a skin cleanser.

EXAMPLES

Unless otherwise specifically indicated in the following Examples and Comparative Examples, "part" is "part by mass" and "%" is "% by mass". Measurement methods for the physical properties of the samples are as described below.

(1) Measurement of Water Content in Pulp and Powdery Cellulose

The water content in pulp or powdery cellulose was measured, using an IR moisture meter (Kett Electric Laboratory's "FD-610"). The measurement temperature was 120° C., and the point at which the weight change for 30 seconds reached at most 0.1% was referred to as the final point in the measurement.

(2) Calculation of Crystallinity of Pulp and Powdery Cellulose

Using Rigaku's "Rigaku RINT 2500VC X-RAY Diffractometer", the sample was analyzed under the condition mentioned below, and from the peak intensity on the diffraction spectrum, the degree of crystallinity of the sample was calculated according to the above-mentioned math formula (1).

X-ray source: Cu/Kα-radiation, bulb voltage: 40 kV, bulb current: 120 mA
Detection range: 2θ=5 to 45°
Sample: prepared by compressing a pellet having an area of 320 mm² and a thickness of 1 mm
X-ray scanning speed: 10°/min In case where the degree of crystallinity thus measured was a negative value, all such samples were considered to have a crystallinity of 0%.

(3) Measurement of Mean Particle Size of Cellulose in Powdery Cellulose, and Ground Cellulose/Base Mixture The mean particle size of powdery cellulose was determined, using a laser diffraction/scattering particle sizer "LA-920" (by Horiba). The test sample was prepared by adding 0.1 g of a powdery cellulose to 5 mL of water and ultrasonicated for 1 minute to prepare a sample dispersion. The volume-based median diameter was measured at a temperature of 25° C., and was referred to as the mean particle size.

The mean particle size of the cellulose in a ground cellulose/base mixture was determined using the same apparatus. Ethanol was added to a ground cellulose/base mixture and the concentration of the resulting mixture was so controlled that the transmittance thereof could fall within a range of from 70 to 95%. The mixture was ultrasonicated for 1 minute, and NaOH was added thereto to prepare a sample dispersion.

(4) Calculation of Substitution Degree in C-HPC

C-HPC produced in Production Example was purified through a dialytic membrane (molecular weight cut off, 1000), and then the aqueous solution was freeze-dried to give a purified C-HPC. The chlorine content (%) in the thus-obtained pure C-HPC was measured through elementary analysis. The number of the cationic groups contained in C-HPC and the number of the chloride ions that are counter ions were approximated to be the same number, and the amount of the cationized ethyleneoxy groups (—CH($Y^1$)—CH($Y^2$)O—) contained in the unit mass of C-HPC (a (mol/g)) was calculated according to the following math formula (2).

$$a(\text{mol/g}) = \text{chlorine content (\%) obtained through elementary analysis}/(35.5 \times 100) \quad (2)$$

The hydroxypropoxy group content (%) was determined according to the "Method for Analysis of Hydroxypropyl Cellulose" described in Japanese Pharmacopoeia, except that the object to be analyzed here was pure C-HPC but not hydroxypropyl cellulose. According to the math formula (3) mentioned below, the hydroxypropoxy group content [formula weight ($OC_3H_6OH = 75.09$)] (b mol/g) was obtained.

$$b(\text{mol/g}) = \text{hydroxypropoxy group content (\%) obtained through gas chromatography}/(75.09 \times 100) \quad (3)$$

From the thus-obtained a and b and according to the following math formulae (4) and (5), the degree of substitution with cationized ethyleneoxy group (k) and the degree of substitution with propyleneoxy group (m) were calculated.

$$a = k/(162 + k \times K + m \times 58) \quad (4)$$

$$b = m/(162 + k \times K + m \times 58) \quad (5)$$

[In the formulae, k and K each indicate the degree of substitution with cationized ethyleneoxy group and the formula weight; and m indicates the degree of substitution with propyleneoxy group.]

(5) Measurement of Mean Degree of Polymerization (Copper Ammonia Method)
(5-1) Measurement of Viscosity-Average Degree of Polymerization of Pulp and Powdery Cellulose
(i) Preparation of Solution for Measurement 0.5 g of cuprous chloride and 20 to 30 mL of aqueous 25% ammonia were put into a measuring flask (100 mL) and completely dissolved, and then 1.0 g of cupric hydroxide and aqueous 25% ammonia were added thereto to be an amount just before the gauge line. This was stirred for 30 to 40 minutes and completely dissolved. Subsequently, cellulose as accurately weighed was added thereto, and the above-mentioned aqueous ammonia was added thereto up to the gauge line. This was airtightly sealed up, and stirred with a magnetic stirrer for 12 hours for dissolution to thereby prepare a solution for measurement. The amount of the cellulose to be added was varied within a range of from 20 to 500 mg, and solutions for measurement each having a different concentration were prepared.

(ii) Measurement of Viscosity-Average Degree of Polymerization

The solution for measurement (copper ammonia solution) obtained in the above (i) was put into an Ubbelohde viscometer and statically left in a thermostat chamber) (20±0.1 C.°) for 1 hour, and thereafter the flowing-down speed of the liquid was measured. From the flowing-down time (t (sec)) of the copper ammonia solution having a different cellulose concentration (g/dL) and the flowing-down time ($t_0$ (sec)) of a cellulose-free aqueous copper ammonia solution, the reduced viscosity ($\eta_{sp}/c$) at each concentration of the sample was determined according to the following formula:

$$(\eta_{sp}/c) = \{(t - t_0)/t_0\}/c$$

(c: cellulose concentration (g/dL)

Further, the reduced viscosity was extrapolated into c=0 to determine the intrinsic viscosity [η] (dL/g), and according to the following formula, the viscosity-average degree of polymerization (DP) was obtained.

$$DP = 2000 \times [\eta]$$

(5-2) Measurement of Viscosity-Average Degree of Polymerization of C-HPC
(iii) Preparation of Solution for Measurement The solution for measurement was prepared in the same manner as that for the solution for measurement in the above (i), except that a pure C-HPC was used in place of the pure cellulose.

(iv) Measurement of Viscosity-Average Degree of Polymerization

The viscosity-average degree of polymerization was measured in the same manner as that for the solution for the viscosity-average degree of polymerization of the above (ii), except that a cellulose-equivalent concentration (g/dL) was used in place of the concentration of the measurement solution.

The cellulose-equivalent concentration ($c_{cell}$) means the mass (g) of the cellulose skeleton part contained in 1 dL of the measurement solution, and is defined by the following math formula (6).

$$c_{cell} = u \times 162/(162 + k \times K + m \times 58) \quad (6)$$

[In the formula, u indicates the mass (g) of C-HPC that had been accurately weighed in preparation of the measurement solution; and k, K and m have the same meanings as in the above-mentioned math formulae (4) and (5).]

[Degree of Substitution with Propyleneoxy Group (—PO—)]

The degree of substitution with propyleneoxy group was calculated according to the method for analysis of hydroxypropyl cellulose described in Japan Pharmacopoeia, except that the object to be analyzed here was not hydroxypropyl cellulose but the above-mentioned C-HPC that had been purified through dialytic membrane and freeze-dried.

(6) Measurement of 2% Viscosity

With stirring, C-HPC was added to water at 25° C. to prepare an aqueous 2 mass % C-HPC solution. This was put into a viscometer tube with careful attention thereto so that no bubble could come therein, and sealed up with a parafilm, and statically left in a water bath at 30° C. for about 1 hour. Next, a rotor (No. M1 to M4) and a rotation number (6 to 60 rpm) were selected in accordance with the viscosity of the sample, and using a B-type viscometer (Toki Sangyo's Model TVB-10), the value indicated by the viscometer when the rotor was rotated for 1 minute was read out, and the viscosity was thereby calculated.

Production Example 1

Production of C-HPC (1)

(1) Chipping Step

A sheet-like wood pulp (Tembec's Biofloc HV+, having a mean degree of polymerization of 1550, a degree of crystallinity of 74% and a water content of 7.0%) was shredded with a shredder (Meiko Shokai's "MSX2000-IVP440F") into chips of from 3 to 5 mm square.

(2) Cationization Step 18.6 g of an aqueous solution of glycidyltrimethylammonium chloride (by Sakamoto Chemical Industry, water content 20%, purity 90% or more) (hereinafter referred to as "GMAC") serving as a cationizing agent (the amount corresponds to 0.2 mols per mol of AGU of cellulose) was added to 79.6 g of the chip-like pulp obtained in the above (1), and ground with a batch-type vibrational mill (Chuo Kakohki's "MB-1": chamber total volume 3.5 L; 13 rods of SUS304 each having a diameter of 30 mm and a length of 218 mm and having a circular cross section; filling rate 57%) for 12 minutes (frequency 20 Hz, vibrational amplitude 8 mm, temperature 30 to 70° C.) thereby giving a powdery mixture of cellulose and GMAC.

25.4 g (corresponding to 0.2 mols per mol of AGU) of an aqueous 15.5% sodium hydroxide solution was added to the obtained powdery mixture, and ground with the same batch-type vibrational mill under the same condition as above for 60 minutes to give a rough cationized cellulose.

(3) Hydroxypropylation Step 96.6 g of the obtained, rough cationized cellulose (unneutralized, unpurified) was sampled, and the sample thereof was put into a kneader equipped with a reflux tube (Irie Shokai's PNV-1 Model). With stirring, 22.3 g (corresponding to 1 mol per mol of AGU) of propylene oxide (Kanto Chemical's special-grade reagent) was dropwise added to the mixture at 70° C., taking 5 hours, and thereafter ripened at 70° C. for 1 hour. The treatment from propylene oxide addition to ripening was repeated three times (the total amount of the added propylene oxide was 66.9 g), and thereafter 10 g of a sample was sampled out from the reaction product, and neutralized with acetic acid. For the purpose of determining the degree of substitution with propyleneoxy group and with cationized ethyleneoxy group, the neutralized product was dissolved in ion-exchanged water and purified through a dialytic membrane (molecular weight cut off, 1000). The aqueous solution was freeze-dried to give a pure C-HPC (1).

The degree of substitution with cationized ethyleneoxy group and the degree of substitution with propyleneoxy group of the obtained pure C-HPC (1) were calculated to be 0.11 and 1.2, respectively. The mean degree of polymerization was 844. The results are shown in Table 1.

Production Example 2

Production of C-HPC (2)

A pure C-HPC (2) was produced in the same manner as in Production Example 1, except that powdery cellulose (Nippon Paper Chemicals' cellulose powder KC Floc W-400G, having a mean degree of polymerization of 212, a degree of crystallinity of 77%, a water content of 7.0%) was used as the pulp, that the chipping step was omitted, and that the amount of the pulp, GMAC and the base in the cationization step and the amount of the propylene oxide in the hydroxypropylation step were changed as in Table 1. The degree of substitution with cationized ethyleneoxy group and the degree of substitution with propyleneoxy group of the obtained pure C-HPC (2) were calculated to be 0.10 and 1.2, respectively. The mean degree of polymerization was 170. The results are shown in Table 1.

TABLE 1

| | Starting Pulp | | | Cationization Step | | | |
|---|---|---|---|---|---|---|---|
| | Crystallinity (%) | Mean Degree of Polymerization | Chipping Step Apparatus | Amount of Pulp Used (g) | Amount of GMAC added (g) | Grinding Time (min) | Amount of 15.5% NaOH added (g) |
| Production Example 1 | 74 | 1550 | MSX2000-IVP440F | 79.6 | 18.6 | 12 | 25.4 |
| Production Example 2 | 77 | 212 | — | 100.4 | 23.4 | 12 | — |

| | Cationization Step | | Hydroxypropylation Step | | | |
|---|---|---|---|---|---|---|
| | Amount of 24.6% NaOH added (g) | Grinding Time (min) | Amount of Rough Cationized Cellulose Used (g) | Amount of Propylene Oxide Added (g) | Reaction Time (hr) | C-HPC Mean Degree of Polymerization |
| Production Example 1 | — | 60 | 96.6 | 66.9 | 18 | 844 |
| Production Example 2 | 20.0 | 60 | 102.6 | 48.5*1 | *2 | 170 |

*1 Added all at a time.
*2: The reaction was continued until propylene oxide was consumed and the reflux flow stopped.

Production Example 3

Production of C-HPC (3)

(1) Chipping Step

A sheet-like wood pulp (Tembec's Biofloc HV+, having a mean degree of polymerization of 1550, a degree of crystallinity of 74% and a water content of 7.0%) was pelletized with a sheet pelletizer (Horai's "SGG-220") into chips of from 3 to 5 mm square.

(2) Cationization Step (1)

86.0 g of the chip-like pulp obtained in the above (1) was mixed with 20.0 g of GMAC (corresponding to 0.2 mols per mol of AGU) in a mortar, and then put into the batch-type vibrational mill used in Production Example 1. This was ground for 12 minutes (frequency 20 Hz, vibrational amplitude 8 mm, temperature 30 to 70° C.) to give a powdery mixture of cellulose and GMAC.

The obtained powdery mixture was mixed with 8.8 g (corresponding to 0.2 mols per mol of AGU) of an aqueous 48% sodium hydroxide solution in a mortar, and then put into the above-mentioned batch-type vibrational mill. Under the same condition as above, this was ground for 60 minutes to give 114.0 g of a cationized cellulose (i).

(3) Cationization Step (2)

114.0 g of the cationized cellulose (i) obtained in the above (2) was mixed with 32 g of GMAC (corresponding to 0.32 mols per mol of AGU) in a mortar, and then the resulting mixture was put into a 1-L kneader equipped with a reflux tube (Irie Shokai's PNV-1 Model), and with stirring at 50° C. in a nitrogen atmosphere at 50 rpm, this was ripened for 5 hours to give 140.0 g of a cationized cellulose (ii).

(4) Cationization Step (3)

With stirring under reduced pressure (13.3 kPa), the cationized cellulose (ii) obtained in the above was dewatered at 60° C. to have a water content of 10.5% (relative to the starting cellulose), and thereafter 98.0 g of GMAC (corresponding to 1.0 mol per mol of AGU) was added thereto and reacted overnight at 50° C. thereby giving a cationized cellulose (iii).

(5) Hydroxypropylation Step

With stirring under reduced pressure (13.3 kPa), the cationized cellulose (iii) was dewatered at 60° C. to have a water content of 9.3% (relative to the starting cellulose), and then 30.8 g (corresponding to 1.0 mol per mol of AGU) of propylene oxide was added thereto and reacted at 70° C. for 9 hours.

The reaction mixture was neutralized with acetic acid, and dispersed in 2 L of an aqueous 85% isopropyl alcohol solution, and then filtered. This washing treatment was repeated three times. 10 g of a sample was sampled from the product, dissolved in ion-exchanged water, and purified through a dialytic membrane (molecular weight cut off, 1000). The aqueous solution was freeze-dried to give a pure C-HPC (3).

The degree of substitution with cationized ethyleneoxy group and the degree of substitution with propyleneoxy group of the obtained pure C-HPC (3) were calculated to be 0.80 and 0.2, respectively. The mean degree of polymerization was 755.

Production Example 4

Production of C-HPC (4)

A pure C-HPC (4) was produced in the same manner as in Production Example 3, except that the chip-like pulp in Production Example 3 was changed to powdery cellulose (Nippon Paper Chemicals' cellulose powder KC Floc W-400G, having a mean degree of polymerization of 191, a degree of crystallinity of 77%, a water content of 7.0%).

The degree of substitution with cationized ethyleneoxy group and the degree of substitution with propyleneoxy group of the obtained pure C-HPC (4) were calculated to be 0.80 and 0.1, respectively. The mean degree of polymerization was 133.

Production Example 5

Production of C-HPC (5)

(1) Cationization Step (1) (2)

146.0 g of the cationized cellulose (ii) was produced in the same manner as in the cationization step (1) (2) in Production Example 3, except that the chip-like pulp in Production Example 3 was changed to powdery cellulose (Nippon Paper Chemicals' cellulose powder KC Floc W-400G, having a mean degree of polymerization of 191, a degree of crystallinity of 77%, a water content of 7.0%).

(2) Hydroxypropylation Step

With stirring under reduced pressure (13.3 kPa), the cationized cellulose (ii) was dewatered at 60° C. to have a water content of 14% (relative to the starting cellulose), and then 30.8 g (corresponding to 1.0 mol per mol of AGU) of propylene oxide was added thereto and reacted at 70° C. for 9 hours. The reaction mixture was neutralized with acetic acid, and dispersed in 2 L of an aqueous 85% isopropyl alcohol solution, and then filtered. This washing treatment was repeated three times. 10 g of a sample was sampled from the product, dissolved in ion-exchanged water, and purified through a dialytic membrane (molecular weight cut off, 1000). The aqueous solution was freeze-dried to give a pure C-HPC (5).

The degree of substitution with cationized ethyleneoxy group and the degree of substitution with propyleneoxy group of the obtained pure C-HPC (5) were calculated to be 0.30 and 0.3, respectively. The mean degree of polymerization was 216.

Production Example 6

Production of C-HPC (6)

A pure C-HPC (6) was produced by repetition of the same process as in Production Example 5, except that the process from addition of 30.8 g of propylene oxide to reaction at 70° C. in the hydroxypropylation step in Production Example 5 was repeated twice (the total amount of propylene oxide added was 61.6 g, corresponding to 2.0 mols per mol of AGU).

The degree of substitution with cationized ethyleneoxy group and the degree of substitution with propyleneoxy group of the obtained pure C-HPC (6) were calculated to be 0.30 and 1.0, respectively. The mean degree of polymerization was 273.

Production Example 7

Production of C-HPC (7)

A pure C-HPC (7) was produced by repetition of the same process as in Production Example 5, except that the process from addition of 30.8 g of propylene oxide to reaction at 70° C. in the hydroxypropylation step in Production Example 5 was repeated three times (the total amount of propylene oxide added was 92.4 g, corresponding to 3.0 mols per mol of AGU).

The degree of substitution with cationized ethyleneoxy group and the degree of substitution with propyleneoxy group of the obtained pure C-HPC (7) were calculated to be 0.30 and 1.5, respectively. The mean degree of polymerization was 341.

Production Example 8

Production of C-HPC (8)

A pure C-HPC (8) was produced by repetition of the same process as in Production Example 5, except that the process from addition of 30.8 g of propylene oxide to reaction at 70° C. in the hydroxypropylation step in Production Example 5 was repeated four times (the total amount of propylene oxide added was 123.2 g, corresponding to 4.0 mols per mol of AGU).

The degree of substitution with cationized ethyleneoxy group and the degree of substitution with propyleneoxy group of the obtained pure C-HPC (8) were calculated to be 0.30 and 1.8, respectively. The mean degree of polymerization was 371.

Production Example 9

Production of C-HPC (9)

(1) Preparation of Dry Powdery Cellulose

A powdery cellulose (Nippon Paper Chemicals' cellulose powder KC Floc W-400G, having a mean degree of polymerization of 191, a degree of crystallinity of 77%, a water content of 7.0%) was dried under reduced pressure at 50° C. for 12 hours to give a dry powdery cellulose (water content 1.0%).

(2) Cationization Step (1)

60.8 g of GMAC was mixed in 100 g of the obtained powdery cellulose in a mortar, and the put into the vibrational mill described in Production Example 1. This was ground for 12 minutes (frequency 20 Hz, vibrational amplitude 8 mm, temperature 10 to 40° C.) to give a powdery mixture of cellulose and GMAC.

Further, 29.8 g of an aqueous 48% sodium hydroxide solution was put into the vibrational mill. This was again ground in the vibrational mill under the same grinding condition as above for 60 minutes to give a cationized cellulose.

(3) Hydroxypropylation Step 190 g of the cationized cellulose obtained in the above step was put into a kneader, and heated up to 70° C., and with stirring, 18.0 g of propylene oxide was dropwise added thereto. The reaction was continued for 6 hours until the propylene oxide was consumed and the reflux flow stopped.

(4) Cationization Reaction (2)

After the reaction, the mixture was transferred from the kneader to a mortar, and 87.5 g (corresponding to 0.8 mols per mol of AGU) of GMAC was added thereto and mixed at room temperature for 10 minutes. Subsequently, this was returned back to the kneader and reacted therein at 50° C. with stirring for 5 hours to give 295 g of a pale brown crude C-HPC powder. 10.0 g of a sample was sampled from the reaction mixture and neutralized with lactic acid to give a pale brown solid. For the purpose of determining the degree of substitution with propyleneoxy group and with cationized ethyleneoxy group, the product was purified through a dialytic membrane (molecular weight cut off, 1000), and the aqueous solution was freeze-dried to give a pure C-HPC (9).

The degree of substitution with cationized ethyleneoxy group and the degree of substitution with propyleneoxy group of the obtained pure C-HPC (9) were calculated to be 0.84 and 0.2, respectively. The mean degree of polymerization was 241. The results are shown in Table 2.

Production Example 10

Production of C-HPC (10)

A pure C-HPC (10) was produced in the same manner as in Production Example 9, except that the chips were not dried and that condition and the amount of the raw material to be used in the cationization step (1), (2) and the hydroxypropylation step were changed as in Table 2.

The degree of substitution with cationized ethyleneoxy group and the degree of substitution with propyleneoxy group of the obtained pure C-HPC (10) were calculated to be 1.00 and 1.3, respectively. The mean degree of polymerization was 464. The results are shown in Table 2.

TABLE 2

| | Starting Pulp | | | | Cationization Step (1) | | | | |
|---|---|---|---|---|---|---|---|---|---|
| | Degree of Crystallinity (%) | Mean Degree of Polymerization | Water Content (%) | Drying Time (hr) | Amount of Pulp Used (g) | Vibrational Mill | Amount of GMAC Added (g) | Grinding Time (min) | Amount of 48% NaOH Added (g) |
| Production Example 9 | 77 | 191 | 7.0 | 12 | 100 | MB-1 | 60.8 | 12 | 29.8 |
| Production Example 10 | 74 | 1508 | 7.0 | — | 989 | FV-10 | 559 | 12 | — |

| | Cationization Step (1) | | Hydroxypropylation Step | | | Cationization Step (2) | | | | |
|---|---|---|---|---|---|---|---|---|---|---|
| | Amount of Granular NaOH Added (g) | Grinding Time (min) | Amount of Cationized Cellulose Used (g) | Amount of Propylene Oxide Added (g) | Reaction Time (hr) | Crude C-HPC Powder Used (g) | Amount of GMAC Added (g) | Ripening Temperature (° C.) | Ripening Time (hr) | C-HPC Mean Degree of Polymerization |
| Production Example 9 | — | 60 | 190 | 18 | 6 | 208 | 21.9 | 50 | 5 | 241 |
| Production Example 10 | 136.2 | 112 | 95.0 | 35.4 | 7 | 10.6 | 16.2 | 50 | 24 | 464 |

Production Example 11

Production of C-HPC (11)

A pure C-HPC (11) was produced in the same manner as in Production Example 9, except that the process from addition of 87.5 g of GMAC to reaction at 50° C. in the cationization step (2) in Production Example 9 was repeated four times (the total amount of propylene oxide added was 350.0 g, corresponding to 3.0 mols per mol of AGU).

The degree of substitution with cationized ethyleneoxy group and the degree of substitution with propyleneoxy group of the obtained pure C-HPC (11) were calculated to be 1.40 and 0.2, respectively. The mean degree of polymerization was 295.

Production Example 12

Production of C-HPC (12)

A pure C-HPC (12) was produced in the same manner as in Production Example 9, for which the process from addition of 87.5 g of GMAC to reaction at 50° C. in the cationization step (2) in Production Example 9 was repeated seven times (the total amount of propylene oxide added was 612.5 g, corresponding to 5.3 mols per mol of AGU).

The degree of substitution with cationized ethyleneoxy group and the degree of substitution with propyleneoxy group of the obtained pure C-HPC (12) were calculated to be 2.36 and 0.2, respectively. The mean degree of polymerization was 432.

Production Example 13

Production of C-HPC (13)

A sheet-like wood pulp (Borregaard's Blue Bear Ultra Ether, having a mean degree of polymerization of 1532, a degree of crystallinity of 74% and a water content of 7.0%) was shredded with the shredder used in Production Example 1 into chips of from 3 to 5 mm square.

Next, the obtained chip-like pulp was put into a double-screw extruder (Suchiro EPM's "EA-20") at a rate of 2 kg/hr, and powdered therein in one-pass operation at a shear rate of 660 sec-1 and at a screw rotation number of 300 rpm, with applying cooling water thereto from outside.

Next, 100 g of the obtained powdery cellulose was put into a batch-type medium stirring mill (Nippon Coke & Engineering's "Attritor MA01D", media: SUS balls). While cooling water was kept applied to the chamber jacket, this was ground for 7 hours at a temperature falling within a range of from 30 to 70° C. to give a cellulose powder (having a degree of crystallinity of 0%, a viscosity-average degree of polymerization of 556, and a mean particle size of 30 μm).

100 g of the cellulose powder obtained in the above and having a degree of crystallinity of 0% was put into a 1-L kneader (Irie Shokai's PNV-1 Model) equipped with a reflux tube, and then 9.6 g of an aqueous 48% sodium hydroxide solution (corresponding to 0.2 mols per mol of AGU) was dropwise added thereto, and stirred in a nitrogen atmosphere for 3 hours. Subsequently, the kneader was heated up to 70° C., and 15.8 g of diluted GMAC that had been prepared by diluting the GMAC used in Production Example 1 with water to have a water content of 38.5% (corresponding to 0.1 mols per mol of AGU) was dropwise added thereto, taking 1 hour. Subsequently, this was further stirred at 70° C. for 3 hours.

While the obtained cationized cellulose was kept heated at 70° C., 47.0 g of propylene oxide (corresponding to 1.3 mols per mol of AGU) was dropwise added thereto, and reacted for 12 hours until the added propylene oxide was consumed and the reflux flow stopped. 10.0 g of a sample of the reaction product was sampled and neutralized with acetic acid to give a pale brown solid. The product was purified through a dialytic membrane (molecular weight cut off, 1000), and then the aqueous solution was freeze-dried to give a pure C-HPC (13).

The degree of substitution with cationized ethyleneoxy group and the degree of substitution with propyleneoxy group were calculated to be 0.10 and 1.2, respectively. The mean degree of polymerization was 387.

Production Example 14

Production of C-HPC (14)

A sheet-like wood pulp (Tembec's Biofloc HV10A, having a mean degree of polymerization of 1520 and a water content of 7.0%) was shredded with the shredder used in Production Example 1 to give chips of from 3 to 5 mm square, and then ground with a batch-type vibrational mill (Chuo Kakohki's "FV-20", media of SUS rods) to give a powdery cellulose (degree of crystallinity 0%).

99.4 g of the obtained powdery cellulose was put into the kneader equipped with a reflux pipe used in Production Example 1, and with stirring, 9.8 g of an aqueous 48% sodium hydroxide solution (corresponding to 0.2 mols per mol of AGU) and 12.5 g of GMAC (corresponding to 0.1 mols per mol of AGU) were added thereto. This was reacted at 43° C. for 2.2 hours to give a reaction mixture containing a cationized cellulose (having a mean degree of polymerization of 401).

36.4 g of ion-exchanged water was added to the reaction mixture and heated up to 50° C., and 34.2 g of propylene oxide (corresponding to 1.0 mol per mol of AGU) was dropwise added thereto, taking 3 hours, and thereafter this was further ripened for 1 hour. The reaction process from propylene oxide addition to ripening was repeated five times (the total amount of propylene oxide added was 171 g). 10 g was sampled out of the reaction mixture, neutralized with acetic acid, dissolved in ion-exchanged water, and purified through a dialytic membrane (molecular weight cut off, 1000). The aqueous solution was freeze-dried to give a pure C-HPC (14).

The degree of substitution with cationized ethyleneoxy group and the degree of substitution with propyleneoxy group of the obtained pure C-HPC (14) were calculated to be 0.10 and 3.4, respectively. The mean degree of polymerization was 401.

Production Example 15

Production of C-HPC (15)

(1) Chipping Step

A sheet-like wood pulp (Tembec's Biofloc HV+, having a mean degree of polymerization of 1481, a degree of crystallinity of 74% and a water content of 4.6%) was pelletized with a sheet pelletizer (Horai's "SGG-220") into chips of from 3 to 5 mm square.

(2) Alkali Cellulose Production Step 100 g of the chip-like pulp obtained in the above step (1) and 23.6 g of 0.7-mm granular NaOH (corresponding to 1.0 mol per mol of AGU) were put into a batch-type vibrational mill (Chuo Kakohki's "MB-1": chamber total volume 3.5 L; 13 rods of SUS304 each having a diameter of 30 mm and a length of 218 mm and having a circular cross section; filling rate 57%), and ground therein for 15 minutes (frequency 20 Hz, vibrational amplitude 8 mm, temperature 30 to 70° C.). Thus obtained, the ground cellulose/NaOH mixture (mean particle size of cellulose: 65 µm) was transferred into a mortar, and sprayed with 50 g of water. The water content of the ground cellulose/NaOH mixture was 57% relative to the cellulose therein. This was ground with a pestle at 20° C. for 5 minutes to give an alkali cellulose (mean degree of polymerization: 1160).

(3) Hydroxypropylation Step

The alkali cellulose obtained in the above step (2) was put into a kneader equipped with a reflux tube and a dropping funnel (Irie Shokai's PNV-1 Model, capacity 1.0 L), and 51.4 g of propylene oxide (corresponding to 1.5 mols per mol of AGU) was put thereinto and reacted at 50° C. for 4 hours with stirring. For the reaction, propylene oxide was dropwise added taking 3 hours, and the system was then ripened for 1 hour.

(4) Cationization Step 6.3 g of the reaction mixture obtained in the above step (3) was taken into a mortar, and 1.29 g of aqueous 65% 3-chloro-2-hydroxypropyltrimethylammonium chloride solution (by Yokkaichi Gosei) (corresponding to 0.25 mols per mol of AGU) was added thereto and mixed for 5 minutes, and thereafter this was transferred into a 50-ml glass bottle and reacted therein at 50° C. for 7 hours to give a crude C-HPC.

5.0 g of the crude C-HPC powder was sampled and neutralized with lactic acid. For the purpose of determining the degree of substitution with propyleneoxy group and with cationized ethyleneoxy group, the neutralized product was purified through a dialytic membrane (molecular weight cut off, 1000), and then the aqueous solution was freeze-dried to give a pure C-HPC (15).

The degree of substitution with cationized ethyleneoxy group and the degree of substitution with propyleneoxy group of the obtained pure C-HPC (15) were calculated to be 0.14 and 1.0, respectively. The mean degree of polymerization was 759.

Production Example 16

Production of C-HPC (16)

(1) Low-Crystalline Powdery Cellulose Production Step

In the same manner as in Production Example 15(1), pulp chips of from 3 to 5 mm square were obtained. One kg of the obtained chip-like pulp was put into a drier (Advantec Toyo's trade name "VO-402"), and dried therein at 105° C. for 2 hours to give a dry chip-like pulp (water content 0.8%).

920 g of the thus-obtained dry chip-like pulp was put into a batch-type vibrational mill (Chuo Kakohki's "FV-10": chamber total volume 35 L; 63 rods of SUS304 each having a diameter of 30 mm and a length of 510 mm and having a circular cross section; filling rate 65%). This was ground for 10 minutes (frequency 20 Hz, vibrational amplitude 8 mm, temperature 10 to 40° C.) to give a powdery cellulose (having a degree of crystallinity of 14%, a mean degree of polymerization of 1198 and a water content of 1.0%).

(2) Alkali Cellulose Production Step:

369 g of the powdery cellulose obtained in the above step (1) was put into a mixer (Matsubo's "Ledige Mixer", capacity 5 L), and with stirring at 250 rpm for the main blade and at 2500 rpm for the chopper blade, this was sprayed with 212 g of an aqueous 42.5% sodium hydroxide solution (corresponding to 1.0 mol of NaOH per mol of AGU, and 33% of water relative to cellulose) taking 1.5 minutes. After the spraying, the inner temperature was elevated up to 50° C., and the system was ripened for 3 hours to give an alkali cellulose.

(3) Hydroxypropylation Step 607 g of the alkali cellulose obtained in the above step (2) was heated up to 50° C. in the Ledige mixer with stirring at 50 rpm for the main blade and at 400 rpm for the chopper blade, and thereafter 187 g of propylene oxide (corresponding to 1.6 mols per mol of AGU) was dropwise added thereto taking 3.5 hours. After the addition, this was ripened at 50° C. for 2 hours.

(4) Cationization Step 11.4 g of the reaction mixture obtained in the above step (3) was taken into a mortar, and 4.31 g of aqueous 65% 3-chloro-2-hydroxypropyltrimethylammonium chloride solution (by Yokkaichi Gosei) (corresponding to 0.5 mols per mol of AGU) and 0.84 g of ion-exchanged water were added thereto and mixed for 5 minutes, and thereafter this was transferred into a 50-ml glass bottle and reacted therein at 50° C. for 5 hours to give a crude C-HPC. The crude C-HPC powder was neutralized, purified and freeze-dried in the same manner as in Production Example 15(4) to give a pure C-HPC (16).

The degree of substitution with cationized ethyleneoxy group and the degree of substitution with propyleneoxy group of the obtained pure C-HPC (16) were calculated to be 0.25 and 0.8, respectively. The mean degree of polymerization was 659.

Production Example 17

Production of C-HPC (17)

(1) Low-Crystalline Powdery Cellulose Production Step

In the same manner as in Production Example 16(1), a powdery cellulose (having a degree of crystallinity of 14%, a mean degree of polymerization of 1198 and a water content of 1.0%) was obtained.

(2) Alkali Cellulose Production Step:

An alkali cellulose was obtained in the same manner as in Production Example 16 (2), except that 530.5 g of the powdery cellulose obtained in the above step (1) and 307 g of an aqueous 42.5% sodium hydroxide solution (corresponding to 1.0 mol of NaOH per mol of AGU, and 34% of water relative to cellulose) were used.

(3) Hydroxypropylation Step 825 g of the alkali cellulose obtained in the above step (2) was heated up to 50° C. in the Ledige mixer with stirring at 50 rpm for the main blade and at 400 rpm for the chopper blade, and thereafter 467 g of propylene oxide (corresponding to 2.6 mols per mol of AGU) was dropwise added thereto taking 6 hours. After the addition, this was ripened at 50° C. for 2 hours.

(4) Cationization Step 12.3 g of the reaction mixture obtained in the above step (3) was taken into a mortar, and 4.31 g of aqueous 65% 3-chloro-2-hydroxypropyltrimethylammonium chloride solution (by Yokkaichi Gosei) (corresponding to 0.5 mols per mol of AGU) and 0.84 g of ion-exchanged water were added thereto and mixed for 5 minutes, and thereafter this was transferred into a 50-ml glass bottle and reacted therein at 50° C. for 5 hours to give a crude C-HPC. The crude C-HPC powder was neutralized, purified and freeze-dried in the same manner as in Production Example 16(4) to give a pure C-HPC (17). The degree of substitution with cationized ethyleneoxy group and the degree of substitution with propyleneoxy group of the obtained pure C-HPC (17) were calculated to be 0.19 and 1.4, respectively. The mean degree of polymerization was 1186.

The mean degree of polymerization of C-HPC (1) to (17) obtained in Production Examples 1 to 17 and the cationized cellulose obtained in Production Example 1(2), and the degree of substitution with cationized ethyleneoxy group and the degree of substitution with propyleneoxy group are collectively shown in Table 3.

TABLE 3

|  |  | Mean Degree of Polymerization of Obtained C-HPC | Degree of Substitution with Cationized EO *1 | Degree of Substitution with PO *2 | 2% Viscosity *3 |
|---|---|---|---|---|---|
| Production Example 1 | C-HPC(1) | 844 | 0.11 | 1.2 | — |
| Production Example 2 | C-HPC(2) | 170 | 0.10 | 1.2 | — |
| Production Example 3 | C-HPC(3) | 755 | 0.80 | 0.2 | 13600 |
| Production Example 4 | C-HPC(4) | 133 | 0.80 | 0.1 | — |
| Production Example 5 | C-HPC(5) | 216 | 0.30 | 0.3 | — |
| Production Example 6 | C-HPC(6) | 273 | 0.30 | 1.0 | — |
| Production Example 7 | C-HPC(7) | 341 | 0.30 | 1.5 | — |
| Production Example 8 | C-HPC(8) | 371 | 0.30 | 1.8 | — |
| Production Example 9 | C-HPC(9) | 241 | 0.84 | 0.2 | 32.8 |
| Production Example 10 | C-HPC(10) | 464 | 1.00 | 1.3 | — |
| Production Example 11 | C-HPC(11) | 295 | 1.40 | 0.2 | 6 |
| Production Example 12 | C-HPC(12) | 432 | 2.36 | 0.2 | 8.6 |
| Production Example 13 | C-HPC(13) | 387 | 0.10 | 1.2 | — |
| Production Example 14 | C-HPC(14) | 401 | 0.10 | 3.4 | — |
| Production Example 15 | C-HPC(15) | 759 | 0.14 | 1.0 | — |
| Production Example 16 | C-HPC(16) | 659 | 0.25 | 0.8 | — |
| Production Example 17 | C-HPC(17) | 1186 | 0.25 | 1.5 | — |
| Production Example 1(2) | Cationized Cellulose (1) | — | 0.11 | 0.0 | — |

*1: Degree of substitution with cationized ethyleneoxy group
*2: Degree of substitution with propyleneoxy group
*3: Viscosity of aqueous 2% C-HPC solution Examples 1 to 20, 27 to 29

Preparation and Evaluation of Skin Cleanser Composition (1) Preparation of Skin Cleanser Composition Using any of C-HPC (1) to (13) and (15) to (17) obtained in Production Examples 1 to 13 and 15 to 17, skin cleanser compositions as in Table 4 were produced according to an ordinary method.

Concretely, C-HPC was dissolved or uniformly dispersed in water to give a 2% polymer solution. Separately, the other components than the polymer were taken in a beaker, heated at 80° C., stirred and uniformly dissolved, and then, the polymer solution was added thereto, uniformly mixed and then cooled. Finally, water having evaporated away by heating was replenished, and the pH of the solution was measured. If desired, an aqueous 50% citric acid solution and 48% sodium hydroxide (hereinafter these may be referred to as "pH regulator") were added for pH regulation.

(2) Evaluation of Potency of Skin Cleanser Composition

Both hands were wetted, and 0.5 mL of the skin cleanser composition shown in Table 4 was applied to both hands, then foamed and thereafter the hands were rinsed with running water for 10 seconds. After 10 seconds, the hands were checked for the frictional resistance feeling according to the evaluation criteria mentioned below.

Subsequently, both hands were wiped with a towel to remove water, and after dried, the hands were again checked for the silky feeling with moisturization of the skin according to the evaluation criteria mentioned below.

Every test was carried out by five expert panelists. The scores they gave were averaged, and the mean score is shown in Table 4.

The samples having a mean score of 3.4 or more can be said to be obviously excellent in the evaluation test.
(Evaluation Criteria)
Frictional Resistance Feeling during Rinsing
  5: Strong.
  4: Relatively strong.
  3: Average (standard: frictional resistance feeling of the control sample in Table 4).
  2: Relatively weak.
  1: Weak.
Silky Feeling with Moisturization of Skin after Drying
  5: Feel strongly.
  4: Feel relatively strongly.
  3: Average (standard: silky feeling of the control sample in Table 1).
  2: Not feel so much.
  1: No silky feeling.

TABLE 4

|  |  | Skin Cleanser Composition | Example | | | | | | | | | | | |
|---|---|---|---|---|---|---|---|---|---|---|---|---|---|---|
|  |  |  | 1 | 2 | 3 | 4 | 5 | 6 | 7 | 8 | 9 | 10 | 11 | 12 |
| Constitutive Components (part by mass) | Component (A) | C-HPC(1) | — | — | — | — | — | 0.3 | — | — | — | — | — | — |
|  |  | C-HPC(2) | — | — | — | — | — | — | 0.3 | — | — | — | — | — |
|  |  | C-HPC(3) | — | — | — | — | — | — | — | 0.3 | — | — | — | — |
|  |  | C-HPC(4) | — | — | — | — | — | — | — | — | 0.3 | 0.1 | — | — |
|  |  | C-HPC(5) | — | — | — | — | — | — | — | — | — | — | 0.3 | — |
|  |  | C-HPC(6) | 0.3 | 0.3 | 0.3 | 0.3 | 0.3 | — | — | — | — | — | — | 0.3 |
|  |  | C-HPC(7) | — | — | — | — | — | — | — | — | — | — | — | — |
|  |  | C-HPC(8) | — | — | — | — | — | — | — | — | — | — | — | — |
|  |  | C-HPC(9) | — | — | — | — | — | — | — | — | — | — | — | — |
|  |  | C-HPC(10) | — | — | — | — | — | — | — | — | — | — | — | — |
|  |  | C-HPC(11) | — | — | — | — | — | — | — | — | — | — | — | — |
|  |  | C-HPC(12) | — | — | — | — | — | — | — | — | — | — | — | — |

TABLE 4-continued

| | | | | | | | | | | | | | |
|---|---|---|---|---|---|---|---|---|---|---|---|---|---|
| | | C-HPC(13) | — | — | — | — | — | — | — | — | — | — | — | — |
| | | C-HPC(15) | — | — | — | — | — | — | — | — | — | — | — | — |
| | | C-HPC(16) | — | — | — | — | — | — | — | — | — | — | — | — |
| | | C-HPC(17) | — | — | — | — | — | — | — | — | — | — | — | — |
| | Component (B) | sodium polyoxyethylene alkyl ether sulfate *4 | 12.0 | — | — | — | — | 9.1 | 9.1 | 9.1 | 9.1 | 9.1 | 9.1 | 9.1 |
| | | potassium laurate | — | 15.0 | — | — | — | — | — | — | — | — | — | — |
| | | sodium polyoxyethylene lauryl ether acetate *5 | — | — | 15.0 | — | — | — | — | — | — | — | — | — |
| | | lauryl glucoside *6 | — | — | — | 15.0 | — | — | — | — | — | — | — | — |
| | | Na cocoyl glutamate *7 | — | — | — | — | 15.0 | — | — | — | — | — | — | — |
| | | cocoyl fatty acid amide propylbetaine *8 | — | — | — | — | — | 1.6 | 1.6 | 1.6 | 1.6 | 1.6 | 1.6 | 1.6 |
| | | cocoyl fatty acid monoethanolamide *9 | — | — | — | — | — | 0.7 | 0.7 | 0.7 | 0.7 | 0.7 | 0.7 | 0.7 |
| | Others | glycerin | — | — | — | — | — | 1.2 | 1.2 | 1.2 | 1.2 | 1.2 | 1.2 | 1.2 |
| | | pH regulator | | | | | | adequate dose | | | | | | |
| | | pure water *10 | | | | | | balance | | | | | | |
| | pH (20-fold dilution, 25° C.) | | 6.0 | 9.5 | 6.0 | 6.0 | 6.0 | 6.0 | 6.0 | 6.0 | 6.0 | 6.0 | 6.0 | 6.0 |
| Evaluation | | frictional resistance feeling during rinsing | 3.8 | 5 | 4 | 4.6 | 4.6 | 3.6 | 3.6 | 3.8 | 4 | 3.6 | 3.8 | 3.8 |
| | | silky feeling after drying | 5 | 5 | 4 | 5 | 5 | 4 | 5 | 5 | 5 | 4 | 5 | 5 |

| | | Skin Cleanser Composition | Example 13 | 14 | 15 | 16 | 17 | 18 | 19 | 20 | 27 | 28 | 29 | Control |
|---|---|---|---|---|---|---|---|---|---|---|---|---|---|---|
| Constitutive Components (part by mass) | Component (A) | C-HPC(1) | — | — | — | — | — | — | — | — | — | — | — | — |
| | | C-HPC(2) | — | — | — | — | — | — | — | — | — | — | — | — |
| | | C-HPC(3) | — | — | — | — | — | — | — | — | — | — | — | — |
| | | C-HPC(4) | — | — | — | — | — | — | — | — | — | — | — | — |
| | | C-HPC(5) | — | — | — | — | — | — | — | — | — | — | — | — |
| | | C-HPC(6) | — | — | — | — | — | — | — | — | — | — | — | — |
| | | C-HPC(7) | 0.3 | 0.8 | — | — | — | — | — | — | — | — | — | — |
| | | C-HPC(8) | — | — | 0.3 | — | — | — | — | — | — | — | — | — |
| | | C-HPC(9) | — | — | — | 0.3 | — | — | — | — | — | — | — | — |
| | | C-HPC(10) | — | — | — | — | 0.3 | — | — | — | — | — | — | — |
| | | C-HPC(11) | — | — | — | — | — | 0.3 | — | — | — | — | — | — |
| | | C-HPC(12) | — | — | — | — | — | — | 0.3 | — | — | — | — | — |
| | | C-HPC(13) | — | — | — | — | — | — | — | 0.3 | — | — | — | — |
| | | C-HPC(15) | — | — | — | — | — | — | — | — | 0.3 | — | — | — |
| | | C-HPC(16) | — | — | — | — | — | — | — | — | — | 0.3 | — | — |
| | | C-HPC(17) | — | — | — | — | — | — | — | — | — | — | 0.3 | — |
| | Component (B) | sodium polyoxyethylene alkyl ether sulfate *4 | 9.1 | 9.1 | 9.1 | 9.1 | 9.1 | 9.1 | 9.1 | 9.1 | 9.1 | 9.1 | 9.1 | 9.1 |
| | | potassium laurate | — | — | — | — | — | — | — | — | — | — | — | — |
| | | sodium polyoxyethylene lauryl ether acetate *5 | — | — | — | — | — | — | — | — | — | — | — | — |
| | | lauryl glucoside *6 | — | — | — | — | — | — | — | — | — | — | — | — |
| | | Na cocoyl glutamate *7 | — | — | — | — | — | — | — | — | — | — | — | — |
| | | cocoyl fatty acid amide propylbetaine *8 | 1.6 | 1.6 | 1.6 | 1.6 | 1.6 | 1.6 | 1.6 | 1.6 | 1.6 | 1.6 | 1.6 | 1.6 |
| | | cocoyl fatty acid monoethanolamide *9 | 0.7 | 0.7 | 0.7 | 0.7 | 0.7 | 0.7 | 0.7 | 0.7 | 0.7 | 0.7 | 0.7 | 0.7 |
| | Others | glycerin | 1.2 | 1.2 | 1.2 | 1.2 | 1.2 | 1.2 | 1.2 | 1.2 | 1.2 | 1.2 | 1.2 | 1.2 |
| | | pH regulator | | | | adequate dose | | | | | | | | adequate dose |
| | | pure water *10 | | | | balance | | | | | | | | balance |
| | pH (20-fold dilution, 25° C.) | | 6.0 | 6.0 | 6.0 | 6.0 | 6.0 | 6.0 | 6.0 | 6.0 | 6.0 | 6.0 | 6.0 | 6.0 |
| Evaluation | | frictional resistance feeling during rinsing | 3.8 | 3.8 | 3.8 | 4.3 | 4 | 4.6 | 4.8 | 4 | 3.8 | 3.8 | 3.8 | 3 |
| | | silky feeling after drying | 5 | 5 | 5 | 5 | 5 | 5 | 5 | 4 | 5 | 5 | 5 | 3 |

*1: Nalco's trade name, MARCOAT 10
*2: Rhodia's trade name, JAGUAR C-13S
*3: Nippon Soda's trade name, CELNY M
*4: Kao's trade name, EMAL 270J
*5: Kao's trade name, KAOAKYPO RLM-45NV
*6: Kao's trade name, MYDOL 12
*7: Ajinomoto's trade name, AMISOFT CS-11
*8: Kao's trade name, AMPHITOL 55AB
*9: Kawaken Fine Chemical's trade name, AMIZOL CME
*10: Controlled to be 100 parts by mass in total.

Comparative Examples 1 to 14

Not using C-HPC (1) to (13) but using C-HPC (14) obtained in Production Example 14, or the cationized cellulose obtained in Production Example 1(2) or a commercially-available conditioning polymer in place of C-HPC (1) to (13), skin cleaner compositions shown in Table 5 were produced and evaluated in the same manner as in Examples 1 to 20. The results are shown in Table 5.

TABLE 5

| | Skin Cleanser Composition | Comparative Example | | | | | | | | | | | | | | Control |
|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | |
| Constitutive Components (part by mass) | C-HPC (14) | — | — | — | — | — | — | — | — | — | 0.3 | — | — | — | — | — |
| | cationized ellulose (1) | — | — | — | — | — | — | — | — | — | — | 0.3 | — | — | — | — |
| | cationized hydroxyethyl cellulose *1 | 0.3 | — | 0.3 | — | 0.3 | — | 0.3 | — | 0.3 | — | — | 0.3 | — | — | — |
| | cationized guar gum *2 | — | — | — | — | — | — | — | — | — | — | — | — | 0.3 | — | — |
| | hydroxypropyl cellulose *3 | — | — | — | — | — | — | — | — | — | — | — | — | — | 0.3 | — |
| Component (B) | sodium polyoxyethylene alkyl ether sulfate *4 | 12.0 | — | — | — | — | — | — | — | — | 9.1 | 9.1 | 9.1 | 9.1 | 9.1 | 9.1 |
| | potassium laurate | — | 15.0 | 15.0 | — | — | — | — | — | — | — | — | — | — | — | — |
| | sodium polyoxyethylene lauryl ether acetate *5 | — | — | — | 15.0 | 15.0 | — | — | — | — | — | — | — | — | — | — |
| | lauryl glucoside *6 | — | — | — | — | — | 15.0 | 15.0 | — | — | — | — | — | — | — | — |
| | Na cocoyl glutamate *7 | — | — | — | — | — | — | — | 15.0 | 15.0 | — | — | — | — | — | — |
| | cocoyl fatty acid amide propylbetaine *8 | — | — | — | — | — | — | — | — | — | 1.6 | 1.6 | 1.6 | 1.6 | 1.6 | 1.6 |
| | cocoyl fatty acid monoethanolamide *9 | — | — | — | — | — | — | — | — | — | 0.7 | 0.7 | 0.7 | 0.7 | 0.7 | 0.7 |
| Others | glycerin | — | — | — | — | — | — | — | — | — | 1.2 | 1.2 | 1.2 | 1.2 | 1.2 | 1.2 |
| | pH regulator | | | | | | adequate dose | | | | | | | | | adequate dose |
| | pure water *10 | | | | | | balance | | | | | | | | | balance |
| | pH (20-fold dilution, 25° C.) | 6.0 | 9.5 | 9.5 | 6.0 | 6.0 | 6.0 | 6.0 | 6.0 | 6.0 | 6.0 | 6.0 | 6.0 | 6.0 | 6.0 | 6.0 |
| Evaluation | frictional resistance feeling during rinsing | 1 | 5 | 4 | 3.6 | 1 | 3.6 | 1 | 3.6 | 3 | 3.6 | 3 | 1 | 1 | 2 | 3 |
| | silky feeling after drying | 1 | 1 | 1 | 2 | 1 | 2 | 1 | 2 | 1 | 1 | 2 | 1 | 1 | 2 | 3 |

*1: Nalco's trade name, MARCOAT 10
*2: Rhodia's trade name, JAGUAR C-13S
*3: Nippon Soda's trade name, CELNY M
*4: Kao's trade name, EMAL 270J
*5: Kao's trade name, KAOAKYPO RLM-45NV
*6: Kao's trade name, MYDOL 12
*7: Ajinomoto's trade name, AMISOFT CS-11
*8: Kao's trade name, AMPHITOL 55AB
*9: Kawaken Fine Chemical's trade name, AMIZOL CME
*10: Controlled to be 100 parts by mass in total.

From Examples in Table 4, it is known that the skin cleanser composition of the present invention satisfies both excellent frictional resistance feeling during rinsing and excellent silky feeling with moisturization after drying.

Example 21

Body Shampoo

Body shampoo having the composition mentioned below was produced according to an ordinary method.

Both hands were wetted, and 0.5 ml of the obtained body shampoo was applied to both hands, foamed, and then both hands were rinsed with running water for 10 seconds. After 10 seconds, both hands were checked for the frictional resistance feeling.

As a result, the body shampoo provided excellent frictional resistance feeling during rinsing, and gave silky feeling with moisturization to the skin after drying.

| (Component) | (%) |
|---|---|
| Lauric acid | 8.6 |
| Myristic acid | 8.4 |
| Palmitic acid | 2.5 |
| Sodium polyoxyethylene alkyl ether sulfate *1 | 2.9 |
| Glycerin | 1.9 |
| Propylene glycol | 1.2 |
| Cocoyl fatty acid amide propylbetaine *2 | 0.9 |
| C-HPC (6) | 0.3 |

-continued

| (Component) | (%) |
|---|---|
| Potassium hydroxide (to make pH 9.6) | adequate dose |
| Fragrance, Preservative | adequate dose |
| Pure water | balance |
| Total | 100.0 |

*1: Kao's trade name, EMAL 270J
*2: Kao's trade name, AMPHITOL 55AB

Example 22

Body Shampoo

Body shampoo having the composition mentioned below was produced according to an ordinary method, and evaluated in the same manner as in Example 21. As a result, the body shampoo provided excellent frictional resistance feeling during rinsing, and gave silky feeling with moisturization to the skin after drying.

| (Component) | (%) |
|---|---|
| Lauric acid | 5.5 |
| Myristic acid | 4.8 |
| Palmitic acid | 2.0 |
| Glycerin | 5.9 |

| (Component) | (%) |
|---|---|
| Laurylphosphoric acid | 2.2 |
| Cocoyl fatty acid amide propylbetaine *1 | 1.0 |
| Na cocoylisetionate *2 | 0.8 |
| Sodium polyoxyethylene alkyl ether sulfate *3 | 0.6 |
| Glycol distearate | 1.0 |
| C-HPC (6) | 0.3 |
| Potassium hydroxide (to make pH 9.1) | adequate dose |
| Fragrance, Preservative | adequate dose |
| Pure water | balance |
| Total | 100.0 |

*1: Kao's trade name, AMPHITOL 55AB
*2: NOF's trade name DIAPON C1
*3: Kao's trade name, EMAL 270J Example 23

Body Shampoo

Body shampoo having the composition mentioned below was produced according to an ordinary method, and evaluated in the same manner as in Example 21. As a result, the body shampoo provided excellent frictional resistance feeling during rinsing, and gave silky feeling with moisturization to the skin after drying.

| (Component) | (%) |
|---|---|
| K lauroylsarcosine *1 | 6.0 |
| Sodium polyoxyethylene alkyl ether sulfate *2 | 3.3 |
| Propylene glycol | 3.2 |
| Cocoyl fatty acid amide propylbetaine *3 | 2.8 |
| Glycol distearate | 1.0 |
| Cocoyl fatty acid diethanolamide | 0.7 |
| C-HPC (6) | 0.3 |
| Fragrance, Preservative | adequate dose |
| pH regulator (to make pH 6.0) | adequate dose |
| Pure water | balance |
| Total | 100.0 |

*1: Nikko Chemicals' trade name NIKKOL SARCOSINATE LK-30
*2: Kao's trade name, EMAL 270J
*3: Kao's trade name, AMPHITOL 55AB Example 24

Body Shampoo

Body shampoo having the composition mentioned below was produced according to an ordinary method, and evaluated in the same manner as in Example 21. As a result, the body shampoo provided excellent frictional resistance feeling during rinsing, and gave silky feeling with moisturization to the skin after drying.

| (Component) | (%) |
|---|---|
| Sodium polyoxyethylene alkyl ether sulfate *1 | 9.6 |
| Cocoyl fatty acid amide propylbetaine *2 | 1.4 |
| Na cocoamphoacetate *3 | 0.7 |
| Sodium chloride | 2.2 |
| C-HPC (6) | 0.3 |
| Fragrance, Preservative | adequate dose |

| (Component) | (%) |
|---|---|
| pH regulator (to make pH 6.0) | adequate dose |
| Pure water | balance |
| Total | 100.0 |

*1: Kao's trade name, EMAL 270J
*2: Kao's trade name, AMPHITOL 55AB
*3: Nikko Chemicals' trade name NIKKOL AM-101

Example 25

Face Wash

Face wash having the composition mentioned below was produced according to an ordinary method. Both hands were wetted, and 0.5 ml of the obtained face wash was applied to both hands, foamed, and then the face was washed and rinsed 10 times with scooped handfuls of water. As a result, the face wash provided excellent frictional resistance feeling during rinsing, and gave silky feeling with moisturization to the skin after drying.

| (Component) | (%) |
|---|---|
| Na cocoyl glycine *1 | 9.4 |
| Na cocoamphoacetate *2 | 2.5 |
| Cocoyl fatty acid amide propylbetaine *3 | 1.7 |
| Lauric acid | 2.0 |
| Glycerin | 6.0 |
| Vaseline | 9.0 |
| C-HPC (6) | 0.3 |
| Fragrance, Preservative | adequate dose |
| pH regulator (to make pH 6.0) | adequate dose |
| Pure water | balance |
| Total | 100.0 |

*1: Ajinomoto's trade name, AMILITE GCS-11
*2: Nikko Chemicals' trade name, NIKKOL AM-101
*3: Kao's trade name, AMPHITOL 55AB Example 26

Face Wash

Face wash having the composition mentioned below was produced and evaluated in the same manner as in Example 25. As a result, the face wash provided excellent frictional resistance feeling during rinsing, and gave silky feeling with moisturization to the skin after drying.

| (Component) | (%) |
|---|---|
| Na cocoyl methyltaurine *1 | 1.4 |
| Lauric acid | 28.2 |
| Myristic acid | 2.8 |
| Palmitic acid | 3.1 |
| PEG-32 *2 | 2.0 |
| Glycerin | 16.0 |
| C-HPC (4) | 0.3 |
| Fragrance, Preservative | adequate dose |
| pH regulator (to make pH 6.0) | adequate dose |
| Pure water | balance |
| Total | 100.0 |

*1: Nikko Chemicals' trade name, NIKKOL CMT-30
*2: NOF's trade name, PEG#1500

Production Example 18

Production of C-HPC (18)

(1) Chipping Step

A sheet-like wood pulp (Tembec's Biofloc HV+, having a mean degree of polymerization of 1770, a degree of crystallinity of 74% and a water content of 7.0%) was pelletized with a sheet pelletizer (Horai's "SGG-220") into chips of from 3 to 5 mm square.

(2) Cationization Step (1)

20.0 g of an aqueous solution of glycidyltrimethylammonium chloride (by Sakamoto Chemical Industry, water content 20%, purity 90% or more) (hereinafter referred to as "GMAC") (the amount corresponds to 0.2 mols per mol of AGU) was added to 86 g of the chip-like pulp obtained in the above (1), and mixed in a mortar, and then put into a batch-type vibrational mill (Chuo Kakohki's "MB-1"; chamber total volume 3.5 L; media of 13 rods of SUS304 each having a diameter of 30 mm and a length of 218 mm and having a circular cross section; filling rate 57%). This was ground for 12 minutes (frequency 20 Hz, vibrational amplitude 8 mm, temperature 30 to 70° C.) thereby giving a powdery mixture of cellulose and GMAC.

8.8 g (corresponding to 0.2 mols per mol of AGU) of an aqueous 48% sodium hydroxide solution was added to the obtained powdery mixture, mixed in a mortar and put into the above-mentioned batch-type vibrational mill. Under the same condition as above, this was ground for 60 minutes to give a cationized cellulose (i).

(3) Cationization Step (2)

114 g of the cationized cellulose (i) obtained in the above (2) was mixed with 32 g of GMAC (corresponding to 0.32 mols per mol of AGU) in a mortar, and then the resulting mixture was put into a 1-L kneader equipped with a reflux tube (Irie Shokai's PNV-1 Model), and with stirring at 50° C. in a nitrogen atmosphere at 50 rpm, this was ripened for 5 hours to give a cationized cellulose (ii).

(4) Cationization Step (3)

With stirring under reduced pressure (13.3 kPa), the cationized cellulose (ii) obtained in the above was dewatered at 60° C. to have a water content of 10.5% (relative to the starting cellulose), and thereafter 100 g of GMAC (corresponding to 1.0 mol per mol of AGU) was added thereto and reacted overnight at 50° C. thereby giving a cationized cellulose (iii).

(5) Hydroxypropylation Step

With stirring under reduced pressure (13.3 kPa), 140 g of the cationized cellulose (iii) (unneutralized, unpurified) was dewatered at 60° C. to have a water content of 9.3% (relative to the starting cellulose), then heated up to 70° C., and 20 g (corresponding to 1.0 mol per mol of AGU) of propylene oxide (Kanto Chemical's special grade reagent) was added thereto and reacted for 9 hours.

After the reaction, the reaction mixture was taken out as a crude C-HPC powder. The crude C-HPC powder was sampled and neutralized with acetic acid. For the purpose of determining the degree of substitution with propyleneoxy group and with cationized ethyleneoxy group, the neutralized product was purified through a dialytic membrane (molecular weight cut off, 1000), and then the aqueous solution was freeze-dried to give a pure C-HPC (18).

The degree of substitution with cationized ethyleneoxy group and the degree of substitution with propyleneoxy group of the obtained pure C-HPC (18) were calculated to be 0.77 and 0.2, respectively. The mean degree of polymerization was 1326.

Production Example 19

Production of C-HPC (19)

(1) Chipping Step

A sheet-like wood pulp (Tembec's Biofloc HV10, having a mean degree of polymerization of 1508, a degree of crystallinity of 74% and a water content of 7.0%) as cellulose was pelletized with a sheet pelletizer (Horai's "SGG-220") into chips of from 3 to 5 mm square.

(2) Cationization Step (1)

559 g of GMAC (corresponding to 0.52 mols per mol of AGU) and 24 g of ion-exchanged water were added to 989 g of the chip-like pulp obtained in the above (1) (water content 7.0%), and mixed in a plastic bag, and then put into a batch-type vibrational mill (ChuoKakohki's"FV-10": chamber total volume 35 L; media of 63 rods of SUS304 each having a diameter of 30 mm and a length of 510 mm and having a circular cross section; filling rate 64%). This was ground for 12 minutes (frequency 20 Hz, vibrational amplitude 8 mm, temperature 10 to 40° C.) thereby giving a powdery mixture of cellulose and GMAC.

136.2 g (corresponding to 0.60 mols per mol of AGU) of granular sodium (effective ingredient 100%) was put into the vibrational mill. Again this was ground for 112 minutes to give a cationized cellulose.

(3) Hydroxypropylation Step 95.0 g of the cationized cellulose obtained in the above (2) was put into the kneader equipped with a reflux tube used in Production Example 18, the kneader was heated up to 70° C., and with stirring, 35.4 g (corresponding to 2.0 mols per mol of AGU) of propylene oxide was dropwise added thereto, and the reaction was continued for 7 hours until the propylene oxide was consumed and the reflux flow stopped. After the reaction, the reaction mixture was taken out of the kneader to be a pale brown crude C-HPC powder.

(4) Cationization Step (2)

16.2 g (corresponding to 3.5 mols per mol of AGU) of GMAC was added to 10.6 g of the crude C-HPC powder obtained in the above (3), mixed in a mortar, and then ripened in a thermostat chamber at 50° C. for 24 hours. The obtained crude C-HPC was dispersed in 100 g of a mixed solvent of water/ethanol/isopropyl alcohol=5/45/50 (by mass), then neutralized with acetic acid added thereto, and purified through precipitation. The precipitate was collected through filtration, and dried under reduced pressure overnight in a drier at 60° C. thereby giving a pale brown bulky crude C-HPC (19).

For the purpose of determining the degree of substitution with propyleneoxy group and with cationized ethyleneoxy group, the product was purified through a dialytic membrane (molecular weight cut off, 1000), and then the aqueous solution was freeze-dried to give a pure C-HPC (19).

The degree of substitution with cationized ethyleneoxy group and the degree of substitution with propyleneoxy group of the obtained pure C-HPC (19) were calculated to be 1.00 and 1.3, respectively. The mean degree of polymerization was 464.

Production Example 20

Production of C-HPC (20)

This is the same as in Production Example 19, except that powdery cellulose (Nippon Paper Chemicals' cellulose powder KC Floc W-400G, having a mean degree of polymerization of 191, a degree of crystallinity of 77%, a water content of 7.0%) was used as the raw material, and that the cationization step (1), the hydroxypropylation step and the cationization step (2) were changed as in Table 6.

The degree of substitution with cationized ethyleneoxy group and the degree of substitution with propyleneoxy group of the obtained pure C-HPC (20) were calculated to be 1.40 and 0.2, respectively. The mean degree of polymerization was 295.

Production Example 21

Production of C-HPC (21)

This is the same as in Production Example 18, except that the condition in the cationization step (1) was changed as in Table 6, that the cationization step (2) was omitted and that the condition in the hydroxypropylation step was changed as in Table 6.

The degree of substitution with cationized ethyleneoxy group and the degree of substitution with propyleneoxy group of the obtained pure C-HPC (21) were calculated to be 0.24 and 2.2, respectively. The mean degree of polymerization was 478.

Production Example 22

Production of C-HPC (22)

This is the same as in Production Example 19, except that powdery cellulose (Nippon Paper Chemicals' cellulose powder KC Floc W-400G, having a mean degree of polymerization of 191, a degree of crystallinity of 77%, a water content of 7.0%) was used as the raw material, and that the cationization step (1), the hydroxypropylation step and the cationization step (2) were changed as in Table 6.

The degree of substitution with cationized ethyleneoxy group and the degree of substitution with propyleneoxy group of the obtained pure C-HPC (22) were calculated to be 2.36 and 0.2, respectively. The mean degree of polymerization was 432.

Production Example 23

Production of C-HPC (23)

This is the same as in Production Example 18, except that the condition in the cationization step (1) was changed as in Table 6, that the cationization step (2) was omitted and that the condition in the hydroxypropylation step was changed as in Table 6.

The degree of substitution with cationized ethyleneoxy group and the degree of substitution with propyleneoxy group of the obtained pure C-HPC (23) were calculated to be 0.22 and 1.1, respectively. The mean degree of polymerization was 539.

Production Example 24

Production of C-HPC (24)

This is the same as in Production Example 18, except that the condition in the cationization step (1) was changed as in Table 6, that the cationization step (2) was omitted and that the condition in the hydroxypropylation step was changed as in Table 6.

The degree of substitution with cationized ethyleneoxy group and the degree of substitution with propyleneoxy group of the obtained pure C-HPC (24) were calculated to be 0.35 and 2.7, respectively. The mean degree of polymerization was 964.

TABLE 6

| | Starting Pulp | | | Amount of Pulp Used (g) | Vibrational Mill | Cationization Step (1) | | | | |
|---|---|---|---|---|---|---|---|---|---|---|
| | Degree of crystallinity (%) | Mean Degree of Polymerization | Water Content (%) | | | Added Amount of GMAC *1 (g) | Grinding Time (min) | Added Amount of 48% NaOH (g) | Added Amount of Granular NaOH (g) | Grinding Time (min) |
| Production Example 18 | 74 | 1770 | 7.0 | 86 | MB-1 | 20.0 | 12 | 8.8 | — | 60 |
| Production Example 19 | 74 | 1508 | 7.0 | 989 | FV-10 | 559 | 12 | — | 136.2 | 112 |
| Production Example 20 | 77 | 191 | 7.0 | 100 | MB-1 | 60.8 | 12 | 29.8 | — | 60 |
| Production Example 21 | 74 | 1770 | 7.0 | 993 | FV-10 | 559 | 12 | — | 136.0 | 112 |
| Production Example 22 | 77 | 191 | 7.0 | 100 | MB-1 | 60.8 | 12 | 29.8 | — | 140 |
| Production Example 23 | 74 | 1770 | 7.0 | 100 | MB-1 | 60.8 | 12 | 14.8 | — | 120 |
| Production Example 24 | 74 | 1770 | 7.0 | 100 | MB-1 | 109 | 12 | 47.9 | — | 120 |
| Production Example 27 | 74 | 1770 | 7.0 | 86 | MB-1 | 20.0 | 12 | 8.8 | — | 60 |

| | Cationization Step (2) | | | | Cationization Step (3) | | | | Hydroxypropylation Step | | |
|---|---|---|---|---|---|---|---|---|---|---|---|
| | Amount of Cationized Cellulose (i) Used (g) | Added Amount of GMAC *1 (g) | Ripening Temperature (° C.) | Ripening Time (hr) | Amount of Cationized Cellulose (ii) Used (g) | Added Amount of GMAC *1 (g) | Ripening Temperature (° C.) | Ripening Time (hr) | Amount of Cationized Cellulose (ii) Used (g) | Added Amount of Propylene Oxide (g) | Reaction time (hr) |
| Production Example 18 | 114 | 32.0 | 50 | 5 | 140 | 100 | 50 | 24 | 240 *2 | 20.0 | 9 |
| Production Example 19 | 10.6 | 16.2 | 50 | 24 | — | — | — | — | 95 | 35.4 | 7 |
| Production Example 20 | 208 | 21.9 | 50 | 5 | — | — | — | — | 190 | 18.0 | 6 |
| Production Example 21 | — | — | — | — | — | — | — | — | 200 *3 | 117 | 13 |
| Production Example 22 | 45 | 152.0 | 50 | 24 | — | — | — | — | 190 | 18.0 | 2 |
| Production Example 23 | — | — | — | — | — | — | — | — | 100 *3 | 40.8 | 8 |

TABLE 6-continued

| | | | | | | | | | | | |
|---|---|---|---|---|---|---|---|---|---|---|---|
| Production Example 24 | — | — | — | — | — | — | — | — | 220 *3 | 153 | 5 |
| Production Example 27 | 114 | 32.0 | 50 | 5 | — | — | — | — | — | — | — |

*1: Water content 20%.
*2: Cationized cellulose (i) was used in place of cationized cellulose (ii).
*3: Cationized cellulose (iii) was used in place of cationized cellulose (ii).

Production Example 25

Production of C-HPC (25)

(1) Chipping Step

A sheet-like wood pulp (Tembec's Biofloc HV+, having a mean degree of polymerization of 1481, a degree of crystallinity of 74% and a water content of 4.6%) was pelletized with a sheet pelletizer (Horai's "SGG-220") into chips of from 3 to 5 mm square. The obtained chip-like pulp was put into a drier (Advantec Toyo's "VO-402"), and dried therein at 105° C. for 2 hours to give a dry chip-like pulp.

(2) Powdering/Crystallinity Reduction Step

The obtained dry chip-like pulp was ground in a batch-type vibrational mill (Chuo Kakohki's "MB-1": chamber total volume 3.5 L; media of 13 rods of SUS304 each having a diameter of 30 mm and a length of 218 mm; filling rate 57%) for 1 hour (frequency 20 Hz, vibrational amplitude 8 mm, temperature 30 to 70° C.) thereby giving a low-crystalline powdery cellulose (having a degree of crystallinity of 11.2%, a mean degree of polymerization of 765, and a water content of 0.6%).

(3) Cationization Step 9.4 g (corresponding to 0.4 mols per mol of AGU) of an aqueous 80% GMAC solution was added all at a time to 20.0 g of the low-crystalline powdery cellulose obtained in the above step (2) (water content 0.6%), and mixed in a mortar. Subsequently, 4.5 g (corresponding to 0.1 mols per mol of AGU) of an aqueous 11% sodium hydroxide solution was added thereto all at a time, and mixed in a mortar (water content relative to cellulose: 30% by mass). The obtained mixture was transferred to a 1-L kneader equipped with a reflux tube (Irie Shokai's PNV-1 Model), and the system was purged with nitrogen, heated up to 70° C. and ripened for 2.5 hours to give a cationized cellulose.

(4) Hydroxypropylation Step

Subsequently, 7.1 g (corresponding to 1.0 mol per mol of AGU) of propylene oxide was dropwise added to the cationized cellulose in the above (3) at 70° C., taking 1 hour, and then ripened for 2 hours. The process from the propylene oxide addition to the ripening was repeated five times (the total amount of the added propylene oxide was 35.5 g, corresponding to 5.0 mols per mol of AGU). Like in Production Example (1), the crude C-HPC powder was neutralized, purified and freeze-dried to give a pure C-HPC (25).

The degree of substitution with cationized ethyleneoxy group and the degree of substitution with propyleneoxy group of the obtained pure C-HPC (25) were calculated to be 0.18 and 1.8, respectively. The mean degree of polymerization was 732.

Production Example 26

Production of C-HPC (26)

(1) Chipping Step

A sheet-like wood pulp (Tembec's Biofloc HV+, having a mean degree of polymerization of 1481, a degree of crystallinity of 74% and a water content of 4.6%) was pelletized with a sheet pelletizer (Horai's "SGG-220") into chips of from 3 to 5 mm square. The obtained chip-like pulp was put into a drier (Advantec Toyo's "VO-402"), and dried therein at 105° C. for 2 hours to give a dry chip-like pulp (water content 0.8%).

(2) Powdering/Crystallinity Reduction Step

The obtained dry chip-like pulp was put into a batch-type vibrational mill (Chuo Kakohki's "FV-10": chamber total volume 35 L; media of 63 rods of SUS304 each having a diameter of 30 mm and a length of 510 mm and having a circular cross section; filling rate 65%). This was ground for 10 minutes (frequency 30 Hz, vibrational amplitude 8 mm, temperature 10 to 40° C.) to give a low-crystalline powdery cellulose (having a degree of crystallinity of 14%, a mean degree of polymerization of 1198, and a water content of 1.0%).

(3) Alkali Cellulose Production Step 4450 g of the low-crystalline powdery cellulose obtained in the above step (2) was put into a proshear mixer, and with stirring at 1 m/sec for the main blade and at 1800 rpm for the chopper blade, this was sprayed with 2396 g of an aqueous 42.6% sodium hydroxide solution (corresponding to 0.93 mols per mol of AGU) at 1.0 L/min. After the spraying, the inner temperature was elevated up to 50° C., and the system was ripened for 2 hours to give an alkali cellulose.

(4) Hydroxypropylation Step 6846 g of the alkali cellulose obtained in the above step was heated up to 50° C. in the above-mentioned proshear mixer with stirring at 1 m/sec for the main blade and at 1800 rpm for the chopper blade, and thereafter 5580 g of propylene oxide (corresponding to 3.5 mols per mol of AGU) was dropwise added thereto as divided in 12 portions. After the addition, this was ripened at 50° C. for 2 hours.

(5) Cationization Step 192.0 g of the reaction mixture obtained in the above step was put into a vertical granulator and, with stirring, sprayed with 77.25 g of an aqueous 70% hydroxylammonium chloride solution (corresponding to 0.52 mols per mol of AGU) at 0.2 L/min, and reacted at 50° C. for 2 hours to give a crude C-HPC. The crude C-HPC powder was neutralized, purified and freeze-dried in the same manner as in Production Example 18 to give a pure C-HPC (26).

The degree of substitution with cationized ethyleneoxy group and the degree of substitution with propyleneoxy group of the obtained pure C-HPC (26) were calculated to be 0.22 and 2.1, respectively. The mean degree of polymerization was 212.

Production Example 27

Production of Cationized Cellulose (27)

A cationized cellulose (27) was produced in the same manner as in Production Example 18 except that the hydroxypropylation step was omitted.

The degree of substitution with cationized ethyleneoxy group of the obtained pure cationized cellulose (27) was calculated to be 0.77. The mean degree of polymerization was 1288.

The mean degree of polymerization, the degree of substitution with cationized ethyleneoxy group and the degree of substitution with propyleneoxy group of C-HPC (18) to (26) obtained in Production Examples 18 to 26 and the cationized cellulose (27) obtained in Production Example 27 are summarized in Table 7.

(Step (III))

The emulsion was mixed with a surfactant (B) in an amount indicated in the step (III) in Table 8 and other components and water, and stirred at 25° C. and at 100 rpm (0.26 m/sec) for 30 minutes to give a skin cleanser composition (body shampoo).

(2) Determination of Mean Particle Size of Oil Drops

The mean particle size of oil drops was determined, using a dynamic light scattering particle sizer LA-950 (by Horiba). For preventing the sample from being contaminated with bubbles during measurement, the emulsion was completely dispersed in the cell of LA-950 (measurement condition: stirring 7, circulation 7), and after the stirring and the circulation were stopped, the sample was tested. The volume-based median diameter was measured at a temperature of 25° C., and was referred to as the mean particle size.

A smaller mean particle size of oil drops means that the emulsion force of the oil (C) is large, while a larger mean particle size thereof means that the emulsion force is small.

(3) Evaluation of Emulsion Condition

The cationized hydroxypropyl cellulose (A) and the anionic surfactant (B') were mixed, and the oil (C) was gradually added thereto and stirred and emulsified. From the out-

TABLE 7

|  |  | Mean Degree of Polymerization | Degree of Substitution with Cationized EO *1 | Degree of Substitution with PO *2 |
|---|---|---|---|---|
| Production Example 18 | C-HPC (18) | 1326 | 0.77 | 0.2 |
| Production Example 19 | C-HPC (19) | 464 | 1.00 | 1.3 |
| Production Example 20 | C-HPC (20) | 295 | 1.40 | 0.2 |
| Production Example 21 | C-HPC (21) | 478 | 0.24 | 2.2 |
| Production Example 22 | C-HPC (22) | 432 | 2.36 | 0.2 |
| Production Example 23 | C-HPC (23) | 539 | 0.22 | 1.1 |
| Production Example 24 | C-HPC (24) | 964 | 0.35 | 2.7 |
| Production Example 25 | C-HPC (25) | 732 | 0.18 | 1.8 |
| Production Example 26 | C-HPC (26) | 212 | 0.22 | 2.1 |
| Production Example 27 | Cationized Cellulose (27) | 1288 | 0.77 | 0.0 |

*1: Degree of substitution with cationized ethyleneoxy group
*2: Degree of substitution with propyleneoxy group Examples 30 to 38

Production and Evaluation of Body Shampoo (1) Preparation of Skin Cleanser Composition Using C-HPC (18) to (26) obtained in Production Examples 18 to 26, skin cleanser compositions of Examples shown in Table 8 were produced. Concretely, the compositions were produced as follows.

(Step (I))

An aqueous solution of C-HPC (A) (having a C-HPC concentration of 4%) and an anionic surfactant (B') in an amount indicated in the step (I) in Table 8 were taken in a beaker, and mixed to be uniform at 25° C. at 300 rpm (0.78 m/sec) for 10 minutes until, thereby preparing a mixture containing the C-HPC (A) and the anionic surfactant (B').

(Step (II))

An oil (C) in an amount shown in Table 8 was gradually added to the mixture, and emulsified with stirring at 25° C. and at 300 rpm (0.78 m/sec). After all the oil had been added, this was emulsified for 10 minutes to give an emulsion.

ward appearance of the obtained emulsion, the emulsified condition thereof was evaluated according to the following evaluation criteria.

(Evaluation Criteria)

Emulsion Condition

A: Well emulsified.

B: Not emulsified (oily drops aggregated).

(4) Determination of Amount of Remaining Oil

A 10-fold dilution was prepared by diluting 1 ml of a skin cleanser composition with 10 ml of ion-exchanged water in a 50-ml beaker. A model skin (by Izumikou) of 3 cm square was put into it and stirred with fingers for 10 seconds. This operation is for washing. 500 ml of water was put into a 500-ml beaker, and the model skin was dipped in water in the beaker repeatedly five times, and this operation is for rinsing. After spontaneously dried, this was extracted with 5 ml of chloroform for 15 seconds. This operation was repeated three times. The extract was dried along with 5 ml of dinitrobenzene (2000 ppm), then again dissolved in 1 ml of heavy chloroform and analyzed through $^1$H-NMR. According to an internal standard method with dinitrobenzene, the remaining oil amount on the model skin (mg/cm$^2$) was quantified.

(5) Evaluation of Potency of Skin Cleanser Composition

Both hands were wetted, 0.5 ml of a skin cleanser composition sample was applied to both hands and foamed for 10 seconds, and then, during washing, the foamability of the sample was evaluated according to the following evaluation criteria.

Subsequently, both hands were rinsed with running water for 10 seconds, and wiped with a towel for removing water, and after dried, the moisturization feeling of the skin was evaluated according to the following evaluation criteria.

Every test was carried out by five expert panelists. The scores they gave were averaged, and the mean score is shown in Tables 8 to 11.

The samples having a mean score of 3.5 or more can be said to be obviously excellent in the evaluation test.

(Evaluation Criteria)
Foamability in Washing
5: Many foams formed.
4: Somewhat many foams formed.
3: Average (standard: foamability of Comparative Example 21 in Table 8)
2: Relatively a few foams formed.
1: Few foams formed.

Moisturization Feeling of Skin after Drying
5: Feel strongly.
4: Feel relatively strongly.
3: Average (standard: moisturization feeling of Comparative Example 21 Table 8).
2: Not feel so much.
1: No moisturization feeling.

Comparative Examples 15 to 20

Production and Evaluation of Body Shampoo

Skin cleanser compositions (body shampoo) shown in Table 8 were produced and evaluated in the same manner as in Example 30, except that the cationized cellulose obtained in Production Example 27 or a commercially-available polymer was used in place of C-HPC (18) to (26). The results are shown in Table 8.

Comparative Example 21

A skin cleanser composition (body shampoo) was produced and evaluated in the same manner as in Example 30, except that the step (I) was omitted. The results are shown in Table 8. In Comparative Example 21, the oil was emulsified by the surfactant added in the step (III).

TABLE 8

| | | | | Example | | | | | | | | |
|---|---|---|---|---|---|---|---|---|---|---|---|---|
| Skin Cleanser Composition | | | | 30 | 31 | 32 | 33 | 34 | 35 | 36 | 37 | 38 |
| Constitutive Components (part by mass) | Step (I) | Component (A) | C-HPC (18) | 0.55 | | | | | | | | |
| | | | C-HPC (19) | | 0.55 | | | | | | | |
| | | | C-HPC (20) | | | 0.55 | | | | | | |
| | | | C-HPC (21) | | | | 0.55 | | | | | |
| | | | C-HPC (22) | | | | | 0.55 | | | | |
| | | | C-HPC (23) | | | | | | 0.55 | | | |
| | | | C-HPC (24) | | | | | | | 0.55 | | |
| | | | C-HPC (25) | | | | | | | | 0.55 | |
| | | | C-HPC (26) | | | | | | | | | 0.55 |
| | | Component (A') | Cationized Cellulose (27) | | | | | | | | | |
| | | | Cationized Hydroxyethyl Cellulose *1 | | | | | | | | | |
| | | | Hydroxyethyl Cellulose *2 | | | | | | | | | |
| | | | Hydroxypropyl Cellulose *3 | | | | | | | | | |
| | | | Cationized Guar Gum *4 | | | | | | | | | |
| | | | Dimethyldiallylammonium Chloride/Acrylamide Copolymer *5 | | | | | | | | | |
| | | Component (B') | Sodium Polyoxyethylene (2) Lauryl Ether Sulfate *6 | 0.055 | 0.055 | 0.055 | 0.055 | 0.055 | 0.055 | 0.055 | 0.055 | 0.055 |
| | | | Pure Water | 13.4 | 13.4 | 13.4 | 13.4 | 13.4 | 13.4 | 13.4 | 13.4 | 13.4 |
| | Step (II) | Component (C) | Sunflower Oil | 22.0 | 22.0 | 22.0 | 22.0 | 22.0 | 22.0 | 22.0 | 22.0 | 22.0 |
| | | Ratio by Mass | Component (B)/[Component (A) or (A')] | 0.1 | 0.1 | 0.1 | 0.1 | 0.1 | 0.1 | 0.1 | 0.1 | 0.1 |
| | | | Component (C)/[Component (A) or (A')] | 40 | 40 | 40 | 40 | 40 | 40 | 40 | 40 | 40 |
| | | Emulsion Evaluation | Mean Particle Size of Oil Drops [μm] | 13.4 | 15.4 | 55.4 | 10.0 | 82.8 | 18.1 | 16.6 | 18.6 | 39.2 |
| | | | Emulsion Condition | A | A | A | A | A | A | A | A | A |
| | Step (III) | Component (B) | Sodium Polyoxyethylene(2) Lauryl Ether Sulfate *6 | 12.0 | 12.0 | 12.0 | 12.0 | 12.0 | 12.0 | 12.0 | 12.0 | 12.0 |
| | | Others | Cocoyl Fatty Acid Amide Propylbetaine *7 | 5.0 | 5.0 | 5.0 | 5.0 | 5.0 | 5.0 | 5.0 | 5.0 | 5.0 |
| | | | Cocoyl Fatty Acid Monoethanolamide *8 | 3.0 | 3.0 | 3.0 | 3.0 | 3.0 | 3.0 | 3.0 | 3.0 | 3.0 |
| | | | Glycerin | 6.5 | 6.5 | 6.5 | 6.5 | 6.5 | 6.5 | 6.5 | 6.5 | 6.5 |
| | | | Lauric Acid *9 | 3.5 | 3.5 | 3.5 | 3.5 | 3.5 | 3.5 | 3.5 | 3.5 | 3.5 |
| | | | Vaseline | 3.0 | 3.0 | 3.0 | 3.0 | 3.0 | 3.0 | 3.0 | 3.0 | 3.0 |
| | | | Cationized Guar Gum *4 | 0.5 | 0.5 | 0.5 | 0.5 | 0.5 | 0.5 | 0.5 | 0.5 | 0.5 |
| | | | Pure Water | | | | | balance | | | | |

TABLE 8-continued

| | | | | | | | | | | |
|---|---|---|---|---|---|---|---|---|---|---|
| pH (20-fold dilution, 25° C.) | | | 6.6 | 6.6 | 6.6 | 6.6 | 6.6 | 6.6 | 6.6 | 6.6 | 6.6 |
| Component (B)/[Component (A) or Component (A')] | | | 21.9 | 21.9 | 21.9 | 21.9 | 21.9 | 21.9 | 21.9 | 21.9 | 21.9 |
| Evaluation Results | Remaining Oil Amount [mg/cm²] | | 1.0 | 1.2 | 1.3 | 0.8 | 1.5 | 0.9 | 0.6 | 1.0 | 1.0 |
| | Foamability in Washing | | 5.0 | 5.0 | 5.0 | 5.0 | 5.0 | 5.0 | 5.0 | 5.0 | 5.0 |
| | Moisturization Feeling after Drying | | 5.0 | 5.0 | 5.0 | 4.6 | 5.0 | 5.0 | 4.6 | 5.0 | 5.0 |

| | | | | Comparative Example | | | | | | |
|---|---|---|---|---|---|---|---|---|---|---|
| | | Skin Cleanser Composition | | 15 | 16 | 17 | 18 | 19 | 20 | 21 |
| Constitutive Components (part by mass) | Step (I) | Component (A) | C-HPC (18) | | | | | | | |
| | | | C-HPC (19) | | | | | | | |
| | | | C-HPC (20) | | | | | | | |
| | | | C-HPC (21) | | | | | | | |
| | | | C-HPC (22) | | | | | | | |
| | | | C-HPC (23) | | | | | | | |
| | | | C-HPC (24) | | | | | | | |
| | | | C-HPC (25) | | | | | | | |
| | | | C-HPC (26) | | | | | | | |
| | | Component (A') | Cationized Cellulose (27) | 0.55 | | | | | | |
| | | | Cationized Hydroxyethyl Cellulose *1 | | 0.55 | | | | | |
| | | | Hydroxyethyl Cellulose *2 | | | 0.55 | | | | |
| | | | Hydroxypropyl Cellulose *3 | | | | 0.55 | | | |
| | | | Cationized Guar Gum *4 | | | | | 0.55 | | |
| | | | Dimethyldiallylammonium Chloride/Acrylamide Copolymer *5 | | | | | | 0.55 | |
| | | Component (B') | Sodium Polyoxyethylene (2) Lauryl Ether Sulfate *6 | 0.055 | 0.055 | | | 0.055 | 0.055 | |
| | | | Pure Water | 13.4 | 13.4 | 13.2 | 13.2 | 13.4 | 13.4 | — |
| | Step (II) | Component (C) | Sunflower Oil | 22.0 | 22.0 | 22.0 | 22.0 | 22.0 | 22.0 | 22.0 |
| | | Ratio by Mass | Component (B)/[Component (A) or (A')] | 0.1 | 0.1 | — | — | 0.1 | 0.1 | — |
| | | | Component (C)/[Component (A) or (A')] | 40 | 40 | 40 | 40 | 40 | 40 | — |
| | | Emulsion Evaluation | Mean Particle Size of Oil Drops [μm] | 10.4 | — | — | — | — | 8.9 | — |
| | | | Emulsion Condition | A | B | B | B | B | A | — |
| | Step (III) | Component (B) | Sodium Polyoxyethylene(2) Lauryl Ether Sulfate *6 | 12.0 | 12.0 | 12.0 | 12.0 | 12.0 | 12.0 | 12.0 |
| | | Others | Cocoyl Fatty Acid Amide Propylbetaine *7 | 5.0 | 5.0 | 5.0 | 5.0 | 5.0 | 5.0 | 5.0 |
| | | | Cocoyl Fatty Acid Monoethanolamide *8 | 3.0 | 3.0 | 3.0 | 3.0 | 3.0 | 3.0 | 3.0 |
| | | | Glycerin | 6.5 | 6.5 | 6.5 | 6.5 | 6.5 | 6.5 | 6.5 |
| | | | Lauric Acid *9 | 3.5 | 3.5 | 3.5 | 3.5 | 3.5 | 3.5 | 3.5 |
| | | | Vaseline | 3.0 | 3.0 | 3.0 | 3.0 | 3.0 | 3.0 | 3.0 |
| | | | Cationized Guar Gum *4 | 0.5 | 0.5 | 0.5 | 0.5 | 0.5 | 0.5 | 0.5 |
| | | | Pure Water | | | | balance | | | |
| | pH (20-fold dilution, 25° C.) | | | 6.6 | — | — | — | — | 6.6 | 6.6 |
| | Component (B)/[Component (A) or Component (A')] | | | 21.9 | 21.9 | 21.8 | 21.8 | 21.9 | 21.9 | — |
| Evaluation Results | Remaining Oil Amount [mg/cm²] | | | 1.0 | — | — | — | — | 1.1 | 0.5 |
| | Foamability in Washing | | | 3.4 | — | — | — | — | 3.0 | 3.0 |
| | Moisturization Feeling after Drying | | | 3.0 | — | — | — | — | 4.0 | 3.0 |

*1: Nalco's trade name, MARCOAT 10
*2: Daicel Chemical Industry's trade name: HEC-SE850K
*3: Nippon Soda's trade name: HPC-M
*4: Sansho's trade name: JAGUAR C145
*5: Nalco's trade name, MARCOAT 550
*6: Kao's trade name, EMAL 270S
*7: Kao's trade name, AMPHITOL 55AB
*8: Kawaken Fine Chemical's trade name, AMIZOL CME
*9: Kao's trade name, LUNAC L-98

Examples 39 to 60

Comparative Examples 22 to 23

Production and Evaluation of Body Shampoo

Skin cleanser compositions of Examples 39 to 60 and Comparative Examples 22 to 23 shown in Tables 9 and 10 were produced and evaluated in the same manner as in Examples 30 to 38. The results are shown in Tables 9 and 10.

TABLE 9

| | | | Skin Cleanser Composition | Example 39 | Example 40 | Example 41 | Comparative Example 22 | Example 42 | Example 43 | Example 44 | Example 45 |
|---|---|---|---|---|---|---|---|---|---|---|---|
| Constitutive Components (part by mass) | Step (I) | Component (A) | C-HPC (23) | 0.055 | 0.11 | 0.22 | 0.0275 | 0.55 | 0.55 | 0.55 | 0.55 |
| | | Component (B') | Sodium Polyoxyethylene (2) Lauryl Ether sulfate *1 | 0.055 | 0.055 | 0.055 | 0.055 | 1.1 | 0.55 | 0.275 | 0.138 |
| | | | Pure Water | 1.54 | 2.86 | 5.5 | 0.88 | 17.6 | 15.4 | 14.3 | 13.75 |
| | Step (II) | Component (C) | Sunflower Oil | 22.0 | 22.0 | 22.0 | 22.0 | 22.0 | 22.0 | 22.0 | 22.0 |
| | Ratio by Mass | | Component (B)/Component (A) | 1.0 | 0.5 | 0.3 | 2.0 | 2.0 | 1.0 | 0.5 | 0.3 |
| | | | Component (C)/Component (A) | 400 | 200 | 100 | 800 | 40 | 40 | 40 | 40 |
| | Emulsion Evaluation | | Mean Particle Size of Oil Drops [μm] | 14.1 | 33.2 | 26.0 | 128.6 | 9.0 | 13.7 | 21.1 | 8.9 |
| | | | Emulsion Condition | A | A | A | B | A | A | A | A |
| | Step (III) | Component (B) | Sodium Polyoxyethylene(2) Lauryl Ether Sulfate *1 | 12.0 | 12.0 | 12.0 | 12.0 | 12.0 | 12.0 | 12.0 | 12.0 |
| | | Others | Cocoyl Fatty Acid Amide Propylbetaine *2 | 5.0 | 5.0 | 5.0 | 5.0 | 5.0 | 5.0 | 5.0 | 5.0 |
| | | | Cocoyl Fatty Acid Monoethanolamide *3 | 3.0 | 3.0 | 3.0 | 3.0 | 3.0 | 3.0 | 3.0 | 3.0 |
| | | | Glycerin | 6.5 | 6.5 | 6.5 | 6.5 | 6.5 | 6.5 | 6.5 | 6.5 |
| | | | Lauric Acid *4 | 3.5 | 3.5 | 3.5 | 3.5 | 3.5 | 3.5 | 3.5 | 3.5 |
| | | | Vaseline | 3.0 | 3.0 | 3.0 | 3.0 | 3.0 | 3.0 | 3.0 | 3.0 |
| | | | Cationized Guar Gum *5 | 0.5 | 0.5 | 0.5 | 0.5 | 0.5 | 0.5 | 0.5 | 0.5 |
| | | | Pure Water | | | | balance | | | | |
| | pH (20-fold dilution, 25° C.) | | | 6.6 | 6.6 | 6.6 | 6.6 | 6.6 | 6.6 | 6.6 | 6.6 |
| | Component (B)/Component (A) | | | 219.2 | 109.6 | 54.8 | 438.4 | 23.8 | 22.8 | 22.3 | 22.1 |
| Evaluation Results | | | Remaining Oil Amount [mg/cm²] | 0.9 | 1.4 | 1.4 | — | 0.7 | 1.1 | 0.9 | 0.9 |
| | | | Foamability in Washing | 4.0 | 4.0 | 4.0 | — | 3.6 | 4.0 | 4.0 | 4.0 |
| | | | Moisturization Feeling after Drying | 5.0 | 5.0 | 5.0 | — | 3.6 | 4.0 | 4.0 | 4.0 |

| | | | Skin Cleanser Composition | Example 46 | Example 47 | Example 48 | Example 49 | Example 50 | Example 51 | Comparative Example 23 |
|---|---|---|---|---|---|---|---|---|---|---|
| Constitutive Components (part by mass) | Step (I) | Component (A) | C-HPC (23) | 0.55 | 0.55 | 0.55 | 0.55 | 0.55 | 0.55 | 0.55 |
| | | Component (B') | Sodium Polyoxyethylene (2) Lauryl Ether sulfate *1 | 0.014 | 0.006 | 0.055 | 0.055 | 0.055 | 0.055 | 0.055 |
| | | | Pure Water | 13.26 | 13.22 | 13.42 | 13.42 | 13.42 | 13.42 | 13.42 |
| | Step (II) | Component (C) | Sunflower Oil | 22.0 | 22.0 | 1.1 | 5.5 | 16.5 | 27.5 | 0.55 |
| | Ratio by Mass | | Component (B)/Component (A) | 0.03 | 0.01 | 0.1 | 0.1 | 0.1 | 0.1 | 0.1 |
| | | | Component (C)/Component (A) | 40 | 40 | 2 | 10 | 30 | 50 | 1 |
| | Emulsion Evaluation | | Mean Particle Size of Oil Drops [μm] | 8.8 | 68.4 | 38.1 | 33.1 | 23.9 | 5.8 | 35.2 |
| | | | Emulsion Condition | A | A | A | A | A | A | A |
| | Step (III) | Component (B) | Sodium Polyoxyethylene(2) Lauryl Ether Sulfate *1 | 12.0 | 12.0 | 12.0 | 12.0 | 12.0 | 12.0 | 12.0 |
| | | Others | Cocoyl Fatty Acid Amide Propylbetaine *2 | 5.0 | 5.0 | 5.0 | 5.0 | 5.0 | 5.0 | 5.0 |
| | | | Cocoyl Fatty Acid Monoethanolamide *3 | 3.0 | 3.0 | 3.0 | 3.0 | 3.0 | 3.0 | 3.0 |
| | | | Glycerin | 6.5 | 6.5 | 6.5 | 6.5 | 6.5 | 6.5 | 6.5 |
| | | | Lauric Acid *4 | 3.5 | 3.5 | 3.5 | 3.5 | 3.5 | 3.5 | 3.5 |
| | | | Vaseline | 3.0 | 3.0 | 3.0 | 3.0 | 3.0 | 3.0 | 3.0 |
| | | | Cationized Guar Gum *5 | 0.5 | 0.5 | 0.5 | 0.5 | 0.5 | 0.5 | 0.5 |
| | | | Pure Water | | | | | | | |
| | pH (20-fold dilution, 25° C.) | | | 6.6 | 6.6 | 6.5 | 6.5 | 6.6 | 6.6 | 6.5 |
| | Component (B)/Component (A) | | | 21.8 | 21.8 | 21.9 | 21.9 | 21.9 | 21.9 | 21.9 |

TABLE 9-continued

|  |  |  |  |  |  |  |  |  |
|---|---|---|---|---|---|---|---|---|
| Evaluation Results | Remaining Oil Amount [mg/cm$^2$] | 0.9 | 0.9 | 0.1 | 0.2 | 0.7 | 1.0 | 0.03 |
|  | Foamability in Washing | 4.0 | 4.0 | 5.0 | 5.0 | 5.0 | 5.0 | 5.0 |
|  | Moisturization Feeling after Drying | 3.6 | 3.6 | 3.0 | 3.6 | 5.0 | 5.0 | 2.4 |

*1: Kao's trade name, EMAL 270S

*2: Kao's trade name, AMPHITOL 55AB

*3: Kawaken Fine Chemical's trade name, AMIZOL CME

*4: Kao's trade name, LUNAC L-98

*5: Sansho's trade name: JAGUAR C14S

TABLE 10

| Skin Cleanser Composition | | | | Example | | | | | | | | |
|---|---|---|---|---|---|---|---|---|---|---|---|---|
|  |  |  |  | 52 | 53 | 54 | 55 | 56 | 57 | 58 | 59 | 60 |
| Constitutive Components (part by mass) | Step (I) | Component (A) | C-HPC (23) | 0.55 | 0.55 | 0.55 | 0.55 | 0.55 | 0.55 | 0.55 | 0.55 | 0.55 |
|  |  | Component (B') | Sodium Laurate *1 | 0.055 |  |  |  |  |  |  |  |  |
|  |  |  | Sodium Polyoxyethylene (1) Lauryl Ether Sulfate *2 |  | 0.055 |  |  |  |  |  |  |  |
|  |  |  | Sodium Polyoxyethylene (2) Lauryl Ether Sulfate *3 |  |  | 0.055 |  |  |  |  |  |  |
|  |  |  | Sodium Polyoxyethylene (2.5) Lauryl Ether Acetate *4 |  |  |  | 0.055 |  |  |  |  |  |
|  |  |  | Sodium Polyoxyethylene (4.5) Lauryl Ether Acetate *5 |  |  |  |  | 0.055 |  |  |  |  |
|  |  |  | Sodium Polyoxyethylene (10) Lauryl Ether Acetate *6 |  |  |  |  |  | 0.055 |  |  |  |
|  |  |  | Sodium Polyoxyethylene (2.0) Oleyl Ether Acetate *7 |  |  |  |  |  |  | 0.055 |  |  |
|  |  |  | Sodium Polyoxyethylene (5.0) Oleyl Ether Acetate *8 |  |  |  |  |  |  |  | 0.055 |  |
|  |  |  | Sodium Polyoxyethylene (9.0) Oleyl Ether Acetate *9 |  |  |  |  |  |  |  |  | 0.055 |
|  |  |  | Pure Water | 13.42 | 13.42 | 13.42 | 13.42 | 13.42 | 13.42 | 13.42 | 13.42 | 13.42 |
|  | Step (II) | Component (C) | Sunflower Oil | 22.0 | 22.0 | 22.0 | 22.0 | 22.0 | 22.0 | 22.0 | 22.0 | 22.0 |
|  |  | Ratio by Mass | Component (B)/Component (A) | 0.1 | 0.1 | 0.1 | 0.1 | 0.1 | 0.1 | 0.1 | 0.1 | 0.1 |
|  |  |  | Component (C)/Component (A) | 40 | 40 | 40 | 40 | 40 | 40 | 40 | 40 | 40 |
|  |  | Emulsion Evaluation | Mean Particle Size of Oil Drops [μm] | 18.4 | 17.5 | 12.0 | 19.6 | 15.6 | 14.5 | 15.5 | 21.0 | 22.5 |
|  |  |  | Emulsion Condition | A | A | A | A | A | A | A | A | A |
|  | Step (III) | Component (B) | Sodium Polyoxyethylene (2) Lauryl Ether Sulfate *10 | 12.0 | 12.0 | 12.0 | 12.0 | 12.0 | 12.0 | 12.0 | 12.0 | 12.0 |
|  |  | Others | Cocoyl Fatty Acid Amide Propylbetaine *11 | 5.0 | 5.0 | 5.0 | 5.0 | 5.0 | 5.0 | 5.0 | 5.0 | 5.0 |
|  |  |  | Cocoyl Fatty Acid Monoethanolamide *12 | 3.0 | 3.0 | 3.0 | 3.0 | 3.0 | 3.0 | 3.0 | 3.0 | 3.0 |
|  |  |  | Glycerin | 6.5 | 6.5 | 6.5 | 6.5 | 6.5 | 6.5 | 6.5 | 6.5 | 6.5 |
|  |  |  | Lauric Acid *13 | 3.5 | 3.5 | 3.5 | 3.5 | 3.5 | 3.5 | 3.5 | 3.5 | 3.5 |
|  |  |  | Vaseline | 3.0 | 3.0 | 3.0 | 3.0 | 3.0 | 3.0 | 3.0 | 3.0 | 3.0 |
|  |  |  | Cationized Guar Gum *14 | 0.5 | 0.5 | 0.5 | 0.5 | 0.5 | 0.5 | 0.5 | 0.5 | 0.5 |
|  |  |  | Pure Water | | | | | balance | | | | |
| pH (20-fold dilution, 25° C.) | | | | 6.6 | 6.6 | 6.6 | 6.6 | 6.6 | 6.6 | 6.6 | 6.6 | 6.6 |
| Component (B)/Component (A) | | | | 21.9 | 21.9 | 21.9 | 21.9 | 21.9 | 21.9 | 21.9 | 21.9 | 21.9 |
| Evaluation Results | | | Remaining Oil Amount [mg/cm$^2$] | 1.0 | 1.0 | 1.0 | 0.7 | 0.8 | 0.8 | 0.6 | 1.1 | 1.0 |

TABLE 10-continued

|  |  | Example |  |  |  |  |  |  |  |  |
|---|---|---|---|---|---|---|---|---|---|---|
| Skin Cleanser Composition | | 52 | 53 | 54 | 55 | 56 | 57 | 58 | 59 | 60 |
| | Foamability in Washing | 5.0 | 5.0 | 5.0 | 5.0 | 5.0 | 5.0 | 5.0 | 5.0 | 5.0 |
| | Moisturization Feeling after Drying | 4.6 | 4.6 | 4.6 | 4.6 | 4.6 | 4.6 | 4.6 | 4.6 | 4.6 |

*1: Kao's trade name, EMAL O
*2: Kao's trade name, EMAL 170J
*3: Kao's trade name, EMAL 327
*4: Kao's trade name, KAOAKYPO RLM-25CA
*5: Kao's trade name, KAOAKYPO RLM-45NV
*6: Kao's trade name, KAOAKYPO RLM-100NV
*7: Kao's trade name, KAOAKYPO RO20VG
*8: Kao's trade name, KAOAKYPO RO50VG
*9: Kao's trade name, KAOAKYPO RO90VG
*10: Kao's trade name, EMAL 270S
*11: Kao's trade name, AMPHITOL 55AB
*12: Kawaken Fine Chemical's trade name, AMIZOL CME
*13: Kao's trade name, LUNAC L-98
*14: Sansho's trade name: JAGUAR C14S Examples 61 to 69

Production and Evaluation of Body Shampoo

In the same manner as in Examples 30 to 38, skin cleanser compositions of Examples shown in Table 11 were produced and evaluated. The results are shown in Table 11. Even though the type of the oil (C) was changed, the compositions of those Examples could be emulsified like the compositions of Examples 30 to 60.

TABLE 11

| | | | | Example | | | | | | | | |
|---|---|---|---|---|---|---|---|---|---|---|---|---|
| | | | Skin Cleanser Composition | 61 | 62 | 63 | 64 | 65 | 66 | 67 | 68 | 69 |
| Constitutive Components (part by mass) | Step (I) | Component (A) | C-HPC (23) | 0.55 | 0.55 | 0.55 | 0.55 | 0.55 | 0.55 | 0.55 | 055 | 0.55 |
| | | Component (B') | Sodium Polyoxyethylene (2) Lauryl Ether Sulfate *1 | 0.055 | 0.055 | 0.055 | 0.055 | 0.055 | 0.055 | 0.055 | 0.055 | 0.055 |
| | | | Pure Water | 13.42 | 13.42 | 13.42 | 13.42 | 13.42 | 13.42 | 13.42 | 13.42 | 13.42 |
| | Step (II) | Component (C) | Avocado Oil *2 | 22.0 | | | | | | | | |
| | | | Macadamia Nut Oil *3 | | 22.0 | | | | | | | |
| | | | Liquid Paraffin *4 | | | 22.0 | | | | | | |
| | | | Dipentaerythrityl (hydroxystearate/Stearate/Rosinate) *5 | | | | 22.0 | | | | | |
| | | | Isopropyl Palmitate *6 | | | | | 22.0 | | | | |
| | | | 2-Octyldodecanol *7 | | | | | | 22.0 | | | |
| | | | Polyether-Modified Silicone *8 | | | | | | | 22.0 | | |
| | | | Polyether-Modified Silicone *9 | | | | | | | | 22.0 | |
| | | | Dimethicone *10 | | | | | | | | | 22.0 |
| | Ratio by Mass | | Component (B)/Component (A) | 0.1 | 0.1 | 0.1 | 0.1 | 0.1 | 0.1 | 0.1 | 0.1 | 0.1 |
| | | | Component (C)/Component (A) | 40 | 40 | 40 | 40 | 40 | 40 | 40 | 40 | 40 |
| | Emulsion Evaluation | | Mean Particle Size of Oil Drops [μm] | 13.5 | 13.2 | 14.6 | 12.2 | 10.3 | 10.6 | 29.3 | 76.2 | 8.8 |
| | | | Emulsion Condition | A | A | A | A | A | A | A | A | A |
| | Step (III) | Component (B) | Sodium Polyoxyethylene (2) Lauryl Ether Sulfate *1 | 12.0 | 12.0 | 12.0 | 12.0 | 12.0 | 12.0 | 12.0 | 12.0 | 12.0 |
| | | Others | Cocoyl Fatty Acid Amide Propylbetaine *11 | 5.0 | 5.0 | 5.0 | 5.0 | 5.0 | 5.0 | 5.0 | 5.0 | 5.0 |
| | | | Cocoyl Fatty Acid Monoethanolamide *12 | 3.0 | 3.0 | 3.0 | 3.0 | 3.0 | 3.0 | 3.0 | 3.0 | 3.0 |
| | | | Glycerin | 6.5 | 6.5 | 6.5 | 6.5 | 6.5 | 6.5 | 6.5 | 6.5 | 6.5 |
| | | | Lauric Acid *13 | 3.5 | 3.5 | 3.5 | 3.5 | 3.5 | 3.5 | 3.5 | 3.5 | 3.5 |
| | | | Vaseline | 3.0 | 3.0 | 3.0 | 3.0 | 3.0 | 3.0 | 3.0 | 3.0 | 3.0 |
| | | | Cationized Guar Gum *14 | 0.5 | 0.5 | 0.5 | 0.5 | 0.5 | 0.5 | 0.5 | 0.5 | 0.5 |
| | | | Pure Water | | | | | balance | | | | |

TABLE 11-continued

| Skin Cleanser Composition | Example | | | | | | | | |
|---|---|---|---|---|---|---|---|---|---|
| | 61 | 62 | 63 | 64 | 65 | 66 | 67 | 68 | 69 |
| pH (20-fold dilution, 25° C.) | 6.6 | 6.6 | 6.6 | 6.6 | 6.6 | 6.6 | 6.6 | 6.6 | 6.6 |
| Component (B)/Component (A) | 21.9 | 21.9 | 21.9 | 21.9 | 21.9 | 21.9 | 21.9 | 21.9 | 21.9 |

*1: Kao's trade name, EMAL 270S
*2: Nikko Chemicals' trade name, Pure Avocado Oil
*3: Nikko Chemicals' trade name, Macadamia Nut Oil
*4: Kaneda's trade name, HICALL K-230
*5: Nisshin Oillio's trade name, COSMOL 168ARV
*6: Kao's trade name, EXCEPARL IPP
*7: Kao's trade name, KALCOL 200GD
*8: Shin-etsu Chemical Industry's trade name, KF6011
*9: Kao's trade name, SOFCARE GS-G
*10: Shin-etsu Chemical Industry's trade name, KF-96H 100,000 cs
*11: Kao's trade name, AMPHITOL 55AB
*12: Kawaken Fine Chemical's trade name, AMIZOL CME
*13: Kao's trade name, LUNAK L-98
*14: Sansho's trade name, JAGUAR C14S

INDUSTRIAL APPLICABILITY

The skin cleanser composition of the invention can provides an excellent frictional resistance feeling during rinsing and can give an excellent silky feeling with moisturization to the skin after drying, and therefore can be favorably used, for example, in the field of skin cleansers such as face wash, cleaning agent, body soap, hand soap, massage agent, etc.

The invention claimed is:

1. A skin cleanser composition comprising a cationized hydroxypropyl cellulose (A) and a surfactant (B), wherein the cationized hydroxypropyl cellulose (A) has an anhydroglucose-derived main chain represented by the following general formula (1), and has a degree of substitution with cationized ethyleneoxy group of from 0.01 to 3.0 and a degree of substitution with propyleneoxy group of from 0.01 to 2.9:

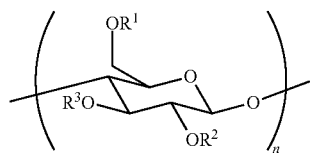

(1)

wherein $R^1$, $R^2$ and $R^3$ each independently represent a substituent having a cationized ethyleneoxy group and a propyleneoxy group represented by the following general formula (2); n indicates a mean degree of polymerization of anhydroglucose and is a number of from 20 to 5000,

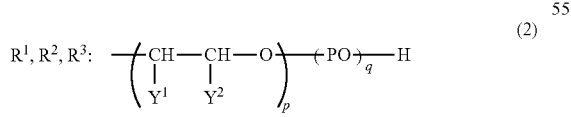

(2)

wherein one of $Y^1$ and $Y^2$ is a hydrogen atom and the other is a cationic group represented by the following general formula (3); PO represents a propyleneoxy group; p indicates the number of cationized ethyleneoxy groups (—CH($Y^1$)—CH($Y^2$)—O—) in the general formula (2) and q indicates the number of propyleneoxy groups (—PO—) therein, each being 0 or a positive integer; in case where both of p and q are not 0, the addition sequence of the cationized ethyleneoxy group and the propyleneoxy group is not defined, and in case where p and/or q are/is 2 or more, a binding form may be a block co-polymer or a random co-polymer;

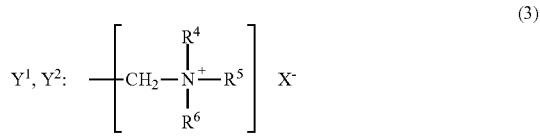

(3)

wherein $R^4$, $R^5$ and $R^6$ each independently represent a linear or branched alkyl group having from 1 to 3 carbon atoms, and $X^-$ represents an anionic group.

2. The skin cleanser composition according to claim 1, wherein the content of the cationized hydroxypropyl cellulose (A) is from 0.005 to 10% by mass.

3. The skin cleanser composition according to claim 1, wherein the mean degree of polymerization, n, of the anhydroglucose in the general formula (1) is from 100 to 500.

4. The skin cleanser composition according to claim 1, wherein the ratio of the cationized hydroxypropyl cellulose (A) to the surfactant (B) in the skin cleanser composition is, as a ratio by mass of [cationized hydroxypropyl cellulose/surfactant], from 0.0001 to 1.

5. The skin cleanser composition according to claim 1, wherein the cationized hydroxypropyl cellulose (A) is obtained by the following steps (a-1) to (a-3):

Step (a-1): a step of adding a cationizing agent to a cellulose-containing raw material and processing it with a grinder, Step (a-2): a step of adding a base to the grinder-processed product obtained in the step (a-1), and while processing it with a grinder, reacting the cellulose-containing raw material and the cationizing agent to give a cationized cellulose, Step (a-3): a step of reacting the cationized cellulose obtained in the step (a-2) with propylene oxide to give the cationized hydroxypropyl cellulose (A).

6. The skin cleanser composition according to claim 1, wherein the cationized hydroxypropyl cellulose (A) is obtained by the following steps (b-1) to (b-4):

Step (b-1): a step of processing a cellulose-containing raw material with a grinder to give a cellulose-containing raw material that comprises a cellulose having a degree of crystallinity of from 10 to 50%, Step (b-2): a step of adding to the cellulose-containing raw material obtained in the step (b-1), a base in an amount of from 0.6 to 1.5 molar times per mol of the anhydroglucose unit that constitutes the cellulose, and water in an amount of from 20 to 100% by mass relative to the cellulose in the cellulose-containing raw material, thereby giving an alkali cellulose, Step (b-3): a step of reacting the alkali cellulose obtained in the step (b-2) with propylene oxide to give a hydroxypropyl cellulose, Step (b-4): a step of reacting the hydroxypropyl cellulose obtained in the step (b-3) with a cationizing agent to give the cationized hydroxypropyl cellulose (A).

7. The skin cleanser composition according to claim 1, wherein the cationized hydroxypropyl cellulose (A) is obtained by the following steps (c-1) to (c-4):

Step (c-1): a step of processing a mixture of a cellulose-containing raw material and a base in an amount of from 0.6 to 1.5 molar times per mol of the anhydroglucose unit that constitutes the cellulose in the cellulose-containing raw material, with a grinder under the condition where the water content in the cellulose-containing raw material is at most 10% by weight relative to the cellulose therein, thereby giving a ground cellulose/base mixture in which the mean particle size of the cellulose is from 10 to 150 μm, Step (c-2): a step of adding water to the ground cellulose/base mixture obtained in the step (c-1) to thereby control the water content in the ground cellulose/base mixture to be from 30 to 100% by mass relative to the cellulose in the cellulose-containing raw material used in the step (c-1), thereby giving an alkali cellulose, Step (c-3): a step of reacting the alkali cellulose obtained in the step (c-2) with propylene oxide to give a hydroxypropyl cellulose, Step (c-4): a step of reacting the hydroxypropyl cellulose obtained in the step (c-3) with a cationizing agent to give the cationized hydroxypropyl cellulose (A).

8. The skin cleanser composition according to claim 1, which further comprises an oil (C).

9. The skin cleanser composition according to claim 8, wherein the content of the oil (C) is from 1 to 40% by mass.

10. The skin cleanser composition according to claim 8, wherein the ratio by mass of the oil (C) to the cationized hydroxypropyl cellulose (A) [oil (C)/cationized hydroxypropyl cellulose (A)] is from 1 to 400.

\* \* \* \* \*